(12) United States Patent
Zhang

(10) Patent No.: US 7,754,729 B2
(45) Date of Patent: Jul. 13, 2010

(54) QUINAZOLINE AND QUINOLINE DERIVATIVES AS IRREVERSIBLE PROTEIN TYROSINE KINASE INHIBITORS

(76) Inventor: Hesheng Zhang, Xiao Yuan Cun 31-101 Teda, Tianjin (CN) 300457

( * ) Notice: Subject to any disclaimer, the term of this patent is extended or adjusted under 35 U.S.C. 154(b) by 0 days.

(21) Appl. No.: 12/342,104

(22) Filed: Dec. 23, 2008

(65) Prior Publication Data

US 2009/0105247 A1  Apr. 23, 2009

Related U.S. Application Data

(63) Continuation of application No. PCT/CN2007/001920, filed on Jun. 19, 2007.

(30) Foreign Application Priority Data

Jul. 5, 2006 (CN) .......... 2006 1 0014690
Nov. 10, 2006 (CN) .......... 2006 1 0138377

(51) Int. Cl.
 *A61K 31/517* (2006.01)
(52) U.S. Cl. .......... 514/266.4; 544/293; 546/184
(58) Field of Classification Search .......... 544/293
 See application file for complete search history.

(56) References Cited

OTHER PUBLICATIONS

West, Anthony R., Solid State Chemistry and its Applications, Wiley, New York, 1988, pp. 358 and 365.*

* cited by examiner

*Primary Examiner*—James O Wilson
*Assistant Examiner*—Brian McDowell
(74) *Attorney, Agent, or Firm*—Matthias Scholl P.C.; Scholl, Matthias

(57) ABSTRACT

A compound of formula (I),

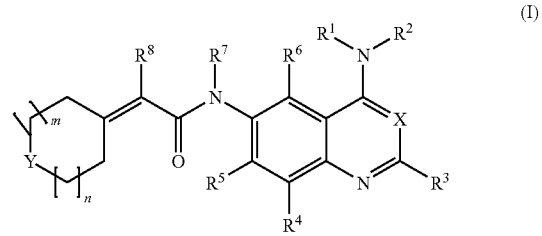

a pharmaceutically acceptable salt, or hydrate thereof, and a method of preparing the same. A method of treating or preventing a physiological disorder caused by abnormal protein tyrosine kinase activity in a mammal comprising administering to said mammal a pharmaceutical composition comprising a compound of formula (I).

8 Claims, No Drawings

QUINAZOLINE AND QUINOLINE DERIVATIVES AS IRREVERSIBLE PROTEIN TYROSINE KINASE INHIBITORS

CROSS-REFERENCE TO RELATED APPLICATIONS

This application is a continuation of International Patent Application No. PCT/CN2007/001920 with an international filing date of Jun. 19, 2007, designating the United States, now pending, and further claims priority benefits to Chinese Patent Application No. 200610014690.1 filed Jul. 5, 2006 and Chinese Patent Application No. 200610138377.9 filed Nov. 10, 2006. The contents of all of the aforementioned applications, including any intervening amendments thereto, are incorporated herein by reference.

BACKGROUND OF THE INVENTION

1. Field of the Invention

The invention relates to quinazoline and quinoline derivatives, a method of their preparation, and a method of using the same as pharmaceutical agents.

2. Description of the Related Art

Protein tyrosine kinases (PTKs) modulate a wide variety of cellular events, including differentiation, growth, metabolism, and apoptosis. Transmembrane receptor tyrosine kinases (RTKs), members of the PTK family, are the high affinity cell surface receptors for many polypeptide growth factors, cytokines and hormones.

The mechanisms by which most RTKs transmit signals are now well established. Binding of ligand results in the dimerization of receptor monomers followed by transphosphorylation of tyrosine residues within the cytoplasmic domains of the receptors. However, mutations in the transmembrane (TM) domains of RTKs have been implicated in the induction of pathological phenotypes. These mutations are believed to stabilize the RTK dimers, and thus promote unregulated signaling without ligand binding.

Overexpression of PTK in cells can cause weak signals to be amplified. Furthermore, during many steps of cellular signal transfer, the occurrence of mutations or overexpression of PTK can cause false signals. These false signals play a role in carcinogenesis.

Epidermal growth factor receptor (EGFR) is one of the typical examples. EGFR belongs to cell surface receptors of epidermal growth factor receptor tyrosine kinase (EGFR-TK). The receptor family comprises EGF receptor (a protein product of oncogene erbB-1), erbB-2 (c-neu or HER2) receptor, tumor protein mutant erbB-3 receptor, and erbB-4 receptor. EGF and transforming growth factor alpha (TGFα) are the two most important ligands of EGFR. Though the receptor plays a minor role in healthy adults, it is closely related to the pathological process of most cancers, particularly to colon cancer and breast cancer. Therefore, an EGFR-TK inhibitor that can block the transfer of these receptor signals can be used to treat cancers caused by EGFR overexpression, such as colorectal cancer, breast cancer, kidney cancer, lung cancer, and head and neck cancer.

An EGFR-TK inhibitor can also be used to treat other diseases caused by EGFR overexpression, such as psoriasis, nephritis and pancreatitis which are described below.

Conventional treatments for proliferative skin diseases such as psoriasis include anti-cancer drugs, such as methotrexate. However, methotrexate has strong side effects and response is poor within the necessary limited dosage. In psoriatic tissues, TGFα is the main growth factor that is overexpressed. In animal experiments, 50% of transgenic mice with TGFα overexpression produce psoriasis, which suggests that a good inhibitor of EGFR signal transfer mechanism may inhibit psoriasis, i.e., the EGFR-TK inhibitor can relieve psoriasis symptoms.

EGF is an important epithelial mitogen and plays a role in renal tubular cell replication. In streptozotocin-induced diabetic mice, secretion of urine and mRNA of EGF are increased fourfold. Additionally, the expression of EGFR is enhanced in patients with proliferative glomerulonephritis (Roy-Chaudhury et al., Pathology, 1993, 25, 327-332). These findings indicate blocking EGF signal transfer can be used to treat and prevent renal injury. Therefore, it is postulated that an EGFR-TK inhibitor could be used to treat proliferative glomerulonephritis and renal disease induced by diabetes.

It has been reported that in chronic pancreatitis patients the expression of EGFR and TGFα is much higher than in healthy adults (Korc et al., Gut, 1994, 35, 1468). The over expression of erbB-2 receptor has been confirmed in patients with severe chronic pancreatitis (Friess et al., Ann. Surg., 1994, 220, 183). Therefore, it is postulated that an EGFR-TK inhibitor could potentially be used to treat pancreatitis.

During embryonic cell maturation, embryonic cell implantation in endometrium, and other peripheral implantation, EGF and TGFα are present in uterine tissues (Taga, Nippon Sanka Fujinka Gakkai Zasshi, 1992, 44, 939) and EGFR levels are increased (Brown et al., Endocrinology, 1989, 124, 2882). Meanwhile, heparin-binding EGF (HB-EGF) is expressed in the uterus in a blastocyst-mediated process. (Das et al, Development, 1994, 120, 1071). TGFα and EGFR are highly expressed in embryonic cells (Adamson, Mol. Reprod. Dev., 1990, 27, 16). Surgical removal the submandibular gland and treatment with monoclonal antibody against EGFR can greatly reduce the fertility of mice by decreasing the success of embryonic cell implantation (Tsutsumi et al., J. Endocrinology, 1993, 138, 437). These results indicate that an EGFR-TK inhibitor may function as a contraceptive.

WO1992/007844 and WO1992/014716 disclose 2,4-diaminoquinazoline derivatives which are used as potentiators of chemotherapeutic agents in the treatment of cancer.

WO1992/020642 discloses bis mono- and bicyclic aryl and heteroaryl compounds which inhibit EGF and/or PDGF receptor tyrosine kinase.

EP520722, EP566226, EP635498, EP602851, WO 1995/019774 and WO 1995/15758 relate to reversible EGF receptor tyrosine kinase inhibitors. These inhibitors belong to the family of aryl and heteroaryl quinazoline derivatives and some exhibit a high inhibitory activity against EGF receptor tyrosine kinase. However, in animal pathological models these inhibitors exhibit low activity. The reason for this lies in that PTK is a catalyst catalyzing a phosphate group to transfer from ATP to a protein tyrosine residue, and the above-mentioned reversible EGF receptor tyrosine kinase inhibitors compete with ATP to bind EGF receptor tyrosine kinase, but in cells the ATP concentration is much higher (mM grade). Thus, the reversible EGF receptor tyrosine kinase inhibitors exhibiting a high activity in vitro have difficulty functioning in pathological animal models. However, since irreversible EGF receptor tyrosine kinase inhibitors do not compete with ATP, they are expected to do better in vivo.

Irreversible EGF receptor tyrosine kinase inhibitors are known and much effort has been devoted to their development. One type of irreversible EGF receptor tyrosine kinase inhibitors features a Michael acceptor at the sixth position of quinazoline, so that a Michael addition reaction can occur between the inhibitor and cysteine sulfhydryl in the active center pocket wall of EGF receptor tyrosine kinase. Furthermore, the activity of the inhibitor has a positive correlation with the activation energy of the Michael addition reaction between the inhibitor and cysteine sulfhydryl.

SUMMARY OF THE INVENTION

In view of the above-described problems, it is an objective of the invention to provide a compound or pharmaceutically acceptable salt or hydrate thereof which can inhibit protein tyrosine kinase activity.

It is another objective of the invention to provide a pharmaceutical preparation comprising an excipient and a compound or pharmaceutically acceptable salt or hydrate thereof which inhibits protein tyrosine kinase activity.

It is still another objective of the invention to provide a method of preparing a compound which irreversibly inhibits protein tyrosine kinase activity.

To achieve the above objectives, in accordance with one embodiment of the invention, provided is a compound of formula (I),

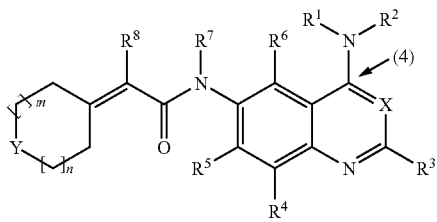

wherein X represents N, C—CN, or CH; Y represents $CH_2$, S, O or N—$R^9$; $R^1$, $R^3$, $R^7$ and $R^8$ independently represent H, $CF_3$, or $C_{1-6}$alkyl; $R^2$ represents a group selected from formula (II), (III), (IV), (V), (VI), (VII) or (VIII);

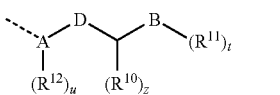

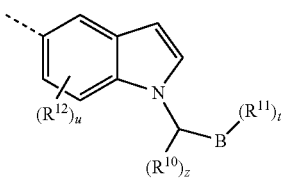

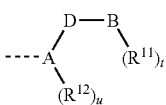

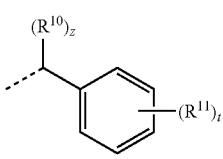

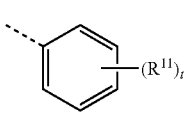

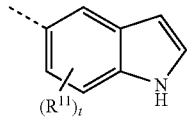

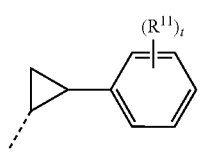

$R^4$ and $R^6$ independently represent H, $C_{1-6}$alkyl, $OC_{1-6}$alkyl, OH, F, Cl, Br, $OCF_3$, or trifluoromethyl; $R^5$ is independently at each occurrence selected from H, F, $C_{1-6}$alkyl, OH, $OC_{1-6}$alkyl, $OCF_3$, $OCF_2CH_3$, $NH_2$, $NH(C_{1-6}alkyl)$, $N(C_{1-6}alkyl)_2$, 1-pyrrolinyl, 1-piperidyl, 4-morpholinyl, Cl, Br, trifluoromethyl, $O(CH_2)_{2-4}OCF_3$, $O(CH_2)_{2-4}OC_{1-6}alkyl$, $O(CH_2)_{2-4}NH(C_{1-6}alkyl)$, $O(CH_2)_{2-4}N(C_{1-6}alkyl)_2$, (1-pyrrolinyl)$(CH_2)_{2-4}$O, (1-piperidyl)$(CH_2)_{2-4}$O, (4-morpholinyl)$(CH_2)_{2-4}$O, NHC(O)H, NHC(O)($C_{1-6}$alkyl), N($C_{1-6}$alkyl)C(O)($C_{1-6}$alkyl), $O(CH_2)_{2-4}OH$, N($C_{1-6}$alkyl)C(O)O($C_{1-6}$alkyl), N($C_{1-6}$alkyl)C(O)OH, NHC(O)O($C_{1-6}$alkyl), OC(O)NH($C_{1-6}$alkyl), OC(O)N($C_{1-6}$alkyl)$_2$, (1-piperidyl)$(CH_2)_{2-4}$OC(O), (4-morpholinyl)$(CH_2)_{2-4}$OC(O), (1-pyrrolinyl)$(CH_2)_2$OC(O), (1-imidazolyl)$(CH_2)_{2-4}$O, (4-imidazolyl)$(CH_2)_{2-4}$OC(O), (pyrazolyl)$(CH_2)_{2-4}$O, (triazolyl)$(CH_2)_{2-4}$OC(O) or Ar$(CH_2)_{1-4}$O; $R^9$ at each occurrence is independently selected from H, $C_{1-6}$alkyl, $CF_3$, $CF_2CH_3$, $(CH_2)_2$OH, $(CH_2)_{1-4}OC_{1-6}$alkyl, $(CH_2)_{1-4}NH(C_{1-6}alkyl)$, $(CH_2)_{1-4}N(C_{1-6}alkyl)_2$, (1-pyrrolinyl)$(CH_2)_{1-4}$, (1-piperidyl)$(CH_2)_{1-4}$, (4-morpholinyl)$(CH_2)_{1-4}$, C(O)$C_{1-6}$alkyl, C(O)$(CH_2)_{1-4}$OH, C(O)$(CH_2)_{1-4}OC_{1-6}$alkyl, C(O)$(CH_2)_{1-4}N(C_{1-6}alkyl)_2$, (1-pyrrolinyl)$(CH_2)_{1-6}$C(O), (1-piperidyl)$(CH_2)_{1-6}$C(O), (4-morpholinyl)$(CH_2)_{1-4}$C(O), C(O)$OC_{1-6}$alkyl, C(O)$O(CH_2)_{2-4}OC_{1-6}$alkyl, C(O)$O(CH_2)_{2-4}N(C_{1-6}alkyl)_2$, C(O)$O(CH_2)_{2-4}NH(C_{1-6}$ alkyl), (1-pyrrolinyl)$(CH_2)_{2-4}$OC(O), (1-piperidyl)$(CH_2)_2$OC(O), (4-morpholinyl)$(CH_2)_{2-4}$OC(O), $(CH_2)_{1-4}$C(O)$OC_{1-6}$alkyl, or Ar$(CH_2)_{1-4}$; $R^{10}$ represents $C_{1-6}$alkyl, or F; $R^{11}$ and $R^{12}$ represent independently at each occurrence F, Cl, Br, I, CN, $NO_2$, $CF_3$, OH, $NH_2$, $C_{1-4}$alkyl, $OC_{1-4}$alkyl, $OCF_3$, $OCF_2CH_3$, NH($C_{1-4}$alkyl), N($C_{1-4}$alkyl)$_2$, OC(O)$C_{1-4}$alkyl, NHC(O)H, NHC(O)$C_{1-4}$alkyl, N($C_{1-4}$alkyl)C(O)$C_{1-4}$alkyl, C(O)$OC_{1-4}$alkyl, C(O)NH$C_{1-4}$alkyl, C(O)N($C_{1-4}$alkyl)$_2$, COOH, C(O)$C_{1-4}$alkyl, S(O)$C_{1-4}$alkyl, $SO_2C_{1-4}$alkyl, $SO_2$NH$C_{1-4}$alkyl or $SO_2$N($C_{1-4}$alkyl)$_2$; A, B independently represent aromatic ring; Ar is phenyl, substituted phenyl, or pyridyl; D represents O, S, NH, or methylene; m, n independently represent an integer from 0 to 4; z is 0, 1, or 2; and t and u independently represent an integer from 0 to 4.

In the embodiments of the invention, $C_{1-4}$alkyl and $C_{1-6}$alkyl are straight chain alkyl, branched chain alkyl, or cyclic alkyl, saturated or unsaturated alkyl, optionally substituted with F, OH, COOH, $CO_2(C_{1-4}alkyl)$, C(O)$NH_2$, C(O)NH($C_{1-4}$alkyl), C(O)N($C_{1-4}$alkyl)$_2$, NHC(O)($C_{1-4}$alkyl), $NH_2$, NH($C_{1-4}$alkyl), N($C_{1-4}$alkyl)$_2$, NHC(O)$NH_2$, NHC(NH)$NH_2$, O($C_{1-4}$alkyl), or S($C_{1-4}$alkyl).

When A, B independently represent an aromatic ring, the ring is a 5 to 7-membered and contains from 0 to 4 heteroatoms, such as N, O or S. A, B can also independently represent a polycyclic aromatic group consisting of two or three 5 to 7-membered fused rings.

In the embodiments of the invention, the connecting position of the group $R^2$ connected to the amine group of the fourth position of the mother nucleus is not limited to the position as shown by the broken line, other position is also applicable.

When the compound of formula (I) is defined as an E/Z isomer, it can be an E isomer or a Z isomer or a mixture of an E isomer and a Z isomer.

When the compound of formula (I) is defined as an R/S isomer, it can be an R isomer, or an S isomer, or a mixture of an R isomer and an S isomer.

The uniqueness of the compound of the invention is clearly visualized by comparing the structure and property of the compound of Example 33 with the comparison compound A of Example 84, compound B of Example 85 and compound C.

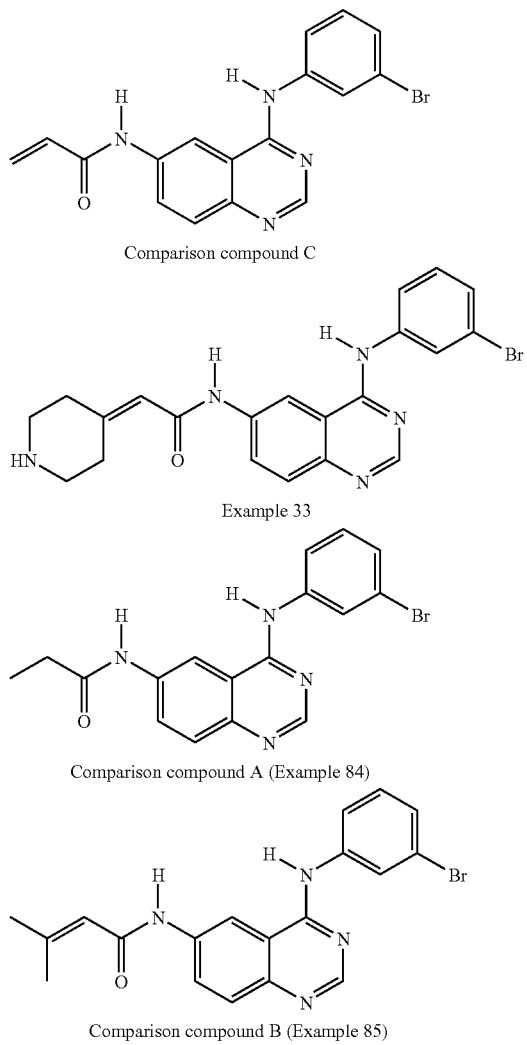

Comparison compound C

Example 33

Comparison compound A (Example 84)

Comparison compound B (Example 85)

The comparison compound C is an irreversible small molecular EGFR-TK inhibitor having the highest activity among all literature-reported compounds. At a molecular level, the $EC_{50}$ value of the comparison compound C against EGFR-TK is $10^{-7}$ μM, while in the same test $EC_{50}$ value of the comparison compound B is merely about 0.5 μM, which means the activity of the comparison compound B is five million times lower compared to the comparison compound C. The difference between the two compounds in chemical structure is merely the difference in the steric hindrance of substituted branch of the sixth position. Based on that rule, the activity of the compound of the invention should be lower than that of the comparison compound B.

However, in a test of inhibitory activity of EGFR-TK at cellular level, the activity of the compound of the invention was unexpectedly several orders of magnitude higher than that of the comparison compound B. For example, the activity of the compound in Example 33 is not only much higher than that of the comparison compound B, but also close to the comparison compound A (as shown in Table 3, 4). However, the $EC_{50}$ value of the comparison compound A and C against EGFR-TK is equivalent at the molecular level, which means that the activity of the compound in Example 33 is equivalent to that of the comparison compound C, and it is a million times higher than that of the comparison compound B.

It has been reported in the literature that the activity of an irreversible EGFR-TK inhibitor is ten times higher than that of a reversible EGFR-TK inhibitor in A431 animal tumor model, but that the activity of the two is equivalent at a molecular level. The compound of the present invention is proven to be an irreversible EGFR-TK inhibitor by a cellular model test (as shown in Table 5), while the high activity comparison compound A to be a reversible inhibitor in the same test, which conforms to the results of a direct test using EGFR-TK described in the literature.

The compounds of the invention also inhibit Her-2 TK, and part of the results are listed in Table 6.

The compounds of the invention show a certain degree of growth inhibition against epidermal cancer cell strain A431, colorectal cancer cell strain LoVo, breast cancer cell strain BT 474 and breast cancer cell strain SK-Br-3. A part of the test results are listed in Tables 7, 8 and 9. Some compounds have 30 times higher growth-inhibition activities against A431 than Tarceva (as shown in Table 7). Some compounds have equivalent growth-inhibition activities against breast cancer with Lapatinib (as shown in Table 8). Some have better growth-inhibition activities against colorectal cancer cell LoVo than adriamycin (as shown in Table 9).

Accordingly, the invention teaches a method of inhibiting cancer cell growth in mammals comprising administering to a mammal in need thereof the compound of formula (I) or pharmaceutically acceptable salt or hydrate thereof, wherein the cancer includes but is not limited to breast cancer, skin cancer, colorectal cancer, head and neck cancer, lung cancer, kidney cancer, bladder cancer, ovarian cancer, oral cancer, laryngeal cancer, esophageal cancer, gastric cancer, cervical cancer, or liver cancer.

The compound of formula (I) suitable for being used as medical active ingredient comprises the compounds wherein $R^1$ represents H, $CH_3$, or $CH_2CH_3$, more particularly $R^1$ represents H.

The compound of formula (I) suitable for being used as medical active ingredient comprises the compounds wherein $R^3$ represents H, $CH_3$ or $CH_2CH_3$, more particularly $R^3$ represents H.

The compound of formula (I) suitable for being used as medical active ingredient comprises the compounds wherein $R^7$ represents H, $CH_3$ or $CH_2CH_3$, more particularly $R^7$ represents H.

The compound of formula (I) suitable for being used as medical active ingredient comprises the compounds wherein $R^8$ represents H, $CH_3$ or $CH_2CH_3$, more suitably $R^8$ represents H.

The compound of formula (I) suitable for being used as medical active ingredient comprises the compounds wherein $R^4$ represents H, F, $CH_3$, $CH_2CH_3$, $CH_2CH_2CH_3$, $OCH_3$, or OCH$_2$CH$_3$; more particularly, R$^4$ represents H, F, CH$_3$, CH$_2$CH$_3$ or OCH$_3$; and most particularly, R$^4$ represents H, F, CH$_3$, or OCH$_3$.

The compound of formula (I) suitable for being used as medical active ingredient comprises the compounds wherein R$^6$ represents H, F, CH$_3$, CH$_2$CH$_3$, CH$_2$CH$_2$CH$_3$, OCH$_3$, OCF$_3$ or OCH$_2$CH$_3$; more particularly, R$^6$ represents H, F, CH$_3$, CH$_2$CH$_3$ or OCH$_3$; and most particularly, R$^6$ represents H, F, CH$_3$, or OCH$_3$.

The compound of formula (I) suitable for being used as medical active ingredient comprises the compounds wherein A represents benzene ring, pyridine, pyrimidine, pyrazine, 4-nitrogen heterocyclic pyridine, pyrrole, furan, thiophene, pyrazole, thiazole, indole, benzofuran, benzothiophene, or naphthalene ring; more particularly, A represents benzene ring, pyridine, thiophene, pyrazole, thiazole, indole, or naphthalene ring.

The compound of formula (I) suitable for being used as medical active ingredient comprises the compounds wherein B represents benzene ring, pyridine, pyrimidine, pyrazine, 4-nitrogen heterocyclic pyridine, pyrrole, furan, thiophene, pyrazole, thiazole, indole, benzofuran, benzothiophene or naphthalene ring; and more particularly, B represents benzene ring, pyridine, thiophene, pyrazole, thiazole, indole, or naphthalene ring.

The compound of formula (I) suitable for being used as medical active ingredient comprises the compounds wherein D represents O, S, or NH; more particularly, D represents O.

The compound of formula (I) suitable for being used as medical active ingredient comprises the compounds wherein R$^{10}$ represents F, CH$_3$, CF$_3$, or Et, and z is 0, 1, or 2; more particularly, R$^{10}$ represents F, CH$_3$, or CF$_3$, and z is 0, 1 or 2; and most particularly, z is 0.

The compound of formula (I) suitable for being used as medical active ingredient comprises the compounds wherein R$^{11}$ represents independently at each occurrence F, Cl, Br, CN, NO$_2$, CF$_3$, OH, CH$_3$, CH$_2$CH$_3$, CH$_2$CH$_2$CH$_3$, alkynyl, OCH$_3$, OCH$_2$CH$_3$, OCF$_3$, CO$_2$CH$_3$, CO$_2$CH$_2$CH$_3$, NH$_2$, NHCH$_3$, NHCH$_2$CH$_3$, N(CH$_3$)$_2$, NHC(O)H, NHC(O)CH$_3$, NHC(O)CH$_2$CH$_3$, N(CH$_3$)C(O)CH$_3$, C(O)NHCH$_3$, C(O)NHCH$_2$CH$_3$ or C(O)N(CH$_3$)$_2$; more particularly, R$^{11}$ represents independently at each occurrence F, Cl, Br, CN, CF$_3$, OH, CH$_3$, CH$_2$CH$_3$, ethynyl, OCH$_3$, OCH$_2$CH$_3$, OCF$_3$, CO$_2$CH$_3$, CO$_2$CH$_2$CH$_3$, NH$_2$, NHCH$_3$, NHCH$_2$CH$_3$, N(CH$_3$)$_2$ or NHC(O)CH$_3$, most particularly, R$^{11}$ represents independently at each occurrence F, Cl, Br, CN, CF$_3$, CH$_3$, CH$_2$CH$_3$, ethynyl, OCH$_3$, OCH$_2$CH$_3$, OCF$_3$, CO$_2$CH$_2$CH$_3$, NH$_2$, NHCH$_3$, NHCH$_2$CH$_3$, N(CH$_3$)$_2$, or NHC(O)CH$_3$.

The compound of formula (I) suitable for being used as medical active ingredient comprises the compounds wherein t is an integer from 0 to 4; and more particularly t is 0, 1 or 2.

The compound of formula (I) suitable for being used as medical active ingredient comprises the compounds wherein R$^{12}$ represent independently at each occurrence F, Cl, Br, CN, NO$_2$, CF$_3$, OH, CH$_3$, CH$_2$CH$_3$, CH$_2$CH$_2$CH$_3$, alkynyl, OCH$_3$, OCH$_2$CH$_3$, OCF$_3$, CO$_2$CH$_3$, CO$_2$CH$_2$CH$_3$, NH$_2$, NHCH$_3$, NHCH$_2$CH$_3$, N(CH$_3$)$_2$, NHC(O)H, NHC(O)CH$_3$, NHC(O)CH$_2$CH$_3$, N(CH$_3$)C(O)CH$_3$, C(O)NHCH$_3$, C(O)NHCH$_2$CH$_3$ or C(O)N(CH$_3$)$_2$; and more particularly, R$^{12}$ represent independently at each occurrence F, Cl, Br, CN, CF$_3$, OH, CH$_3$, CH$_2$CH$_3$, ethynyl, OCH$_3$, OCH$_2$CH$_3$, OCF$_3$, CO$_2$CH$_3$, CO$_2$CH$_2$CH$_3$, NH$_2$, NHCH$_3$, NHCH$_2$CH$_3$, N(CH$_3$)$_2$, or NHC(O)CH$_3$.

The compound of formula (I) suitable for being used as medical active ingredient comprises the compounds wherein u is an integer from 0 to 4; and more particularly u is 0, 1 or 2.

The compound of formula (I) suitable for being used as medical active ingredient comprises the compounds wherein R$^5$ is independently at each occurrence selected from H, F, OH, CH$_3$, CH$_2$CH$_3$, CH$_2$CH$_2$CH$_3$, OCH$_3$, OCH$_2$CH$_3$, OCF$_3$, OCF$_2$CH$_3$, NH$_2$, NHCH$_3$, N(CH$_3$)$_2$, 1-pyrrolinyl, 1-piperidyl, 4-morpholinyl, trifluoromethyl, O(CH$_2$)$_2$OH, O(CH$_2$)$_3$OH, O(CH$_2$)$_4$OH, O(CH$_2$)$_2$OCH$_3$, O(CH$_2$)$_3$OCH$_3$, O(CH$_2$)$_4$OCH$_3$, O(CH$_2$)$_2$OCH$_2$CH$_3$, O(CH$_2$)$_3$OCH$_2$CH$_3$, O(CH$_2$)$_4$OCH$_2$CH$_3$, O(CH$_2$)$_2$N(CH$_3$)$_2$, O(CH$_2$)$_3$N(CH$_3$)$_2$, O(CH$_2$)$_4$N(CH$_3$)$_2$, O(CH$_2$)$_2$N(CH$_2$CH$_3$)$_2$, O(CH$_2$)$_3$N(CH$_2$CH$_3$)$_2$, O(CH$_2$)$_4$N(CH$_2$CH$_3$)$_2$, O(CH$_2$)$_2$N(CH$_3$)CH$_2$CH$_3$, O(CH$_2$)$_3$N(CH$_3$)CH$_2$CH$_3$, O(CH$_2$)$_4$N(CH$_3$)CH$_2$CH$_3$, O(CH$_2$)$_2$NH(CH$_3$), O(CH$_2$)$_3$NH(CH$_3$), O(CH$_2$)$_4$NH(CH$_3$), (1-pyrrolinyl)(CH$_2$)$_2$O, (1-pyrrolinyl)(CH$_2$)$_3$O, (1-pyrrolinyl)(CH$_2$)$_4$O, (1-piperidyl)(CH$_2$)$_2$O, (1-piperidyl)(CH$_2$)$_3$O, (1-piperidyl)(CH$_2$)$_4$O, (4-morpholinyl)(CH$_2$)$_2$O, (4-morpholinyl)(CH$_2$)$_3$O, (4-morpholinyl)(CH$_2$)$_4$O, NHC(O)H, NHC(O)CH$_3$, NHC(O)CH$_2$CH$_3$, NHC(O)CH$_2$CH$_2$CH$_3$, N(CH$_3$)C(O)H, N(CH$_3$)C(O)CH$_3$, N(CH$_3$)C(O)CH$_2$CH$_3$, N(CH$_3$)C(O)CH$_2$CH$_2$CH$_3$, NHC(O)OCH$_3$, NHC(O)OCH$_2$CH$_3$, N(CH$_3$)C(O)OCH$_3$, N(CH$_3$)C(O)OCH$_2$CH$_3$, N(CH$_3$)C(O)OCH$_2$CH$_2$CH$_3$, OC(O)NHCH$_3$, OC(O)NHCH$_2$CH$_3$, OC(O)N(CH$_3$)$_2$, or OC(O)N(CH$_3$)CH$_2$CH$_3$.

The compound of formula (I) suitable for being used as medical active ingredient comprises the compounds wherein R$^9$ is independently at each occurrence selected from H, CH$_3$, CH$_2$CH$_3$, CH$_2$CH$_2$CH$_3$, CF$_3$, CF$_2$CH$_3$, (CH$_2$)$_2$OH, (CH$_2$)$_3$OH, (CH$_2$)$_4$OH, (CH$_2$)$_2$OCH$_3$, (CH$_2$)$_3$OCH$_3$, (CH$_2$)$_4$OCH$_3$, (CH$_2$)$_2$OCH$_2$CH$_3$, (CH$_2$)$_3$OCH$_2$CH$_3$, (CH$_2$)$_4$OCH$_2$CH$_3$, (CH$_2$)$_2$N(CH$_3$)$_2$, (CH$_2$)$_3$N(CH$_3$)$_2$, (CH$_2$)$_4$N(CH$_3$)$_2$, (CH$_2$)$_2$N(CH$_2$CH$_3$)$_2$, (CH$_2$)$_3$N(CH$_2$CH$_3$)$_2$, (CH$_2$)$_4$N(CH$_2$CH$_3$)$_2$, (CH$_2$)$_2$N(CH$_3$)CH$_2$CH$_3$, (CH$_2$)$_3$N(CH$_3$)CH$_2$CH$_3$, (CH$_2$)$_4$N(CH$_3$)CH$_2$CH$_3$, (CH$_2$)$_2$NH(CH$_3$), (CH$_2$)$_3$NH(CH$_3$), (CH$_2$)$_4$NH(CH$_3$), (1-pyrrolinyl)(CH$_2$)$_2$—, (1-pyrrolinyl)(CH$_2$)$_3$—, (1-pyrrolinyl)(CH$_2$)$_4$—, (1-piperidyl)(CH$_2$)$_2$—, (1-piperidyl)(CH$_2$)$_3$, (1-piperidyl)(CH$_2$)$_4$, (4-morpholinyl)(CH$_2$)$_2$, (4-morpholinyl)(CH$_2$)$_3$, (4-morpholinyl)(CH$_2$)$_4$, C(O)CH$_3$, C(O)CH$_2$CH$_3$, C(O)CH$_2$CH$_2$CH$_3$, C(O)(CH$_2$)$_4$OH, C(O)CH$_2$OH, C(O)(CH$_2$)$_2$OH, C(O)(CH$_2$)$_3$OH, C(O)CH$_2$OCH$_3$, C(O)(CH$_2$)$_2$OCH$_3$, C(O)(CH$_2$)$_3$OCH$_3$, C(O)(CH$_2$)$_4$OCH$_3$, C(O)CH$_2$OCH$_2$CH$_3$, C(O)CH$_2$N(CH$_3$)$_2$, C(O)(CH$_2$)$_2$N(CH$_3$)$_2$, C(O)(CH$_2$)$_3$N(CH$_3$)$_2$, C(O)(CH$_2$)$_4$N(CH$_3$)$_2$, C(O)CH$_2$N(CH$_3$)CH$_2$CH$_3$, C(O)(CH$_2$)$_2$N(CH$_3$)CH$_2$CH$_3$, C(O)(CH$_2$)$_3$N(CH$_3$)CH$_2$CH$_3$, C(O)(CH$_2$)$_4$N(CH$_3$)CH$_2$CH$_3$, C(O)CH$_2$NHCH$_2$CH$_3$, C(O)(CH$_2$)$_2$NHCH$_2$CH$_3$, C(O)(CH$_2$)$_3$NHCH$_2$CH$_3$, C(O)CH$_2$NHCH$_3$, C(O)(CH$_2$)$_2$NHCH$_3$, C(O)(CH$_2$)$_3$NHCH$_3$, C(O)(CH$_2$)$_4$NHCH$_3$, C(O)CH$_2$NHPr, C(O)(CH$_2$)$_2$NHPr, C(O)(CH$_2$)$_3$NHPr, C(O)(CH$_2$)$_4$NHPr, C(O)CH$_2$N(CH$_3$)$_2$, C(O)(CH$_2$)$_2$N(CH$_2$CH$_3$)$_2$, C(O)(CH$_2$)$_3$N(CH$_2$CH$_3$)$_2$, C(O)(CH$_2$)$_4$N(CH$_2$CH$_3$)$_2$, (1-pyrrolinyl)CH$_2$C(O), (1-pyrrolinyl)(CH$_2$)$_2$C(O), (1-pyrrolinyl)(CH$_2$)$_3$C(O), (1-pyrrolinyl)(CH$_2$)$_4$C(O), (1-piperidyl)CH$_2$C(O), (1-piperidyl)(CH$_2$)$_2$ C(O), (1-piperidyl)(CH$_2$)$_3$C(O), (1-piperidyl)(CH$_2$)$_4$C(O), (4-morpholinyl)(CH$_2$)$_4$C(O), (4-morpholinyl)(CH$_2$)$_3$C(O), (4-morpholinyl)CH$_2$C(O), (4-morpholinyl)(CH$_2$)$_2$C(O), C(O)OCH$_3$, C(O)OCH$_2$CH$_3$, C(O)OPr, C(O)OPr-i, C(O)O(CH$_2$)$_2$OCH$_3$, C(O)O(CH$_2$)$_3$OCH$_3$, C(O)O(CH$_2$)$_4$OCH$_3$, C(O)O(CH$_2$)$_2$OCH$_2$CH$_3$, C(O)O(CH$_2$)$_2$N(CH$_3$)$_2$, C(O)O(CH$_2$)$_3$N(CH$_3$)$_2$, C(O)O(CH$_2$)$_4$N(CH$_3$)$_2$, (1-pyrrolinyl)(CH$_2$)$_2$OC(O), (1-pyrrolinyl)(CH$_2$)$_3$OC(O), (1-pyrrolinyl)(CH$_2$)$_4$OC(O), (1-piperidyl)(CH$_2$)$_2$OC(O), (1-piperidyl)(CH$_2$)$_3$OC(O), (1-piperidyl)(CH$_2$)$_4$OC(O), (4-morpholinyl)(CH$_2$)$_2$OC(O), (4-morpholinyl)(CH$_2$)$_3$OC(O), (4-morpholinyl)(CH$_2$)$_4$OC(O), CH$_2$C(O)OCH$_3$, (CH$_2$)$_2$C(O)OCH$_3$, (CH$_2$)$_3$C(O)OCH$_3$, CH$_2$C(O)OCH$_2$CH$_3$, (CH$_2$)$_2$C(O)OCH$_2$CH$_3$, or (CH$_2$)$_3$C(O)OCH$_2$CH$_3$.

The compound of formula (I) suitable for being used as medical active ingredient comprises the compounds wherein m and n each independently represent an integer from 0 to 4; and particularly 0, 1 or 2.

TABLE 1

Examples of $R^9$ and $R^{11}$ in the compound of formula (I) suitable for being used as active medical ingredient

| $R^9$ | $R^{11}$ | $R^9$ | $R^{11}$ |
|---|---|---|---|
| H | H | H | 3-Cl |
| H | 3-Br | H | 3-F |
| H | 3-CH$_3$ | H | 3-CF$_3$ |
| H | 3-alkynyl | H | 3-CN |
| H | 3-NO$_2$ | H | 3-OCH$_3$ |
| H | 3-C(O)CH$_3$ | H | 3-SO$_2$CH$_3$ |
| H | 3-S(O)CH$_3$ | H | 3-CO$_2$CH$_3$ |
| H | 3-SO$_2$NHCH$_3$ | H | 3-CO$_2$CH$_2$CH$_3$ |
| H | 3-SO$_2$N(CH$_3$)$_2$ | H | 3-CONHCH$_3$ |
| H | 3-CON(CH$_3$)$_2$ | H | 4-CON(CH$_3$)$_2$ |
| H | 3-I | H | 4-Cl |
| H | 4-Br | H | 4-F |
| H | 4-CH$_3$ | H | 4-CF$_3$ |
| H | 4-alkynyl | H | 4-CN |
| H | 4-NO$_2$ | H | 4-OCH$_3$ |
| H | 4-C(O)CH$_3$ | H | 4-SO$_2$CH$_3$ |
| H | 4-S(O)CH$_3$ | H | 4-CO$_2$CH$_3$ |
| H | 4-SO$_2$NHCH$_3$ | H | 4-CO$_2$CH$_2$CH$_3$ |
| H | 4-SO$_2$N(CH$_3$)$_2$ | H | 4-CONHCH$_3$ |
| H | 4-F-3-Br | H | 4-F-3-I |
| H | 4-F-3-CH$_3$ | H | 4-F-3-CF$_3$ |
| H | 4-F-3-alkynyl | H | 4-F-3-CN |
| H | 4-F-3-NO$_2$ | H | 4-F-3-OCH$_3$ |
| H | 4-F-3-C(O)CH$_3$ | H | 4-F-3-SO$_2$CH$_3$ |
| H | 4-F-3-S(O)CH$_3$ | H | 4-F-3-CO$_2$CH$_3$ |
| H | 4-F-3-SO$_2$NHCH$_3$ | H | 4-F-3-CO$_2$CH$_2$CH$_3$ |
| H | 4-F-3-SO$_2$N(CH$_3$)$_2$ | H | 4-F-3-CONHCH$_3$ |
| H | 4-F-3-CON(CH$_3$)$_2$ | H | 3-F-4-F |
| H | 4-F-3-Cl | | |
| CH$_3$ | H | CH$_3$ | 3-Cl |
| CH$_3$ | 3-Br | CH$_3$ | 3-F |
| CH$_3$ | 3-CH3 | CH$_3$ | 3-CF$_3$ |
| CH$_3$ | 3-alkynyl | CH$_3$ | 3-CN |
| CH$_3$ | 3-NO2 | CH$_3$ | 3-OCH$_3$ |
| CH$_3$ | 3-C(O)CH$_3$ | CH$_3$ | 3-SO$_2$CH$_3$ |
| CH$_3$ | 3-S(O)CH$_3$ | CH$_3$ | 3-CO$_2$CH$_3$ |
| CH$_3$ | 3-SO$_2$NHCH$_3$ | CH$_3$ | 3-CO$_2$CH$_2$CH$_3$ |
| CH$_3$ | 3-SO$_2$N(CH$_3$)$_2$ | CH$_3$ | 3-CONHCH$_3$ |
| CH$_3$ | 3-CON(CH$_3$)$_2$ | CH$_3$ | 4-CON(CH$_3$)$_2$ |
| CH$_3$ | 3-I | CH$_3$ | 4-Cl |
| CH$_3$ | 4-Br | CH$_3$ | 4-F |
| CH$_3$ | 4-CH$_3$ | CH$_3$ | 4-CF$_3$ |
| CH$_3$ | 4-alkynyl | CH$_3$ | 4-CN |
| CH$_3$ | 4-SO$_2$N(CH$_3$)$_2$ | CH$_3$ | 4-CONHCH$_3$ |
| CH$_3$ | 4-F-3-Br | CH$_3$ | 4-F-3-I |
| CH$_3$ | 4-F-3-CH$_3$ | CH$_3$ | 4-F-3-CF$_3$ |
| CH$_3$ | 4-F-3-alkynyl | CH$_3$ | 4-F-3-CN |
| CH$_3$ | 4-F-3-NO$_2$ | CH$_3$ | 4-F-3-OCH$_3$ |
| CH$_3$ | 4-F-3-C(O)CH$_3$ | CH$_3$ | 4-F-3-SO$_2$CH$_3$ |
| CH$_3$ | 4-F-3-S(O)CH$_3$ | CH$_3$ | 4-F-3-CO$_2$CH$_3$ |
| CH$_3$ | 4-F-3-SO$_2$NHCH$_3$ | CH$_3$ | 4-F-3-CO$_2$CH$_2$CH$_3$ |
| CH$_3$ | 4-F-3-SO$_2$N(CH$_3$)$_2$ | CH$_3$ | 4-F-3-CONHCH$_3$ |
| CH$_3$ | 4-F-3-CON(CH$_3$)$_2$ | CH$_3$ | 4-F-3-CON(CH$_3$)$_2$ |
| CH$_3$ | 4-F-3-Cl | CH$_3$ | 3-F-4-F |
| CH$_3$ | 2-SO$_2$CH$_3$ | CH$_3$ | 3-COOH |
| CH$_3$ | 4-COOH | CH$_3$ | 2-C(O)OCH$_3$ |
| CH$_3$ | 2-I | CH$_3$ | 2-Cl |
| CH$_3$ | 2-Br | CH$_3$ | 2-F |
| CH$_3$ | 2-CH$_3$ | CH$_3$ | 2-CH$_3$ |
| CH$_3$ | 2-alkynyl | CH$_3$ | 2-CN |
| CH$_3$ | 2-NO$_2$ | CH$_3$ | 2-OCH$_3$ |
| CH$_3$ | 2-C(O)CH$_3$ | Et | 3-Cl |
| Et | 3-Br | Et | 3-F |

TABLE 1-continued

Examples of $R^9$ and $R^{11}$ in the compound of formula (I) suitable for being used as active medical ingredient

| $R^9$ | $R^{11}$ | $R^9$ | $R^{11}$ |
|---|---|---|---|
| Et | 3-CH$_3$ | Et | 3-CF$_3$ |
| Et | 3-alkynyl | Et | 3-CN |
| Et | 3-NO$_2$ | Et | 3-OCH$_3$ |
| Et | 3-C(O)CH$_3$ | Et | 3-SO$_2$CH$_3$ |
| Et | 3-S(O)CH$_3$ | Et | 3-CO$_2$CH$_3$ |
| Et | 3-SO$_2$NHCH$_3$ | Et | 3-CO$_2$CH$_2$CH$_3$ |
| Et | 3-SO$_2$N(CH$_3$)$_2$ | Et | 3-CONHCH$_3$ |
| Et | 3-CON(CH$_3$)$_2$ | Et | 4-CON(CH$_3$)$_2$ |
| Et | 3-I | Et | 4-Cl |
| Et | 4-Br | Et | 4-F |
| Et | 4-CH$_3$ | Et | 4-CF$_3$ |
| Et | 4-alkynyl | Et | 4-CN |
| Et | 4-NO$_2$ | Et | 4-OCH$_3$ |
| Et | 4-C(O)CH$_3$ | Et | 4-SO$_2$CH$_3$ |
| Et | 4-S(O)CH$_3$ | Et | 4-CO$_2$CH$_3$ |
| Et | 4-SO$_2$NHCH$_3$ | Et | 4-CO$_2$CH$_2$CH$_3$ |
| Et | 4-SO$_2$N(CH$_3$)$_2$ | Et | 4-CONHCH$_3$ |
| Et | 4-F-3-Br | Et | 4-F-3-I |
| Et | 4-F-3-CH$_3$ | Et | 4-F-3-CF$_3$ |
| Et | 4-F-3-alkynyl | Et | 4-F-3-CN |
| Et | 4-F-3-NO$_2$ | Et | 4-F-3-OCH$_3$ |
| Et | 4-F-3-C(O)CH$_3$ | Et | 4-F-3-SO$_2$CH$_3$ |
| Et | 4-F-3-S(O)CH$_3$ | Et | 4-F-3-CO$_2$CH$_3$ |
| Et | 4-F-3-SO$_2$NHCH$_3$ | Et | 4-F-3-CO$_2$CH$_2$CH$_3$ |
| Et | 4-F-3-SO$_2$N(CH$_3$)$_2$ | Et | 4-F-3-CONHCH$_3$ |
| Et | 4-F-3-CON(CH$_3$)$_2$ | Et | H |
| Et | 4-F-3-Cl | Et | 3-F-4-F |
| Et | 2-SO$_2$CH$_3$ | Et | 3-COOH |
| Et | 4-COOH | Et | 2-C(O)OCH$_3$ |
| Et | 2-I | Et | 2-Cl |
| Et | 2-Br | Et | 2-F |
| Et | 2-CH$_3$ | Et | 2-CH$_3$ |
| Et | 2-alkynyl | Et | 2-CN |
| Et | 2-NO$_2$ | Et | 2-OCH$_3$ |
| Et | 2-C(O)CH$_3$ | O(CH$_2$)$_2$OMe | 3-CON(CH$_3$)$_2$ |
| O(CH$_2$)$_2$OMe | H | O(CH$_2$)$_2$OMe | 3-Cl |
| O(CH$_2$)$_2$OMe | 3-Br | O(CH$_2$)$_2$OMe | 3-F |
| O(CH$_2$)$_2$OMe | 3-CH$_3$ | O(CH$_2$)$_2$OMe | 3-CF$_3$ |
| O(CH$_2$)$_2$OMe | 3-alkynyl | O(CH$_2$)$_2$OMe | 3-CN |
| O(CH$_2$)$_2$OMe | 3-NO$_2$ | O(CH$_2$)$_2$OMe | 3-OCH$_3$ |
| O(CH$_2$)$_2$OMe | 3-C(O)CH$_3$ | O(CH$_2$)$_2$OMe | 3-SO$_2$CH$_3$ |
| O(CH$_2$)$_2$OMe | 3-S(O)CH$_3$ | O(CH$_2$)$_2$OMe | 3-CO$_2$CH$_3$ |
| O(CH$_2$)$_2$OMe | 3-SO$_2$NHCH$_3$ | O(CH$_2$)$_2$OMe | 3-CO$_2$CH$_2$CH$_3$ |
| O(CH$_2$)$_2$OMe | 3-SO$_2$N(CH$_3$)$_2$ | O(CH$_2$)$_2$OMe | 3-CONHCH$_3$ |
| O(CH$_2$)$_2$OMe | 3-I | O(CH$_2$)$_2$OMe | 4-Cl |
| O(CH$_2$)$_2$OMe | 4-Br | O(CH$_2$)$_2$OMe | 4-F |
| O(CH$_2$)$_2$OMe | 4-CH$_3$ | O(CH$_2$)$_2$OMe | 4-CF$_3$ |
| O(CH$_2$)$_2$OMe | 4-alkynyl | O(CH$_2$)$_2$OMe | 4-CN |
| O(CH$_2$)$_2$OMe | 4-NO$_2$ | O(CH$_2$)$_2$OMe | 4-OCH$_3$ |
| O(CH$_2$)$_2$OMe | 4-C(O)CH$_3$ | O(CH$_2$)$_2$OMe | 4-SO$_2$CH$_3$ |
| O(CH$_2$)$_2$OMe | 4-S(O)CH$_3$ | O(CH$_2$)$_2$OMe | 4-CO$_2$CH$_3$ |
| O(CH$_2$)$_2$OMe | 4-SO$_2$NHCH$_3$ | O(CH$_2$)$_2$OMe | 4-CO$_2$CH$_2$CH$_3$ |
| O(CH$_2$)$_2$OMe | 4-SO$_2$N(CH$_3$)$_2$ | O(CH$_2$)$_2$OMe | 4-CONHCH$_3$ |
| O(CH$_2$)$_2$OMe | 4-CON(CH$_3$) | O(CH$_2$)$_2$OMe | 4-F-3-CON(CH$_3$)$_2$ |
| O(CH$_2$)$_2$OMe | 4-F-3-Br | O(CH$_2$)$_2$OMe | 4-F-3-I |
| O(CH$_2$)$_2$OMe | 4-F-3-CH$_3$ | O(CH$_2$)$_2$OMe | 4-F-3-CF$_3$ |
| O(CH$_2$)$_2$OMe | 4-F-3-alkynyl | O(CH$_2$)$_2$OMe | 4-F-3-CN |
| O(CH$_2$)$_2$OMe | 4-F-3-NO$_2$ | O(CH$_2$)$_2$OMe | 4-F-3-OCH$_3$ |
| O(CH$_2$)$_2$OMe | 4-F-3-C(O)CH$_3$ | O(CH$_2$)$_2$OMe | 4-F-3-SO$_2$CH$_3$ |
| O(CH$_2$)$_2$OMe | 4-F-3-S(O)CH$_3$ | O(CH$_2$)$_2$OMe | 4-F-3-CO$_2$CH$_3$ |
| O(CH$_2$)$_2$OMe | 4-F-3-SO$_2$NHCH$_3$ | O(CH$_2$)$_2$OMe | 4-F-3-CO$_2$CH$_2$CH$_3$ |
| O(CH$_2$)$_2$OMe | 4-F-3-SO$_2$N(CH$_3$)$_2$ | O(CH$_2$)$_2$OMe | 4-F-3-CONHCH$_3$ |
| O(CH$_2$)$_2$OMe | 4-F-3-Cl | O(CH$_2$)$_2$OMe | 3-F-4-F |
| O(CH$_2$)$_2$OMe | 2-SO$_2$CH$_3$ | O(CH$_2$)$_2$OMe | 3-COOH |
| O(CH$_2$)$_2$OMe | 4-COOH | O(CH$_2$)$_2$OMe | 2-C(O)OCH$_3$ |
| O(CH$_2$)$_2$OMe | 2-I | O(CH$_2$)$_2$OMe | 2-Cl |
| O(CH$_2$)$_2$OMe | 2-Br | O(CH$_2$)$_2$OMe | 2-F |

TABLE 1-continued

Examples of $R^9$ and $R^{11}$ in the compound of formula (I) suitable for being used as active medical ingredient

| $R^9$ | $R^{11}$ | $R^9$ | $R^{11}$ |
|---|---|---|---|
| O(CH$_2$)$_2$OMe | 2-CH$_3$ | O(CH$_2$)$_2$OMe | 2-CH$_3$ |
| O(CH$_2$)$_2$OMe | 2-alkynyl | O(CH$_2$)$_2$OMe | 2-CN |
| O(CH$_2$)$_2$OMe | 2-NO$_2$ | O(CH$_2$)$_2$OMe | 2-OCH$_3$ |
| O(CH$_2$)$_2$OMe | 2-C(O)CH$_3$ | O(CH$_2$)$_2$OMe | 3-Cl |
| O(CH$_2$)$_2$OMe | 3-Br | O(CH$_2$)$_2$OMe | 3-F |
| O(CH$_2$)$_2$OMe | 3-CH$_3$ | O(CH$_2$)$_2$OMe | 3-CF$_3$ |
| O(CH$_2$)$_2$OMe | 3-alkynyl | O(CH$_2$)$_2$OMe | 3-CN |
| O(CH$_2$)$_2$OMe | 3-NO$_2$ | O(CH$_2$)$_2$OMe | 3-OCH$_3$ |
| O(CH$_2$)$_2$OMe | 3-C(O)CH$_3$ | O(CH$_2$)$_2$OMe | 3-SO$_2$CH$_3$ |
| O(CH$_2$)$_2$OMe | 3-S(O)CH$_3$ | O(CH$_2$)$_2$OMe | 3-CO$_2$CH$_3$ |
| O(CH$_2$)$_2$OMe | 3-SO$_2$NHCH$_3$ | O(CH$_2$)$_2$OMe | 3-CO$_2$CH$_2$CH$_3$ |
| O(CH$_2$)$_2$OMe | 3-SO$_2$N(CH$_3$)$_2$ | O(CH$_2$)$_2$OMe | 3-CONHCH$_3$ |
| O(CH$_2$)$_2$OMe | 3-CON(CH$_3$)$_2$ | O(CH$_2$)$_2$OMe | 4-CON(CH$_3$)$_2$ |
| O(CH$_2$)$_2$OMe | 3-I | O(CH$_2$)$_2$OMe | 4-Cl |
| O(CH$_2$)$_2$OMe | 4-Br | O(CH$_2$)$_2$OMe | 4-F |
| O(CH$_2$)$_2$OMe | 4-CH$_3$ | O(CH$_2$)$_2$OMe | 4-CF$_3$ |
| O(CH$_2$)$_2$OMe | 4-alkynyl | O(CH$_2$)$_2$OMe | 4-CN |
| O(CH$_2$)$_2$OMe | 4-NO$_2$ | O(CH$_2$)$_2$OMe | 4-OCH$_3$ |
| O(CH$_2$)$_2$OMe | 4-C(O)CH$_3$ | O(CH$_2$)$_2$OMe | 4-SO$_2$CH$_3$ |
| O(CH$_2$)$_2$OMe | 4-S(O)CH$_3$ | O(CH$_2$)$_2$OMe | 4-CO$_2$CH$_3$ |
| O(CH$_2$)$_2$OMe | 4-SO$_2$NHCH$_3$ | O(CH$_2$)$_2$OMe | 4-CO$_2$CH$_2$CH$_3$ |
| O(CH$_2$)$_2$OMe | 4-SO$_2$N(CH$_3$)$_2$ | O(CH$_2$)$_2$OMe | 4-CONHCH$_3$ |
| O(CH$_2$)$_2$OMe | 4-F-3-alkynyl | O(CH$_2$)$_2$OMe | 4-F-3-CN |
| O(CH$_2$)$_2$OMe | 4-F-3-Br | O(CH$_2$)$_2$OMe | 4-F-3-I |
| O(CH$_2$)$_2$OMe | 4-F-3-CH$_3$ | O(CH$_2$)$_2$OMe | 4-F-3-CF$_3$ |
| O(CH$_2$)$_2$OMe | 4-F-3-NO$_2$ | O(CH$_2$)$_2$OMe | 4-F-3-OCH$_3$ |
| O(CH$_2$)$_2$OMe | 4-F-3-C(O)CH$_3$ | O(CH$_2$)$_2$OMe | 4-F-3-SO$_2$CH$_3$ |
| O(CH$_2$)$_2$OMe | 4-F-3-S(O)CH$_3$ | O(CH$_2$)$_2$OMe | 4-F-3-CO$_2$CH$_3$ |
| O(CH$_2$)$_2$OMe | 4-F-3-SO$_2$NHCH$_3$ | O(CH$_2$)$_2$OMe | 4-F-3-CO$_2$CH$_2$CH$_3$ |
| O(CH$_2$)$_2$OMe | 4-F-3-SO$_2$N(CH$_3$)$_2$ | O(CH$_2$)$_2$OMe | 4-F-3-CONHCH$_3$ |
| O(CH$_2$)$_2$OMe | 4-F-3-CON(CH$_3$)$_2$ | O(CH$_2$)$_2$OMe | 4-F-3-Cl |
| O(CH$_2$)$_2$OMe | 3-F-4-F | O(CH$_2$)$_2$OMe | 2-SO$_2$CH$_3$ |
| O(CH$_2$)$_2$OMe | H | O(CH$_2$)$_2$OMe | 3-COOH |
| O(CH$_2$)$_2$OMe | 4-COOH | O(CH$_2$)$_2$OMe | 2-C(O)OCH$_3$ |
| O(CH$_2$)$_2$OMe | 2-I | O(CH$_2$)$_2$OMe | 2-Cl |
| O(CH$_2$)$_2$OMe | 2-Br | O(CH$_2$)$_2$OMe | 2-F |
| O(CH$_2$)$_2$OMe | 2-CH$_3$ | O(CH$_2$)$_2$OMe | 2-CF$_3$ |
| O(CH$_2$)$_2$OMe | 2-alkynyl | O(CH$_2$)$_2$OMe | 2-CN |
| O(CH$_2$)$_2$OMe | 2-NO$_2$ | O(CH$_2$)$_2$OMe | 2-OCH$_3$ |
| O(CH$_2$)$_2$OMe | 2-C(O)CH$_3$ | O(CH$_2$)$_2$OH | 3-I |
| O(CH$_2$)$_2$OH | H | O(CH$_2$)$_2$OH | 3-Cl |
| O(CH$_2$)$_2$OH | 3-Br | O(CH$_2$)$_2$OH | 3-F |
| O(CH$_2$)$_2$OH | 3-CH$_3$ | O(CH$_2$)$_2$OH | 3-CF$_3$ |
| O(CH$_2$)$_2$OH | 3-alkynyl | O(CH$_2$)$_2$OH | 3-CN |
| O(CH$_2$)$_2$OH | 3-NO$_2$ | O(CH$_2$)$_2$OH | 3-OCH$_3$ |
| O(CH$_2$)$_2$OH | 3-C(O)CH$_3$ | O(CH$_2$)$_2$OH | 3-CO$_2$CH$_3$ |
| O(CH$_2$)$_2$OH | 3-S(O)CH$_3$ | O(CH$_2$)$_2$OH | 3-CO$_2$CH$_2$CH$_3$ |
| O(CH$_2$)$_2$OH | 3-SO$_2$CH$_3$ | O(CH$_2$)$_2$OH | 3-CONHCH$_3$ |
| O(CH$_2$)$_2$OH | 3-SO$_2$NHCH$_3$ | O(CH$_2$)$_2$OH | 4-CON(CH$_3$)$_2$ |
| O(CH$_2$)$_2$OH | 3-SO$_2$N(CH$_3$)$_2$ | O(CH$_2$)$_2$OH | 4-Cl |
| O(CH$_2$)$_2$OH | 3-CON(CH$_3$)$_2$ | O(CH$_2$)$_2$OH | 4-F |
| O(CH$_2$)$_2$OH | 4-Br | O(CH$_2$)$_2$OH | 4-CF$_3$ |
| O(CH$_2$)$_2$OH | 4-CH$_3$ | O(CH$_2$)$_2$OH | 4-CN |
| O(CH$_2$)$_2$OH | 4-alkynyl | O(CH$_2$)$_2$OH | 4-OCH$_3$ |
| O(CH$_2$)$_2$OH | 4-NO$_2$ | O(CH$_2$)$_2$OH | 4-SO$_2$CH$_3$ |
| O(CH$_2$)$_2$OH | 4-C(O)CH$_3$ | O(CH$_2$)$_2$OH | 4-CO$_2$CH$_3$ |
| O(CH$_2$)$_2$OH | 4-S(O)CH$_3$ | O(CH$_2$)$_2$OH | 4-CO$_2$CH$_2$CH$_3$ |
| O(CH$_2$)$_2$OH | 4-SO$_2$NHCH$_3$ | O(CH$_2$)$_2$OH | 4-CONHCH$_3$ |
| O(CH$_2$)$_2$OH | 4-SO$_2$N(CH$_3$)$_2$ | O(CH$_2$)$_2$OH | 4-F-3-CON(CH$_3$)$_2$ |
| O(CH$_2$)$_2$OH | 4-CON(CH$_3$)$_2$ | O(CH$_2$)$_2$OH | 4-F-3-I |
| O(CH$_2$)$_2$OH | 4-F-3-Br | O(CH$_2$)$_2$OH | 4-F-3-CF$_3$ |
| O(CH$_2$)$_2$OH | 4-F-3-CH$_3$ | O(CH$_2$)$_2$OH | 4-F-3-CN |
| O(CH$_2$)$_2$OH | 4-F-3-alkynyl | O(CH$_2$)$_2$OH | 4-F-3-OCH$_3$ |
| O(CH$_2$)$_2$OH | 4-F-3-NO$_2$ | O(CH$_2$)$_2$OH | 4-F-3-SO$_2$CH$_3$ |
| O(CH$_2$)$_2$OH | 4-F-3-C(O)CH$_3$ | O(CH$_2$)$_2$OH | 4-F-3-CO$_2$CH$_2$CH$_3$ |
| O(CH$_2$)$_2$OH | 4-F-3-SO$_2$NHCH$_3$ | O(CH$_2$)$_2$OH | 4-F-3-CONHCH$_3$ |
| O(CH$_2$)$_2$OH | 4-F-3-SO$_2$N(CH$_3$)$_2$ | | |
| O(CH$_2$)$_2$OH | 4-F-3-Cl | O(CH$_2$)$_2$OH | 3-F-4-F |
| O(CH$_2$)$_2$OH | H | O(CH$_2$)$_2$OH | 3-COOH |
| O(CH$_2$)$_2$OH | 4-COOH | O(CH$_2$)$_2$OH | 2-C(O)OCH$_3$ |
| O(CH$_2$)$_2$OH | 2-I | O(CH$_2$)$_2$OH | 2-Cl |
| O(CH$_2$)$_2$OH | 2-Br | O(CH$_2$)$_2$OH | 2-F |
| O(CH$_2$)$_2$OH | 2-CH$_3$ | O(CH$_2$)$_2$OH | 2-CH$_3$ |
| O(CH$_2$)$_2$OH | 2-alkynyl | O(CH$_2$)$_2$OH | 2-CN |
| O(CH$_2$)$_2$OH | 2-NO$_2$ | O(CH$_2$)$_2$OH | 2-OCH$_3$ |
| O(CH$_2$)$_2$OH | 2-C(O)CH$_3$ | O(CH$_2$)$_2$OH | 2-SO$_2$CH$_3$ |
| CH$_3$ | 4-NO$_2$ | CH$_3$ | 4-OCH$_3$ |
| CH$_3$ | 4-C(O)CH$_3$ | CH$_3$ | 4-SO$_2$CH$_3$ |
| CH$_3$ | 4-S(O)CH$_3$ | CH$_3$ | 4-CO$_2$CH$_3$ |
| CH$_3$ | 4-SO$_2$NHCH$_3$ | CH$_3$ | 4-CO$_2$CH$_2$CH$_3$ |

TABLE 2

Examples of $R^5$ in the compound of formula (I) suitable for being used as medical active ingredient

| $R^5$ | $R^5$ | $R^5$ | $R^5$ |
|---|---|---|---|
| F | OH | OCH$_3$ | OCH$_2$CH$_3$ |
| O(CH$_2$)$_2$OMe | O(CH$_2$)$_3$OMe | O(CH$_2$)$_2$OH | OPr-n |
| OPr-i | O(CH$_2$)$_3$OH | O(CH$_2$)$_4$OMe | OBu-n |
| O(CH$_2$)$_3$NMe$_2$ | O(CH$_2$)$_2$NMe$_2$ | O(CH$_2$)$_3$NEt$_2$ | O(CH$_2$)$_2$NEt$_2$ |
| O(CH$_2$)$_3$(1-morpholinyl) | O(CH$_2$)$_3$(1-pyrrolinyl) | O(CH$_2$)$_2$(1-morpholinyl) | O(CH$_2$)$_2$(1-pyrrolinyl) |
| O(CH$_2$)$_3$(1-imidazolyl) | O(CH$_2$)$_3$(1-piperidyl) | O(CH$_2$)$_2$(1-imidazolyl) | O(CH$_2$)$_2$(1-imidazolyl) |
| O(CH$_2$)$_4$(1-morpholinyl) | O(CH$_2$)$_4$(1-pyrrolyl) | O(CH$_2$)$_4$(1-imidazolyl) | H |
| O(CH$_2$)$_4$(1-piperidyl) | CH$_3$ | NMe$_2$ | NHC(O)Me |
| N(Me)C(O)Me | OCF$_3$ | OCF$_2$CH$_3$ | |

The invention further relates to a pharmaceutical preparation comprising a pharmaceutically acceptable excipient and a compound of formula (I),

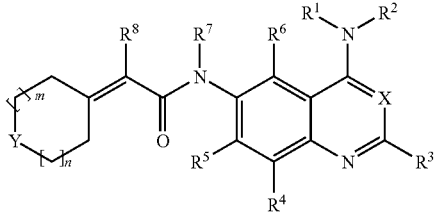

wherein X represents N, C—CN or CH; Y represents $CH_2$, S, O or N—$R^9$; $R^1$, $R^3$, $R^7$ and $R^8$ independently represent H, $CF_3$, or $C_{1-6}$alkyl; $R^2$ represents a group selected from formula (II), (III), (IV), (V), (VI), (VII) or (VIII);

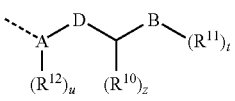

(II)

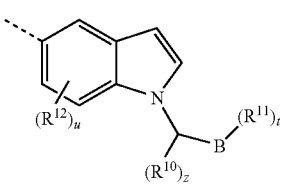

(III)

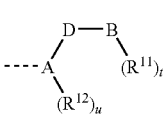

(IV)

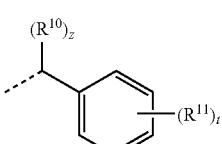

(V)

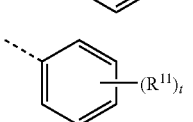

(VI)

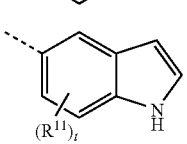

(VII)

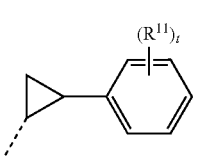

(VIII)

$R^4$ and $R^6$ independently represent H, $C_{1-6}$alkyl, $OC_{1-6}$alkyl, OH, F, Cl, Br, $OCF_3$, or trifluoromethyl; $R^5$ is independently at each occurrence selected from H, F, $C_{1-6}$alkyl, OH, $OC_{1-6}$alkyl, $OCF_3$, $O(CH_2)_{2-4}OCF_3$, $OCF_2CH_3$, $NH_2$, $NH(C_{1-6}$alkyl), $N(C_{1-6}$alkyl$)_2$, 1-pyrrolinyl, 1-piperidyl, 4-morpholinyl, F, Cl, Br, trifluoromethyl, $O(CH_2)_{2-4}OC_{1-6}$alkyl, $O(CH_2)_{2-4}NH(C_{1-6}$alkyl), $O(CH_2)_{2-4}N(C_{1-6}$alkyl$)_2$, (1-pyrrolinyl)$(CH_2)_{2-4}O$, (1-piperidyl)$(CH_2)_{2-4}O$, (4-morpholinyl)$(CH_2)_{2-4}O$, NHC(O)H, NHC(O)($C_{1-6}$alkyl), $N(C_{1-6}$alkyl)C(O)($C_{1-6}$alkyl), $O(CH_2)_{2-4}OH$, $N(C_{1-6}$alkyl)C(O)O($C_{1-6}$alkyl), $N(C_{1-6}$alkyl)C(O)OH, NHC(O)O($C_{1-6}$alkyl), OC(O)NH($C_{1-6}$alkyl), OC(O)N($C_{1-6}$alkyl$)_2$, (1-piperidyl)$(CH_2)_{2-4}OC(O)$, (4-morpholinyl)$(CH_2)_{2-4}OC(O)$, (1-pyrrolinyl)$(CH_2)_2OC(O)$, (1-imidazolyl)$(CH_2)_{2-4}O$, (4-imidazolyl)$(CH_2)_{2-4}OC(O)$, (pyrazolyl)$(CH_2)_{2-4}O$, (triazolyl)$(CH_2)_{2-4}OC(O)$, or Ar$(CH_2)_{1-4}O$; $R^9$ is independently at each occurrence selected from H, $C_{1-6}$alkyl, $CF_3$, $CF_2CH_3$, $(CH_2)_2OH$, $(CH_2)_{1-4}OC_{1-6}$alkyl, $(CH_2)_{1-4}NH(C_{1-6}$alkyl), $(CH_2)_{1-4}N(C_{1-6}$ alkyl$)_2$, (1-pyrrolinyl)$(CH_2)_{1-4}$, (1-piperidyl)$(CH_2)_{1-4}$, (4-morpholinyl)$(CH_2)_{1-4}$, $C(O)C_{1-6}$alkyl, $C(O)(CH_2)_{1-4}OH$, $C(O)(CH_2)_{1-4}OC_{1-6}$alkyl, $C(O)(CH_2)_{1-4}N(C_{1-6}$alkyl$)_2$, (1-pyrrolinyl)$(CH_2)_{1-6}C(O)$, (1-piperidyl)$(CH_2)_{1-6}C(O)$, (4-morpholinyl)$(CH_2)_{1-4}C(O)$, $C(O)OC_{1-6}$alkyl, $C(O)O(CH_2)_{2-4}OC_{1-6}$alkyl, $C(O)O(CH_2)_{2-4}N(C_{1-6}$alkyl$)_2$, $C(O)O(CH_2)_{2-4}NH(C_{1-6}$alkyl), (1-pyrrolinyl)$(CH_2)_{2-4}OC(O)$, (1-piperidyl)$(CH_2)_{2-4}OC(O)$, (4-morpholinyl)$(CH_2)_{2-4}OC(O)$, $(CH_2)_{1-4}C(O)OC_{1-6}$alkyl, or Ar$(CH_2)_{1-4}$; $R^{10}$ represents $C_{1-6}$ alkyl, or F; $R^{11}$ and $R^{12}$ represent independently at each occurrence F, Cl, Br, I, CN, $NO_2$, $CF_3$, OH, $NH_2$, $C_{1-1}$ alkyl, $OC_{1-4}$ alkyl, $OCF_3$, $OCF_2CH_3$, $NH(C_{1-4}$ alkyl), $N(C_{1-4}$ alkyl$)_2$, $OC(O)C_{1-4}$ alkyl, NHC(O)H, NHC(O)$C_{1-4}$ alkyl, $N(C_{1-4}$ alkyl)C(O)$C_{1-4}$ alkyl, $C(O)OC_{1-4}$ alkyl, $C(O)NHC_{1-4}$ alkyl, $C(O)N(C_{1-4}$ alkyl$)_2$, COOH, $C(O)C_{1-4}$ alkyl, $S(O)C_{1-4}$ alkyl, $SO_2C_{1-4}$ alkyl, $SO_2NHC_{1-4}$ alkyl, or $SO_2N(C_{1-4}$ alkyl$)_2$; A, B independently represent aromatic ring; Ar is phenyl, substituted phenyl or pyridyl; D represents O, S, NH, or methylene; m and n independently represent an integer from 0 to 4; z is 0, 1, or 2, and t and u independently represent an integer from 0 to 4.

The pharmaceutical preparation is formulated for a mode of administration selected from oral, intravenous, intraperitoneal, subcutaneous, intramuscular, nasal, ocular, pulmonary, anal, vaginal, or epidermal.

In other embodiments, this invention relates to treating or preventing physiological disorder caused by EGFR or Her-2 over expression in mammals comprising administering a compound or a preparation of the invention described herein, the disorder including but not limited to breast cancer, kidney cancer, bladder cancer, oral cancer, laryngeal cancer, esophageal cancer, gastric cancer, colorectal cancer, ovarian cancer, lung cancer, or head and neck cancer. In addition, the application relates to treating or preventing a physiological disorder by inhibiting EGFR-TK activity in mammals, the disorder including but not limited to psoriasis, pneumonia, hepatitis, nephritis, pancreatitis, or diabetes.

In other aspects of the invention provided is a method for preparing a compound of formula (I),

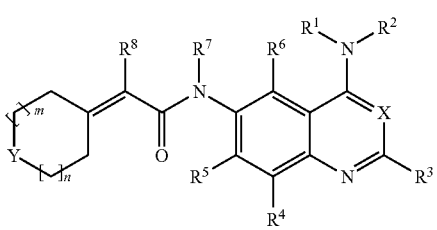

(I)

wherein X represents N, C—CN or CH; Y represents $CH_2$, S, O or N—$R^9$; $R^1$, $R^3$, $R^7$ and $R^8$ independently represent H, $CF_3$, or $C_{1-6}$alkyl; $R^2$ represents a group selected from formula (II), (III), (IV), (V), (VI), (VII) or (VIII);

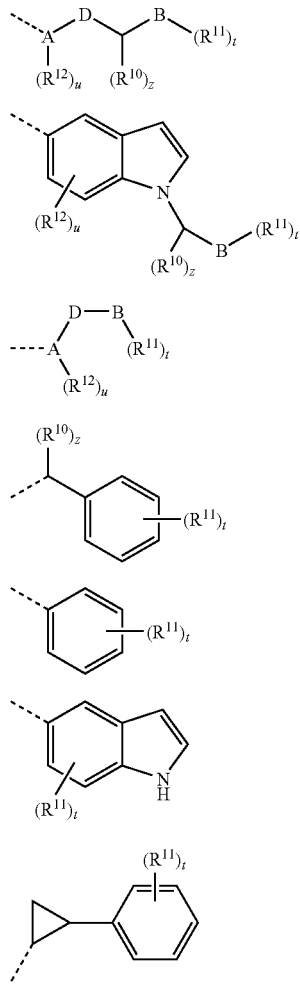

$R^4$ and $R^6$ independently represent H, $C_{1-6}$alkyl, $OC_{1-6}$alkyl, OH, F, Cl, Br, $OCF_3$, or trifluoromethyl; $R^5$ is independently at each occurrence selected from H, F, $C_{1-6}$alkyl, OH, $OC_{1-6}$ alkyl, $OCF_3$, $O(CH_2)_{2-4}OCF_3$, $OCF_2CH_3$, $NH_2$, $NH(C_{1-6}$ alkyl), $N(C_{1-6}$alkyl$)_2$, 1-pyrrolinyl, 1-piperidyl, 4-morpholinyl, F, Cl, Br, trifluoromethyl, $O(CH_2)_{2-4}OC_{1-6}$alkyl, $O(CH_2)_{2-4}NH(C_{1-6}$alkyl), $O(CH_2)_{2-4}N(C_{1-6}$alkyl$)_2$, (1-pyrrolinyl)$(CH_2)_{2-4}O$, (1-piperidyl)$(CH_2)_{2-4}O$, (4-morpholinyl)$(CH_2)_{2-4}O$, NHC(O)H, NHC(O)($C_{1-6}$alkyl), $N(C_{1-6}$alkyl)C(O)($C_{1-6}$alkyl), $O(CH_2)_{2-4}OH$, $N(C_{1-6}$alkyl)C(O)O($C_{1-6}$ alkyl), $N(C_{1-6}$alkyl)C(O)OH, NHC(O)O($C_{1-6}$alkyl), OC(O)$NH(C_{1-6}$alkyl), OC(O)N($C_{1-6}$alkyl$)_2$, (1-piperidyl)$(CH_2)_{2-4}$OC(O), (4-morpholinyl)$(CH_2)_{2-4}$OC(O), (1-pyrrolinyl)$(CH_2)_{2-4}$OC(O), (1-imidazolyl)$(CH_2)_{2-4}O$, (4-imidazolyl)$(CH_2)_{2-4}$OC(O), (pyrazolyl)$(CH_2)_{2-4}O$, (triazolyl)$(CH_2)_{2-4}$OC(O), or $Ar(CH_2)_{1-4}O$; $R^9$ is independently at each occurrence selected from H, $C_{1-6}$alkyl, $CF_3$, $CF_2CH_3$, $(CH_2)_{2-4}OH$, $(CH_2)_{1-4}OC_{1-6}$alkyl, $(CH_2)_{1-4}NH(C_{1-6}$alkyl), $(CH_2)_{1-4}N(C_{1-6}$ alkyl$)_2$, (1-pyrrolinyl)$(CH_2)_{1-4}$, (1-piperidyl)$(CH_2)_{1-4}$, (4-morpholinyl)$(CH_2)_{1-4}$, C(O)$C_{1-6}$alkyl, C(O)$(CH_2)_{1-4}$OH, C(O)$(CH_2)_{1-4}$O$C_{1-6}$alkyl, C(O)$(CH_2)_{1-4}N(C_{1-6}$alkyl$)_2$, (1-pyrrolinyl)$(CH_2)_{1-6}$C(O), (1-piperidyl)$(CH_2)_{1-6}$C(O), (4-morpholinyl)$(CH_2)_{1-4}$C(O), C(O)O$C_{1-6}$alkyl, C(O)O $(CH_2)_{2-4}OC_{1-6}$alkyl, $C(O)O(CH_2)_{2-4}N(C_{1-6}$alkyl$)_2$, C(O)O$(CH_2)_{2-4}NH(C_{1-6}$alkyl), (1-pyrrolinyl)$(CH_2)_{2-4}$OC(O), (1-piperidyl)$(CH_2)_{2-4}$OC(O), (4-morpholinyl)$(CH_2)_{2-4}$OC(O), $(CH_2)_{1-4}$C(O)O$C_{1-6}$alkyl, or $Ar(CH_2)_{1-4}$; $R^{10}$ represents $C_{1-6}$ alkyl, or F; $R^{11}$ and $R^{12}$ represent independently at each occurrence F, Cl, Br, I, CN, $NO_2$, $CF_3$, OH$NH_2$, $C_{1-4}$ alkyl, $OC_{1-4}$ alkyl, $OCF_3$, $OCF_2CH_3$, $NH(C_{1-4}$ alkyl), $N(C_{1-4}$ alkyl$)_2$, OC(O)$C_{1-4}$ alkyl, NHC(O)H, NHC(O)$C_{1-4}$ alkyl, $N(C_{1-4}$ alkyl)C(O)$C_{1-4}$ alkyl, C(O)O$C_{1-4}$ alkyl, C(O)NH$C_{1-4}$ alkyl, C(O)N($C_{1-4}$ alkyl), COOH, C(O)$C_{1-4}$ alkyl, S(O)$C_{1-4}$ alkyl, $SO_2C_{1-4}$ alkyl, $SO_2NHC_{1-4}$ alkyl, or $SO_2N(C_{1-4}$ alkyl); A, B independently represent aromatic ring; Ar is phenyl, substituted phenyl or pyridyl; D represents O, S, NH, or methylene; m and n independently represent an integer from 0 to 4; z is 0, 1, or 2, and t and u independently represent an integer from 0 to 4; the method comprising the steps of:

1) contacting a compound of formula (XI)

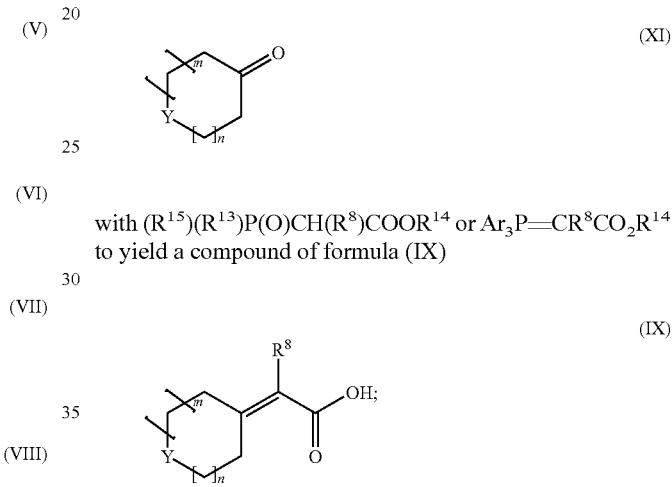

with $(R^{15})(R^{13})P(O)CH(R^8)COOR^{14}$ or $Ar_3P=CR^8CO_2R^{14}$ to yield a compound of formula (IX)

wherein Y represents $CH_2$, S, O, or N—$R^9$ except NH; $R^8$ independently represent H, $CF_3$, or $C_{1-6}$alkyl; $R^9$ is independently at each occurrence selected from $C_{1-6}$alkyl, $CF_3$, $CF_2CH_3$, $(CH_2)_{2-4}OH$, $(CH_2)_{1-4}OC_{1-6}$alkyl, $(CH_2)_{1-4}NH$ ($C_{1-6}$alkyl), $(CH_2)_{1-4}N(C_{1-6}$alkyl$)_2$, (1-pyrrolinyl)$(CH_2)_{1-4}$, (1-piperidyl)$(CH_2)_{1-4}$, (4-morpholinyl)$(CH_2)_{1-4}$, C(O)$C_{1-6}$ alkyl, C(O)$(CH_2)_{1-4}OH$, C(O)$(CH_2)_{1-4}OC_{1-6}$alkyl, C(O)$(CH_2)_{1-4}N(C_{1-6}$alkyl$)_2$, (1-pyrrolinyl)$(CH_2)_{1-6}$C(O), (1-piperidyl)$(CH_2)_{1-6}$C(O), (4-morpholinyl)$(CH_2)_{1-4}$C(O), C(O)$OC_{1-6}$alkyl, $C(O)O(CH_2)_{2-4}OC_{1-6}$alkyl, $C(O)O(CH_2)_{2-4}N$($C_{1-6}$alkyl$)_2$, (1-pyrrolinyl)$(CH_2)_{2-4}$OC(O), (1-piperidyl)$(CH_2)_{2-4}$OC(O), (4-morpholinyl)$(CH_2)_{2}$OC(O), $(CH_2)_{1-4}$C(O)O$C_{1-6}$alkyl, or $Ar(CH_2)_{1-4}$; $R^{13}$ and $R^{15}$ are independently $C_{1-4}$alkyl, $OC_{1-4}$alkyl, phenyl, substituted phenyl, phenoxy, or substituted phenoxy; $R^{14}$ represents $C_{1-5}$alkyl; Ar is phenyl or substituted phenyl; and m and n independently represent an integer from 0 to 4.

2) the compound of formula (IX) can be firstly transformed into active ester, acyl chloride, acyl imidazole or mixed anhydride and then contacted with the compound of formula (X) to yield a compound of formula (I), wherein $R^1$, $R^2$, $R^3$, $R^4$, $R^5$, $R^6$, $R^7$, $R^8$, $R^{10}$, $R^{11}$, $R^{12}$, A, B, D, Ar, m, n, z, t, and u are as in claim 1; Y represents N—$R^9$, and $R^9$ is not H. And tertiary amines, such as triethylamine, N-methylmorpholine, trimethylamine, pyridine or substituted pyridine can be used to accelerate the reaction. When the compound of formula (IX) is transformed into acyl chloride, thionyl chloride, phosphorus trichloride, phosphorus pentachloride, phosphorus oxychloride, oxalyl chloride, or cyanuric chloride can be used as chlorinating agents.

Optionally, the compound of formula (IX) can be firstly transformed into anhydride and then contacted with the compound of formula (X), and pyridine or substituted pyridine such as DMAP can be used as catalyst to accelerate the reaction.

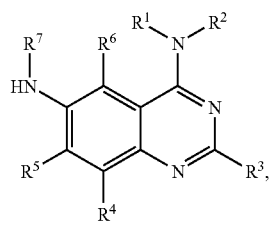

(X)

3) transforming the compound of formula (I), wherein $R^1$, $R^2$, $R^3$, $R^4$, $R^5$, $R^6$, $R^7$, $R^8$, $R^{10}$, $R^{11}$, $R^{12}$, A, B, D, Ar, m, n, z, t, and u are as in claim 1; Y represents N—$R^9$; and $R^9$ represents $(CH_3)_3OC(O)$; obtained in step 2) in acidic or pyrolytic conditions into the compound of formula (XII)

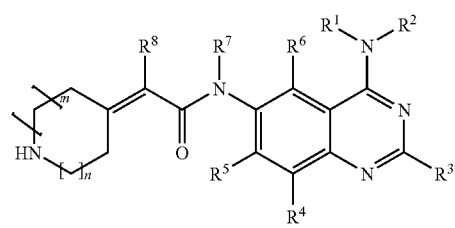

(XII)

$R^1$, $R^2$, $R^3$, $R^4$, $R^5$, $R^6$, $R^7$, $R^8$, $R^{10}$, $R^{11}$, $R^{12}$, A, B, D, X, Ar, m, n, z, t, and u are as defined in claim 1;

Acidic condition can be achieved by the use of trifluoroacetate acid, hydrochloric acid, sulfonic acid or an acetyl chloride-alcohol system.

4) contacting the compound of formula (XII) as defined in step 3) with $R^9$-LG to obtain the compound of formula (I), wherein $R^1$, $R^2$, $R^3$, $R^4$, $R^5$, $R^6$, $R^7$, $R^8$, $R^9$, $R^{10}$, $R^{11}$, $R^{12}$, A, B, D, X, Y, Ar, m, n, z, t, and u are as defined in claim 1, and LG represents Cl, Br, I, OMs, or OTs.

In step 4, organic base such as triethylamine, trimethylamine, pyridine, substituted pyridine or inorganic base such as sodium carbonate, potassium carbonate can be used to accelerate the reaction, and solvent suitable for the reaction comprises acetonitrile, dimethylformamide, dimethylacetamide, tetrahydrofuran, or ethylene glycol dimethyl ether.

The present invention teaches an irreversible EGF receptor tyrosine kinase inhibitor featuring a unique chemical structure and low reactivity-high inhibitory activity against EGF receptor tyrosine kinase. In one embodiment of the invention, the compound exhibits good inhibitory activity against A431 cell self-phosphorylation stimulated by EGF, and exhibits a certain growth inhibitory activity against the cell strain, and has a good anti-tumor effect in A431 tumor animal pathological model.

DETAILED DESCRIPTION OF THE INVENTION

Inhibition Experiment of Cellular Epidermal Growth Factor Receptor Tyrosine Kinase (EGFR-TK)

1) A431 cells were cultured in a medium which was prepared by adding 10% FCS into another medium comprising 50% DMEM and 50% F12.

2) A431 cells grown in six-well plates were cultured in a serum-free medium for 24 hours. During the 24 hour period the medium was replenished once after 12 hours.

3) A solution containing a compound to be assessed was added the A431 cells and the cells were cultured for 2 hours, supplemented twice by a medium free of the compound, and then EGF (100 ng/well) was added, and cultured for 5 minutes.

4) A431 cell homogenate was prepared by Laemili buffer which comprised 2% sodium dodecyl sulfonate (SDS), 5% 2-mercaptoethanol, 10% glycerol and 5 mM Tris; the pH value was 6.8.

5) The A431 cell homogenate was heated for 5 minutes at 100° C.

6) Proteins in the A431 cell homogenates were separated by PAGE and transferred onto a nitrocellulose membrane, and an infrared reading was obtained.

7) Calculation of percent inhibition:

% inhibition=100−[reading by infrared reader (sample)/reading by infrared reader (blank)]×100

Partial one-time measurement results for a single concentration are listed in Table 3 (preliminary selection). $EC_{50}$ measurement results of representative compounds are listed in Table 4.

TABLE 3

Inhibitory activity (percent inhibition) of representative compounds with concentration of 3 μM against A431 cells EGFR-TK phosphorylation stimulated by EGF

| Compound | Inhibition percent(%) | Compound | Inhibition percent(%) | Compound | Inhibition percent(%) |
|---|---|---|---|---|---|
| Example 1 | NA | Example 3 | 85 | Example 4 | 78 |
| Example 5 | 73 | Example 6 | 24 | Example 7 | 65 |
| Example 8 | NA | Example 30 | 55 | Example 31 | 33 |
| Example 32 | 87 | Example 33 | 94 | Example 34 | 68 |
| Example 35 | 23 | Example 36 | 57 | Example 37 | 82 |
| Example 38 | 94 | Example 40 | 89 | Example 41 | 71 |
| Example 43 | 91 | Example 50 | 95 | Example 51 | 94 |
| Example 72 | 97 | Example 73 | 82 | Example 105 | 44 |
| Example 107 | 52 | Example 110 | 59 | Example 118 | 41 |
| Example 132 | 64 | Example 134 | 59 | Example 141 | 91 |
| Example 143 | 96 | Example 144 | 89 | Example 150 | 46 |

Note:
NA = No activity

TABLE 4

Inhibitory activity (EC$_{50}$) of representative compounds against
A431 cells EGFR-TK phosphorylation stimulated by EGF

| Compound | EC$_{50}$ (μM) | Compound | EC$_{50}$ (μM) | Compound | EC$_{50}$ (μM) |
|---|---|---|---|---|---|
| Example 3 | 0.15 | Example 4 | 0.58 | Example 7 | 0.4 |
| Example 32 | 0.09 | Example 33 | 0.038 | Example 34 | 0.76 |
| Example 36 | 0.98 | Example 41 | 0.30 | Example 65 | 0.23 |
| Example 82 | 0.013 | Example 83 | 13 | Example 110 | 0.9 |
| Example 141 | 0.28 | Example 143 | 0.16 | | |

Irreversible Inhibition of Cellular Epidermal Growth Factor Receptor Tyrosine Kinase (EGFR-TK)

1) A431 cells were cultured in a medium prepared by adding 10% FCS into another medium comprising 50% DMEM and 50% F12.

2) The A431 cells grown in six-well plates were cultured in a serum-free medium for 24 hours, during the period the medium was replenished once after 12 hours.

3) A solution containing a compound to be assessed was added to the A431 cells and cultured for 2 hours, supplemented twice by a medium free of the compound, and then EGF (100 ng/well) was added, and cultured for 5 minutes.

4) A431 cell homogenate was prepared by Laemili buffer which comprised 2% sodium dodecyl sulfonate (SDS), 5% 2-mercaptoethanol, 10% glycerol and 5 mM Tris; the pH value is 6.8.

5) The A431 cell homogenate was heated for 5 minutes at 100° C.

6) Proteins in the A431 cell homogenates were separated by PAGE, transferred onto a nitrocellulose membrane, and an infrared reading was obtained.

7) Calculation of percent inhibition:

$$\% \text{ inhibition} = 100 - \left[\frac{\text{reading by infrared reader (medicine)}}{\text{reading by infrared reader (blank)}}\right] \times 100$$

8) Calculation of percent recovery:

% recovery=100−% inhibition

Parts of the results are listed in Table 5.

TABLE 5

Activity of representative compounds against A431
cells EGFR-TK phosphorylation stimulated by EGF

| Compound | EC$_{50}$ (μM) | Inhibition percent (%) | Recovery percent (%) | Activity |
|---|---|---|---|---|
| Example 32 | 0.09 | 78 | 22 | Irreversible inhibitor |
| Example 33 | 0.038 | 89 | 11 | Irreversible inhibitor |
| Example 82 | 0.013 | 14 | 86 | Reversible inhibitor |

Following literature procedure, inhibitory activity of representative compounds against BT474 cells Her-2 receptor TK phosphorylation stimulated by Her-2 was measured, and partial results are listed in Table 6.

TABLE 6

Inhibitory activity of representative compounds against BT474
cells Her-2 receptor TK phosphorylation stimulated by Her-2

| Compound | EC$_{50}$ (μM) | Compound | EC$_{50}$ (μM) | Compound | EC$_{50}$ (μM) |
|---|---|---|---|---|---|
| Example 43 | 0.35 | Example 72 | 0.82 | Example 73 | 1.7 |
| Example 105 | 0.48 | Example 108 | 0.18 | Example 150 | 0.26 |

Cell Growth Inhibition Assay (MTS Assay)

1. Cell Strain and Reagents

A431: human epithelial adenocarcinoma cell strain; LoVo: human colorectal cancer cell strain; BT474: breast cancer; SK-Br-3: breast cancer; SIT solution (SIGMA); RPMI1640 culture solution; phosphoric acid buffer; Dimethyl Sulphoxide (DMSO); MTS solution (Promega), 96 well cell culture plate, representative anti-cancer compounds.

2. Measurement

The above-mentioned cells were cultured for several days (RPMI 1640, 10% of bovine serum), collected and suspended in RPMI1640-SIT serum-free medium, placed into a 96-well cell culture plate with each well containing 20,000 cells/100 μL. The cells were cultured overnight under the condition of 5% CO$_2$ and 37° C. The next day, representative anti-cancer compounds (between 3 and 10 mM) were dissolved by dimethyl sulphoxide (DMSO) as a mother solution. Adriamycin was used as positive-control. DMSO was used as negative control. According to experimental design, the mother solution was diluted and added to the 96 well cell culture plate, cultured for 48 hours under the condition of 5% CO$_2$ and 37° C. Subsequently, 20 μL of MTS solution was added to each well of the 96 well cell culture plate and cultured for another 2 to 4 hours under the condition of 5% CO$_2$ and 37° C. Absorbance was read at 490 nm wavelength, and converted into cell survival rate.

Calculation of Percent Inhibition:

% inhibition=100−[reading of infrared reader (medicine)/reading of infrared reader (blank)]×100

For each concentration, there two measurements were taken and the average was obtained. Partial results are listed in Tables 7, 8 and 9.

TABLE 7

Growth inhibition activity (EC$_{50}$) of representative
compounds against A431 cells

| Compound | EC$_{50}$ (μM) | Compound | EC$_{50}$ (μM) | Compound | EC$_{50}$ (μM) |
|---|---|---|---|---|---|
| Example 3 | 2 | Example 4 | 1.8 | Example 7 | 5 |
| Example 32 | 0.6 | Example 33 | 0.10 | Example 34 | 13 |
| Example 36 | 30 | Example 38 | 0.014 | Example 41 | 1.5 |
| Example 42 | 0.12 | Example 43 | 0.11 | Example 50 | 0.15 |
| Example 51 | 0.12 | Example 72 | 0.09 | Example 73 | 0.63 |
| Example 82 | 0.30 | Example 83 | 35 | Example 108 | 3.0 |
| Example 118 | 1.9 | Example 134 | 0.9 | Example 143 | 0.25 |
| Example 154 | 0.11 | Tarceva | 0.45 | Lapatinib | 1.19 |

TABLE 8

Growth inhibition activity (EC$_{50}$) (in μM) of representative compounds against BT474 and SK-Br-3 cells

| Compound | BT474 | SK-Br-3 |
|---|---|---|
| Example 43 | 0.61 | 0.52 |
| Example 72 | 1.31 | 0.80 |
| Example 73 | 21.48 | 2.31 |
| Example 108 | 1.57 | 0.53 |
| Lapatinib | 0.12 | 0.07 |

TABLE 9

Growth inhibition activity (EC$_{50}$) (in μM) of representative compounds against colorectal cancer LoVo cells

| Compound | EC$_{50}$ (μM) | Compound | EC$_{50}$ (μM) | Compound | EC$_{50}$ (μM) |
|---|---|---|---|---|---|
| Example 42 | 3 | Example 43 | 1.5 | Example 38 | 1.6 |
| Example 51 | 7.6 | Example 72 | 1.8 | Example 73 | 8.0 |
| Example 108 | 7.0 | Example 154 | 3.1 | Adriamycin | 1.5 |

EXAMPLES

Intermediate 1a: tert-butyl 4-oxopiperidine-1-carboxylate

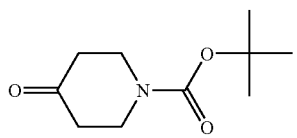

Hydrated 4-piperidone hydrochloride (8.65 g), BOC$_2$O (12.2 g), NaHCO$_3$ (8.8 g), and NaCl (11.2 g) were dissolved in a mixture of tetrahydrofuran (80 mL) and water (80 mL), stirred at room temperature, and allowed to stand overnight for layer separation. The water layer was extracted once with chloroform. The organic phases were combined, washed once with brine, dried over anhydrous magnesium sulfate and filtered. The filtrate was evaporated to give the title compound as a white solid (11.35 g).

Intermediate 1b: tert-butyl 3-oxopyrrolidine-1-carboxylate

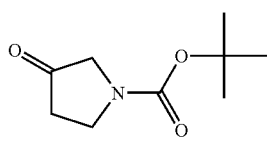

The title compound was prepared following the procedure for preparation of intermediate 1a except that 3-oxopyrrolidine hydrochloride was substituted for 4-piperidone hydrochloride.

Intermediate 1c: 1-(2-methoxyethyl)piperidin-4-one

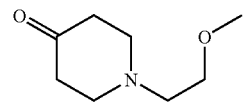

Hydrated 4-piperidone hydrochloride (8.65 g), 1-iodo-2-methoxyethane (12.58 g), and K$_2$CO$_3$ (15.55 g) were dissolved in a mixture of tetrahydrofuran (80 mL) and water (80 mL), stirred at room temperature, and allowed to stand overnight for layer separation. The water layer was extracted once with chloroform. The organic phases were combined, washed once with brine, dried over anhydrous magnesium sulfate, and filtered. The filtrate was evaporated in vacuo to give the title compound as an oil.

Intermediate 2a: tert-butyl 4-((methoxycarbonyl)methylene)piperidine-1-carboxylate

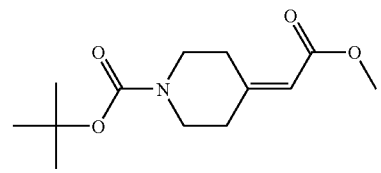

Sodium hydroxide (4.56 g, 0.114 mol) was dissolved in ethanol (210 mL), and trimethyl phosphonoacetate (11.4 g, 0.062 mol) added with stirring. The mixture was stirred for 30 min at room temperature. Tert-butyl 4-oxopiperidine-1-carboxylate (11.35 g, 0.057 mol) was added with stirring at room temperature, and the reaction was allowed to stand overnight. Then, the mixture was acidified with diluted hydrochloric acid until the pH was 4, filtered, concentrated, and partitioned into water and chloroform. Phases were separated. The aqueous phase was extracted once with chloroform. Chloroform phases were combined, washed once with brine, dried over anhydrous magnesium sulfate, and filtered. The filtrate was evaporated in vacuo to give the title compound.

Intermediate 2b: methyl 2-(1-(2-methoxyethyl)piperidin-4-ylidene)acetate

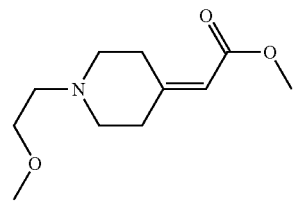

The title compound was prepared following the procedure for the preparation of intermediate 2a except that 1-(2-methoxyethyl)piperidin-4-one was substituted for 4-oxopiperidine-1-carboxylate.

Intermediate 2c: (E/Z)-tert-butyl 3-((methoxycarbonyl)methylene)pyrrolidine-1-carboxylate

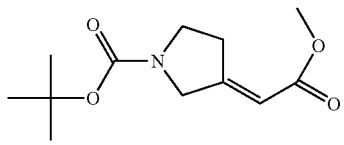

The title compound was prepared following the procedure for the preparation of intermediate 2a except that tert-butyl 3-oxopyrrolidine-1-carboxylate was substituted for 4-oxopiperidine-1-carboxylate.

Intermediate 3a: 2-(1-(tert-butoxycarbonyl)piperidin-4-ylidene)acetic acid

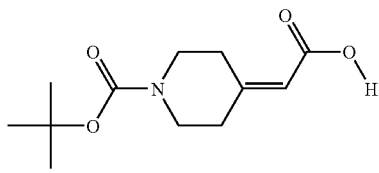

The above obtained tert-butyl 4-((methoxycarbonyl)methylene)piperidine-1-carboxylate was dissolved in a mixture of tetrahydrofuran (60 mL) and methanol (60 mL). 1N lithium hydroxide (60 mL) was added with stirring at room temperature, and the reaction mixture was allowed to stand overnight. Then, the mixture was extracted three times with dichloromethane. The organic phase was separated. The aqueous phase was acidified with 1N hydrochloric acid until the pH value was about 4 and extracted three times with dichloromethane. The organic phases were combined, washed once with brine, dried over anhydrous magnesium sulfate, and filtered. The filtrate was evaporated in vacuo to give the title compound.

Intermediate 3b:
2-(1-(2-methoxyethyl)piperidin-4-ylidene)acetic acid

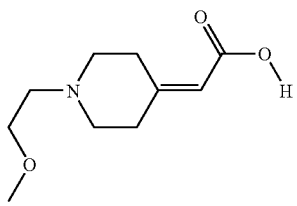

The title compound was prepared following the procedure for the preparation of intermediate 3a except that methyl 2-(1-(2-methoxyethyl)piperidin-4-ylidene)acetate was substituted for tert-butyl 4-((methoxycarbonyl)methylene)piperidine-1-carboxylate.

Intermediate 3c: (E/Z)-2-(1-(tert-butoxycarbonyl)pyrrolidin-3-ylidene)acetic acid

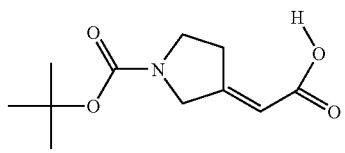

The title compound was prepared following the procedure for the preparation of the intermediate 3a except that (E/Z)-tert-butyl 3-((methoxycarbonyl)methylene)pyrrolidine-1-carboxylate was substituted for tert-butyl 4-((methoxycarbonyl)methylene)piperidine-1-carboxylate.

Intermediate 4a: $N^4$-(3-ethynylphenyl)quinazoline-4,6-diamine

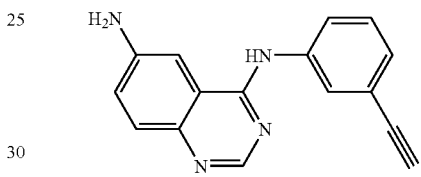

2 g of iron powder was immersed in diluted hydrochloric acid for 30 min, filtered, and washed with water. The washed iron powder, 0.1 g of N-(3-ethynylphenyl)-6-nitroquinazolin-4-amine, 25 mL of ethanol-water solution (water:ethanol=1:2), and 0.3 mL of acetic acid were added into a four-neck flask, and refluxed for one hour with mechanical stirring. After reaction completion, the mixture was cooled to room temperature, filtered, concentrated and ethyl acetate was added. The mixture was washed three times with hydrochloric acid. The aqueous layer was combined and made alkaline with $Na_2CO_3$ until the pH was about 9. The aqueous layer was extracted three times with ethyl acetate. All organic phases were combined, washed once with brine, dried over anhydrous magnesium sulfate, and filtered. The filtrate was evaporated in vacuo to give the title compound.

Intermediates 4b-4-r were prepared following the procedure for the preparation of intermediate 4a.

Intermediate 4b: $N^4$-(4-(benzyloxy)-3-chlorophenyl)quinazoline-4,6-diamine

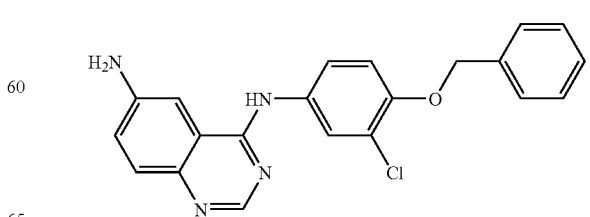

Intermediate 4c: N⁴-(4-(3-chlorobenzyloxy)-3-chlorophenyl)quinazoline-4,6-diamine Intermediate 4 g: N⁴-(3-chloro-4-(pyridin-2-ylmethoxy)phenyl)quinazoline-4,6-diamine

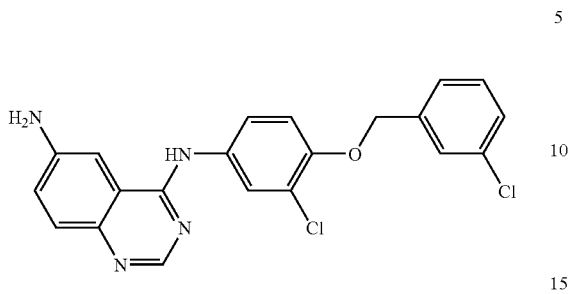

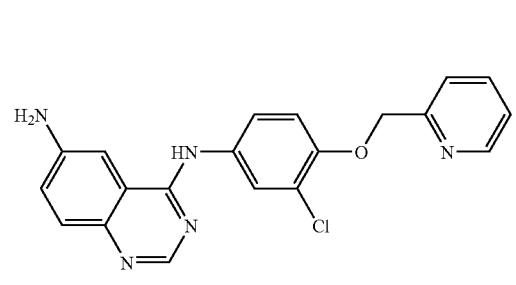

Intermediate 4d: N⁴-(4-(3-bromobenzyloxy)-3-chlorophenyl)quinazoline-4,6-diamine Intermediate 4 h: N⁴-(4-(3-fluorobenzyloxy)-3-chlorophenyl)-7-fluoroquinazoline-4,6-diamine

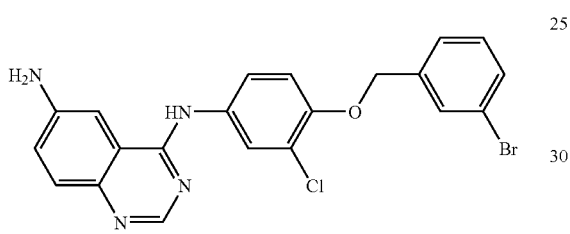

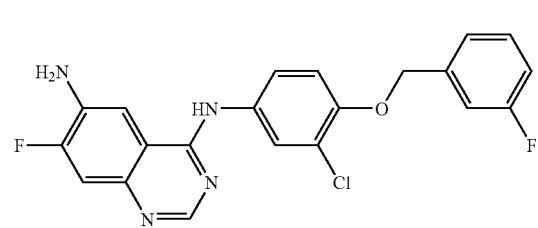

Intermediate 4e: N⁴-(4-(3-methoxybenzyloxy)-3-chlorophenyl)quinazoline-4,6-diamine Intermediate 4i: N⁴-(4-(3-fluorobenzyloxy)-3-chlorophenyl)-7-methoxyquinazoline-4,6-diamine

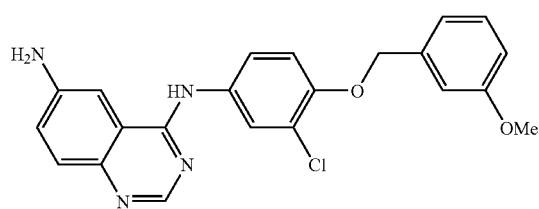

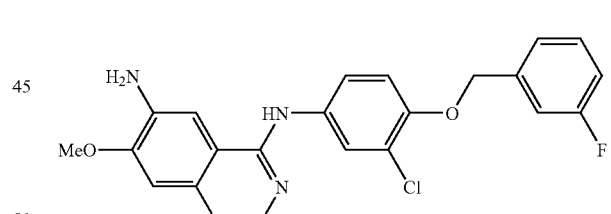

Intermediate 4f: N⁴-(4-(3-ethoxybenzyloxy)-3-chlorophenyl)quinazoline-4,6-diamine Intermediate 4j: N⁴-(4-(3-fluorobenzyloxy)-3-chlorophenyl)-7-ethoxyquinazoline-4,6-diamine

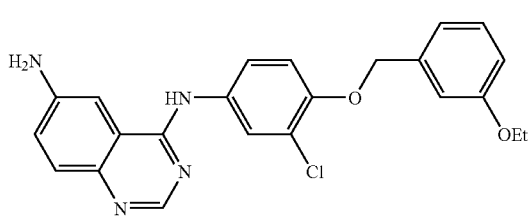

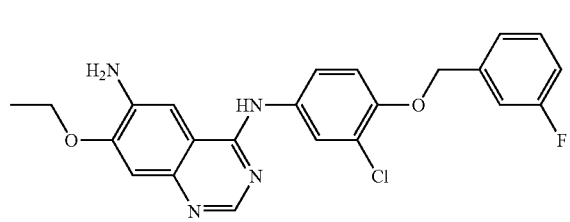

Intermediate 4k: N⁴-(4-(3-fluorobenzyloxy)-3-chlorophenyl)-7-(2-methoxyethoxy)quinazoline-4,6-diamine

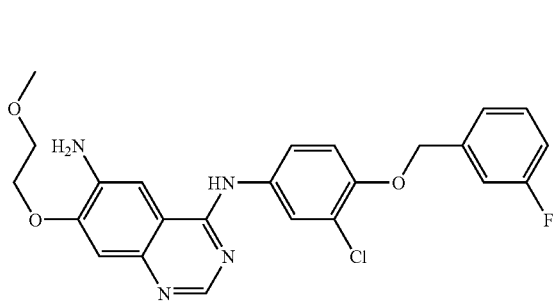

Intermediate 4l: N⁴-(4-(3-chlorobenzyloxy)-3-chlorophenyl)-7-methoxyquinazoline-4,6-diamine

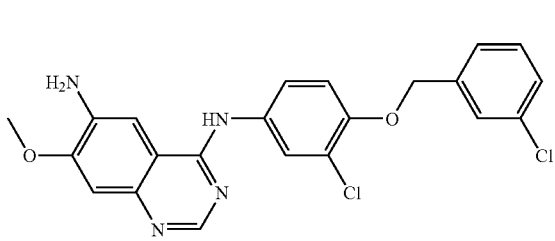

Intermediate 4m: N⁴-(3-chloro-4-(pyridin-2-ylmethoxy)phenyl)-7-methoxyquinazoline-4,6-diamine

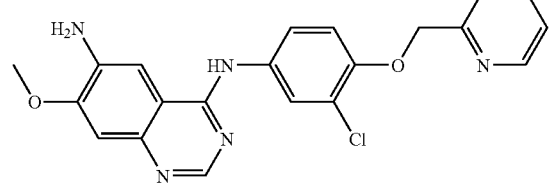

Intermediate 4n: N⁴-(1-benzyl-1H-indol-5-yl)quinazoline-4,6-diamine

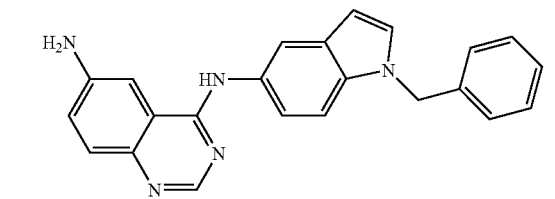

Intermediate 4o: N⁴-(1-(3-fluorobenzyl)-1H-indol-5-yl)-7-methoxyquinazoline-4,6-diamine

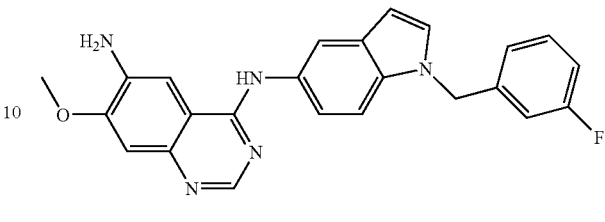

Intermediate 4p: N⁴-(1-benzyl-1H-indol-5-yl)-7-(2-methoxyethoxy)quinazoline-4,6-diamine

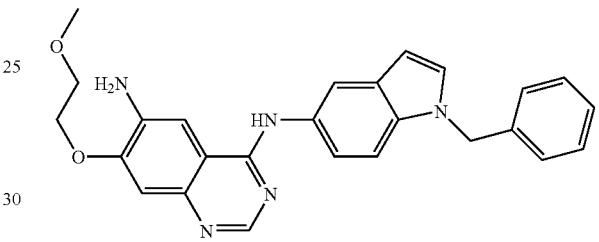

Intermediate 4q: 7-ethoxy-N⁴-(3-methoxy-4-phenoxyphenyl)quinazoline-4,6-diamine

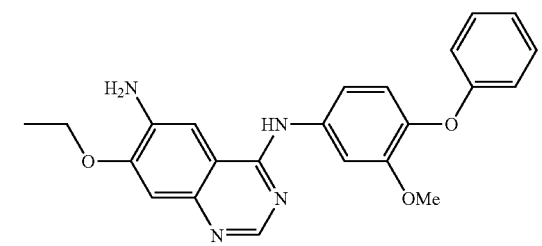

Intermediate 4r: 7-ethoxy-N⁴-(4-(4-fluorophenoxy)-3-methoxyphenyl) quinazoline-4,6-diamine

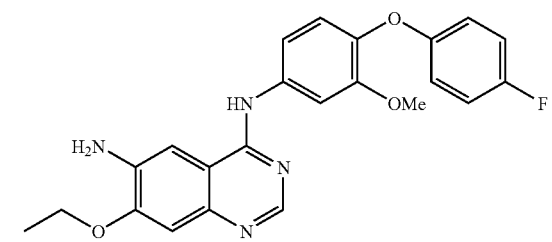

Example 1

Tert-butyl 4-((4-(3-ethynylphenylamino)quinazolin-6-ylcarbamoyl)methylene)piperidine-1-carboxylate

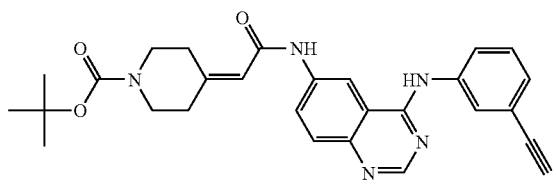

1 g of 2-(1-(tert-butyloxycarbonyl)piperidine-4-ylidene) acetic acid was added to 20 mL of anhydrous THF in a one-neck flask (100 mL). The solution was stirred and cooled on salt-ice bath. Then, 0.6 mL of isobutyl chloroformate and 0.5 mL of N-methylmorpholine were added, and the reaction mixture was let stir for 20 min. 1.046 g of $N^4$-(3-ethynylphenyl)quinazoline-4,6-diamine dissolved in 10 mL of pyridine (dried over molecular sieves) and 0.4 mL of N-methylmorpholine were added to the reaction mixture on an ice bath with stirring. After reaction completion, the solvent was evaporated in vacuo and the remaining residue was partitioned with chloroform and water. The chloroform layer was washed once with brine, dried over anhydrous magnesium sulfate, filtered, and evaporated in vacuo to give a crude product. The crude product was recrystallized from isopropanol. MS (EI) 482 $M^+$.

Example 2

N-(4-(3-ethynylphenylamino)quinazolin-6-yl)-2-(piperidin-4-ylidene)acetamide trifluoroacetate

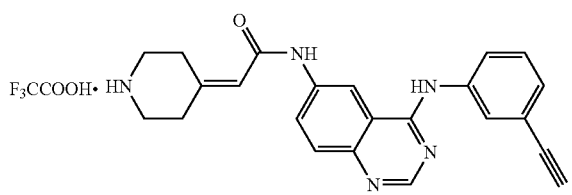

Tert-butyl-((4-(3-ethynylphenylamino)quinazolin-6-yl-aminocarbonyl)-methylene)piperidine-1-carboxylic ester (92 mg, 0.38 mmol) was dissolved in 10 mL of 20% anhydrous TFA/DCM solution and stirred at room temperature for 2 hours, evaporated in vacuo, and vacuum dried to give the tile compound as a whitish foam. MS: 384 (M+1).

Example 3

N-(4-(3-ethynylphenylamino)quinazolin-6-yl)-2-(piperidin-4-ylidene)acetamide

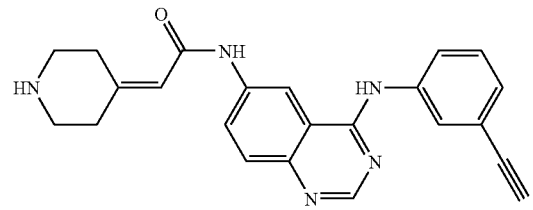

N-(4-(3-ethynylphenylamino)quinazolin-6-yl)-2-(piperidin-4-ylidene)acetamide trifluoroacetate was dissolved in ethyl acetate. The mixture was washed once with saturated $Na_2CO_3$ and once with brine, dried over anhydrous magnesium sulfate, filtered, and evaporated in vacuo to give the title product. MS (EI) 384 (M+1).

Example 4

N-(4-(3-ethynylphenylamino)quinazolin-6-yl)-2-(1-methylpiperidin-4-ylidene)acetamide

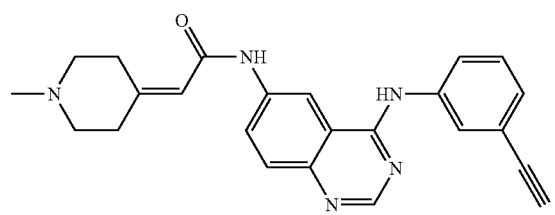

N-(4-(3-ethynylphenylamino)quinazolin-6-yl)-2-(piperidin-4-ylidene)acetamide (20 mg, 0.046 mmol), methyl iodide (8.0 mg, 0.056 mmol), anhydrous potassium carbonate (17 mg), and acetonitrile (5 mL) were placed in a one-neck flask (50 mL). The reaction mixture was stirred at room temperature for 24 hours. After reaction completion, the solution was filtered, and evaporated in vacuo to give a solid. The solid was purified by TLC (silica gel plate, thickness 5 mm, chloroform:methanol=95:5). MS: 398 (M+1).

The compounds of Example 5-8 were prepared following the procedure of Example 4.

Example 5

2-(1-Ethylpiperidin-4-ylidene)-N-(4-(3-ethynylphenylamino)quinazolin-6-yl)acetamide

MS: 412 (M+1).

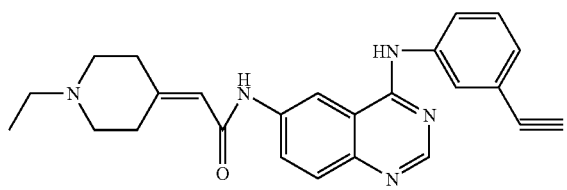

Example 6

2-(1-benzylpiperidin-4-ylidene)-N-(4-(3-ethynylphenylamino)quinazolin-6-yl)acetamide

MS: 474 (M+1).

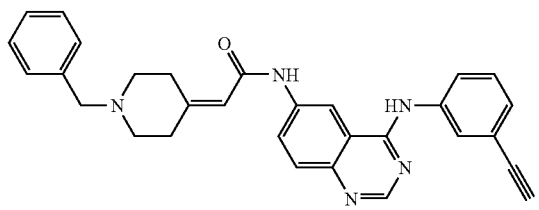

Example 7

N-(4-(3-ethynylphenylamino)quinazolin-6-yl)-2-(1-(2-methoxyethyl)piperidin-4-ylidene)acetamide

MS: 440 (M−1).

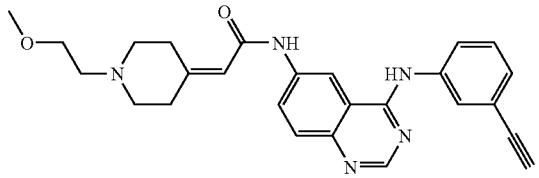

Example 8

Methyl 2-(4-((4-(3-ethynylphenylamino)quinazolin-6-ylcarbamoyl)methylene)piperidin-1-yl)acetate

MS: 454 (M+).

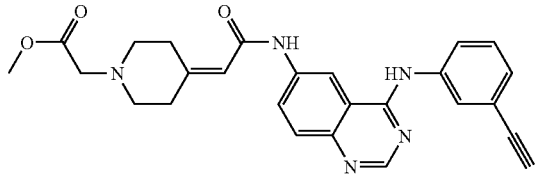

Example 9

N-(4-(3-ethynylphenylamino)quinazolin-6-yl)-2-(1-isopropylpiperidin-4-ylidene)acetamide

MS: 426 (M+1).

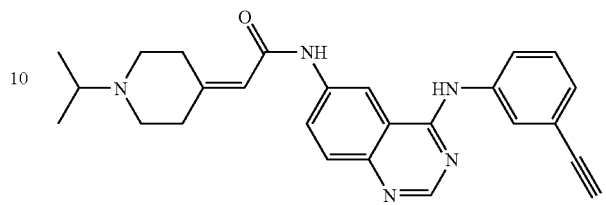

Example 10

N-(4-(3-ethynylphenylamino)quinazolin-6-yl)-2-(1-(2-hydroxyethyl)piperidin-4-ylidene)acetamide

MS: 428 (M+1).

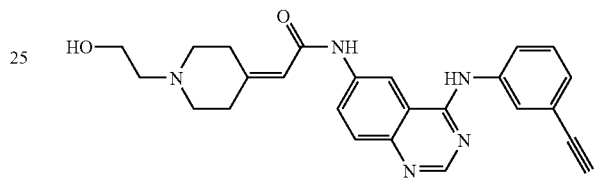

The compounds of Examples 11-29 were prepared following the procedure of Example 1.

Example 11

Tert-butyl 4-((4-(phenylamino)quinazolin-6-ylcarbamoyl)methylene)piperidine-1-carboxylate

MS: 459 (M+).

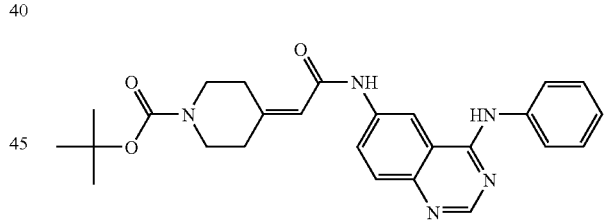

Example 12

Tert-butyl 4-((4-(3-chloro-4-fluorophenylamino)quinazolin-6-ylcarbamoyl)methylene)piperidine-1-carboxylate

MS: 511 (M+).

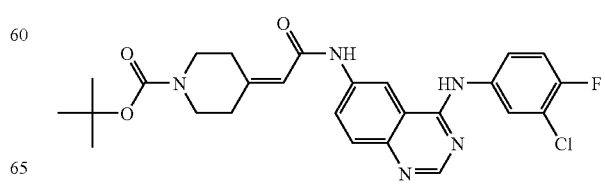

Example 13

Tert-butyl 4-((4-(3-bromophenylamino)quinazolin-6-ylcarbamoyl)methylene)piperidine-1-carboxylate

MS: 539 (M+1).

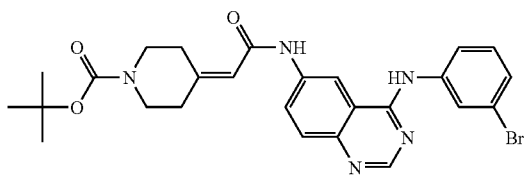

Example 14

Tert-butyl 4-((4-((S)-1-phenylethylamino)quinazolin-6-ylcarbamoyl)methylene)piperidine-1-carboxylate

MS: 487 (M$^+$).

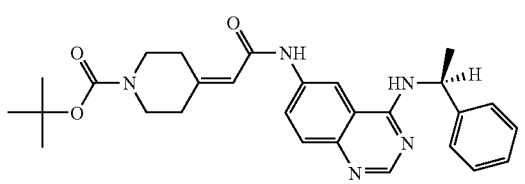

Example 15

Tert-butyl 4-((4-((R)-1-phenylethylamino)quinazolin-6-ylcarbamoyl)methylene)piperidine-1-carboxylate

MS: 487 (M$^+$).

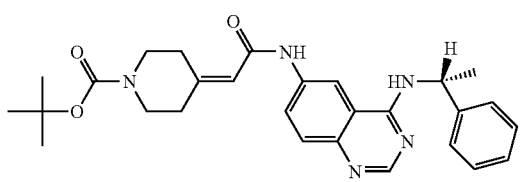

Example 16

Tert-butyl 4-((4-(3-chlorophenylamino)quinazolin-6-ylcarbamoyl)methylene)piperidine-1-carboxylate

MS: 493 (M$^+$).

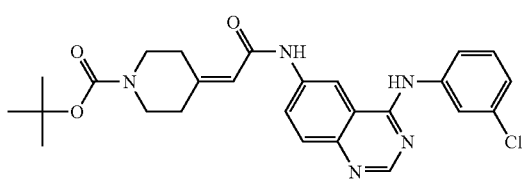

Example 17

Tert-butyl 4-((4-(3-chlorophenylamino)-7-fluoro-quinazolin-6-ylcarbamoyl)methylene)piperidine-1-carboxylate

MS: 511 (M$^+$).

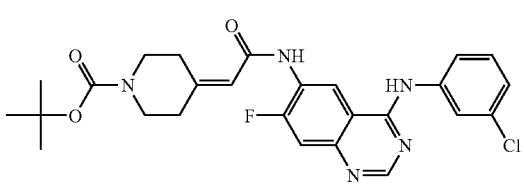

Example 18

Tert-butyl 4-((4-(3-bromophenylamino)-7-methoxyquinazolin-6-ylcarbamoyl)methylene)piperidine-1-carboxylate

MS: 568 (M+1).

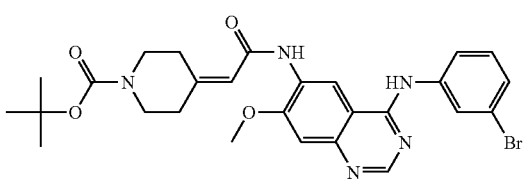

Example 19

Tert-butyl 4-((4-(3-bromophenylamino)-7-ethoxyquinazolin-6-ylcarbamoyl)methylene)piperidine-1-carboxylate

MS: 582 (M+1).

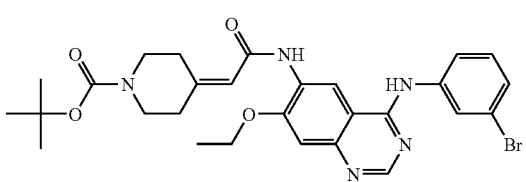

Example 20

Tert-butyl 4-((7-(2-methoxyethoxy)-4-(3-bromophenylamino)quinazolin-6-ylcarbamoyl)methylene)piperidine-1-carboxylate

MS: 612 (M+1).

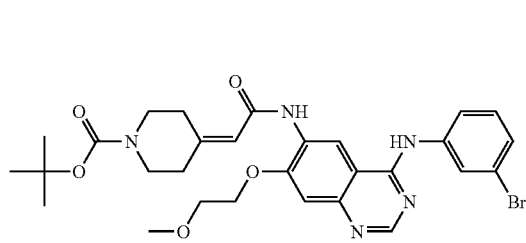

Example 21

Tert-butyl 4-((4-(1H-indol-5-ylamino)quinazolin-6-ylcarbamoyl)methylene)piperidine-1-carboxylate

MS: 498 (M$^+$).

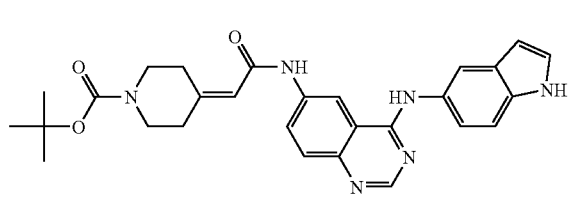

Example 22

Tert-butyl 4-((4-(3-ethynylphenylamino)-7-methoxyquinazolin-6-ylcarbamoyl)methylene)piperidine-1-carboxylate

MS: 512 (M$^+$).

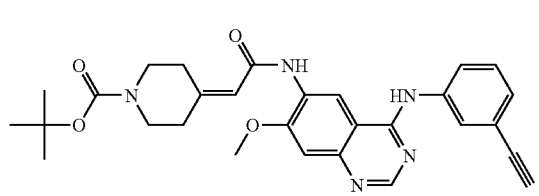

Example 23

Tert-butyl 4-((4-(3-chloro-4-fluorophenylamino)-7-methoxyquinazolin-6-ylcarbamoyl)methylene)piperidine-1-carboxylate

MS: 51 (M$^+$).

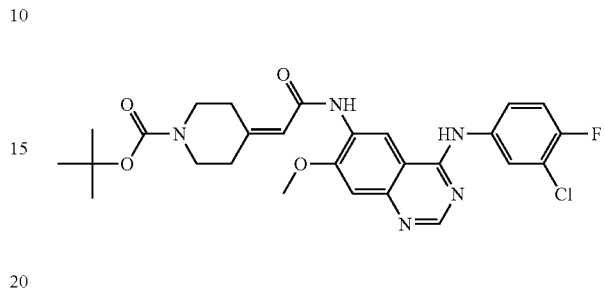

Example 24

Tert-butyl 4-((4-(1H-indol-5-ylamino)-7-methoxyquinazolin-6-ylcarbamoyl)methylene)piperidine-1-carboxylate

MS: 528 (M$^+$).

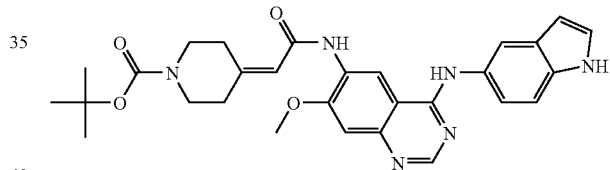

Example 25

Tert-butyl 4-((4-(3-bromophenylamino)-7-(3-methoxypropoxy)quinazolin-6-ylcarbamoyl)methylene)piperidine-1-carboxylate

MS: 626 (M$^+$).

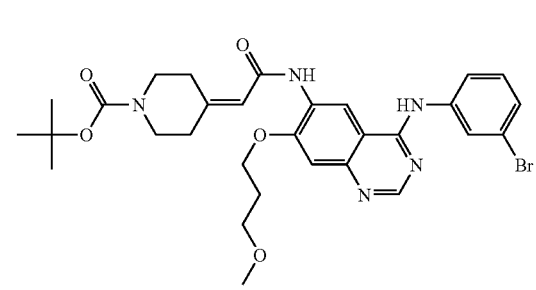

Example 26

Tert-butyl 4-((4-(3-bromophenylamino)-7-(3-morpholinopropoxy)quinazolin-6-ylcarbamoyl)methylene)piperidine-1-carboxylate

MS: 681 (M⁺).

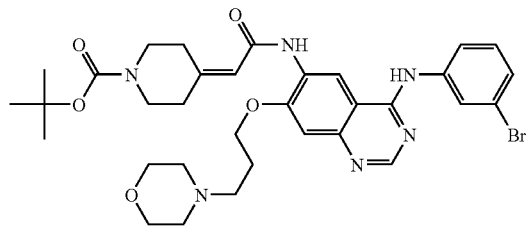

Example 27

Tert-butyl 4-((7-(2-methoxyethoxy)-4-(3-ethynylphenylamino)quinazolin-6-ylcarbamoyl)methylene)piperidine-1-carboxylate

MS: 557 (M+1).

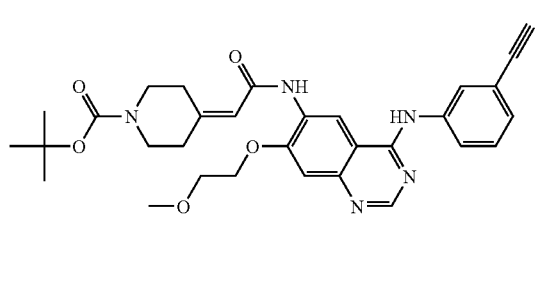

Example 28

Tert-butyl 4-((7-(2-methoxyethoxy)-4-(3-chloro-4-fluorophenylamino)quinazolin-6-ylcarbamoyl)methylene)piperidine-1-carboxylate

MS: 585 (M⁺).

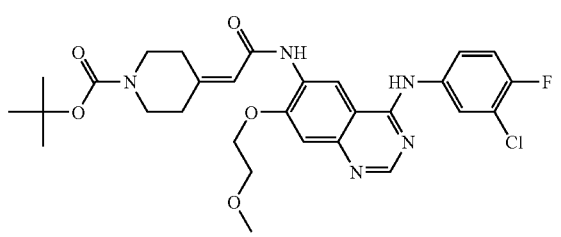

Example 29

Tert-butyl 4-((4-(1H-indol-5-ylamino)-7-(2-methoxyethoxy)quinazolin-6-ylcarbamoyl)methylene)piperidine-1-carboxylate

MS: 572 (M⁺).

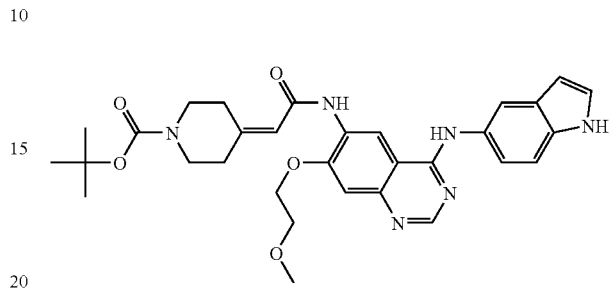

Following the procedure of Examples 2 and 3, the compounds of Examples 30-50 were prepared.

Example 30

N-(4-(3-chlorophenylamino)-7-fluoroquinazolin-6-yl)-2-(piperidin-4-ylidene)acetamide

MS: 411 (M+1).

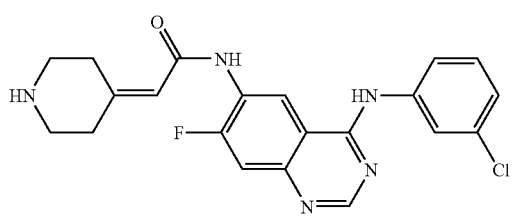

Example 31

N-(4-(phenylamino)quinazolin-6-yl)-2-(piperidin-4-ylidene)acetamide

MS: 359 (M+1).

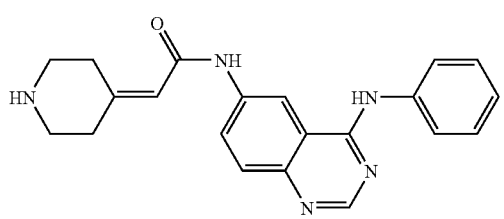

Example 32

N-(4-(3-chloro-4-fluorophenylamino)quinazolin-6-yl)-2-(piperidin-4-ylidene)acetamide

MS: 410 (M+).

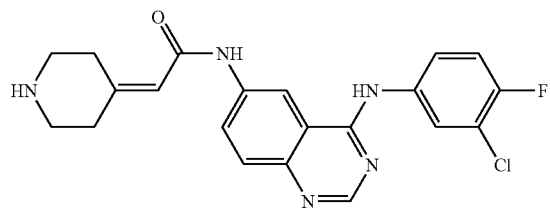

Example 33

N-(4-(3-bromophenylamino)quinazolin-6-yl)-2-(piperidin-4-ylidene)acetamide

MS: 438 (M+).

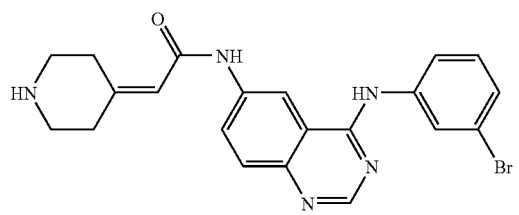

Example 34

N-(4-((S)-1-phenylethylamino)quinazolin-6-yl)-2-(piperidin-4-ylidene)acetamide

MS: 387 (M+).

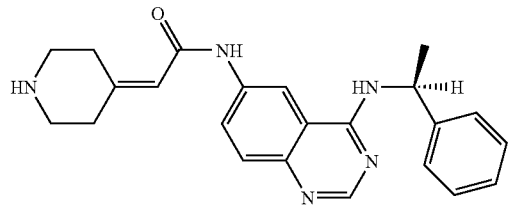

Example 35

N-(4-((R)-1-phenylethylamino)quinazolin-6-yl)-2-(piperidin-4-ylidene)acetamide

MS: 387 (M+).

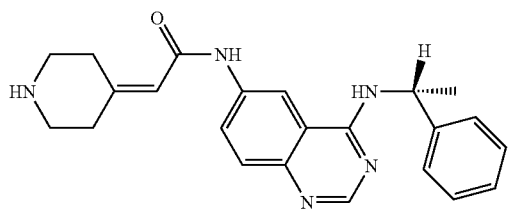

Example 36

N-(4-(3-chlorophenylamino)quinazolin-6-yl)-2-(piperidin-4-ylidene)acetamide

MS: 393 (M+).

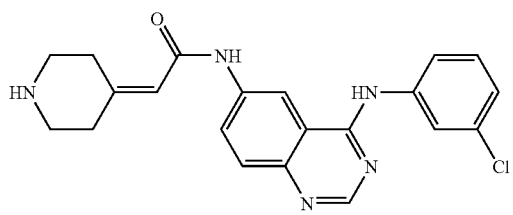

Example 37

N-(4-(3-bromophenylamino)-7-(3-morpholinopropoxy)quinazolin-6-yl)-2-(piperidin-4-ylidene)acetamide

MS: 581 (M+).

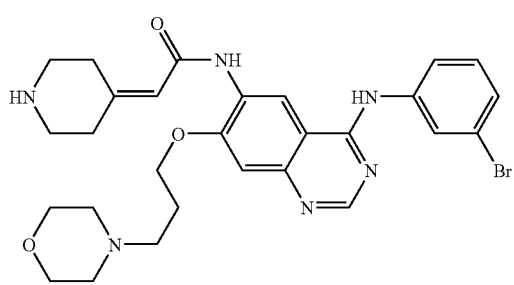

Example 38

N-(4-(3-bromophenylamino)-7-methoxyquinazolin-6-yl)-2-(piperidin-4-ylidene)acetamide MS: 467 (M+).

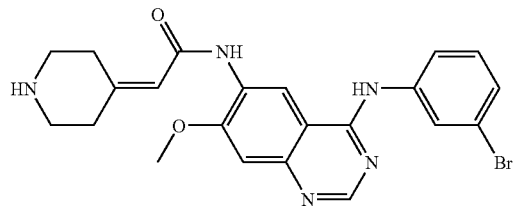

Example 39

N-(4-(3-bromophenylamino)-7-ethoxyquinazolin-6-yl)-2-(piperidin-4-ylidene)acetamide

MS: 482 (M+).

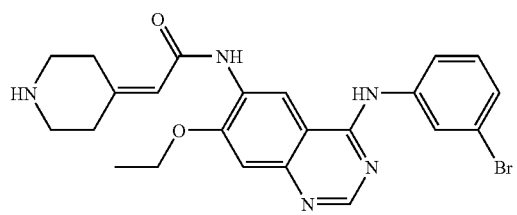

Example 40

N-(4-(3-bromophenylamino)-7-(2-methoxyethoxy)quinazolin-6-yl)-2-(piperidin-4-ylidene)acetamide

MS: 512 (M+1).

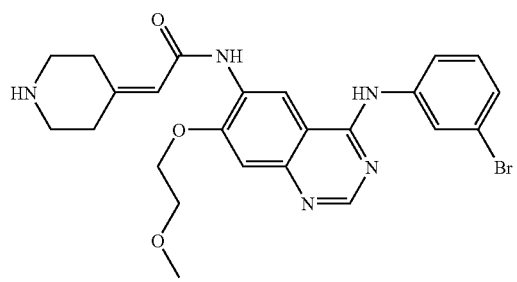

Example 41

N-(4-(1H-indol-5-ylamino)quinazolin-6-yl)-2-(piperidin-4-ylidene)acetamide

MS: 398 (M+1).

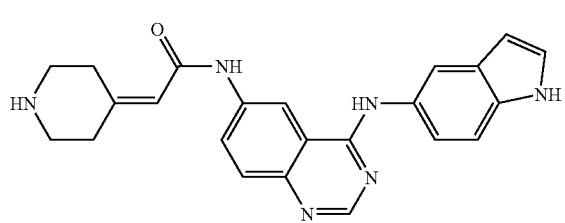

Example 42

N-(4-(3-ethynylphenylamino)-7-methoxyquinazolin-6-yl)-2-(piperidin-4-ylidene)acetamide

MS: 413 (M+).

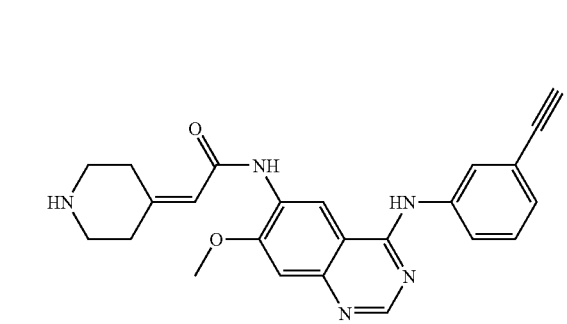

Example 43

N-(4-(3-chloro-4-fluorophenylamino)-7-methoxyquinazolin-6-yl)-2-(piperidin-4-ylidene)acetamide

MS: 441 (M+1).

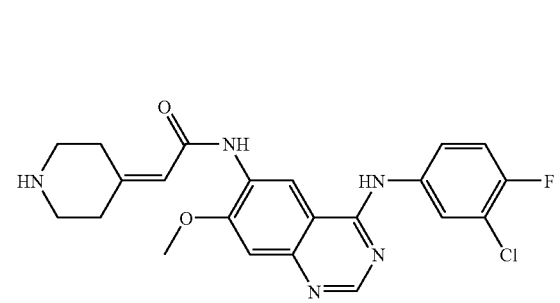

Example 44

N-(4-(1H-indol-5-ylamino)-7-methoxyquinazolin-6-yl)-2-(piperidin-4-ylidene)acetamide

MS: 428 (M+1).

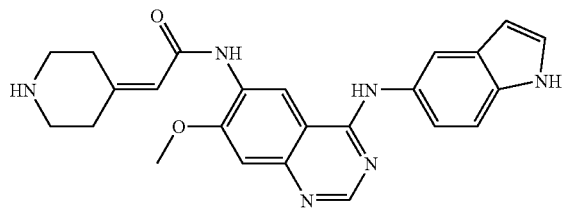

Example 45

(S)—N-(7-methoxy-4-(1-phenylethylamino)quinazolin-6-yl)-2-(piperidin-4-ylidene)acetamide

MS: 417 (M+).

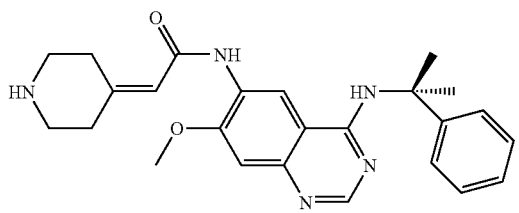

Example 46

(R)—N-(7-methoxy-4-(1-phenylethylamino)quinazolin-6-yl)-2-(piperidin-4-ylidene)acetamide

MS: 417 (M+).

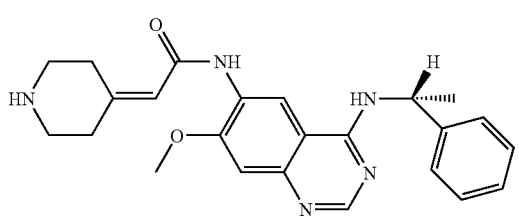

Example 47

N-(4-(3-ethynylphenylamino)-7-(2-methoxyethoxy)quinazolin-6-yl)-2-(piperidin-4-ylidene)acetamide

MS: 457 (M+).

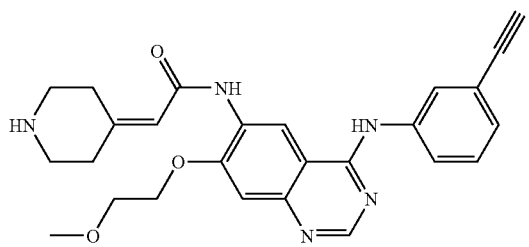

Example 48

N-(4-(3-chloro-4-fluorophenylamino)-7-(2-methoxyethoxy)quinazolin-6-yl)-2-(piperidin-4-ylidene)acetamide

MS: 485 (M+).

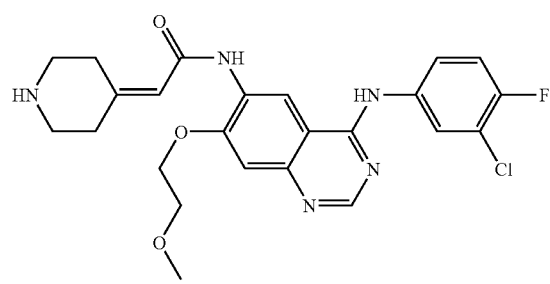

Example 49

N-(4-(3-ethynylphenylamino)-7-(3-morpholinopropoxy)quinazolin-6-yl)-2-(piperidin-4-ylidene)acetamide

MS: 526 (M+1).

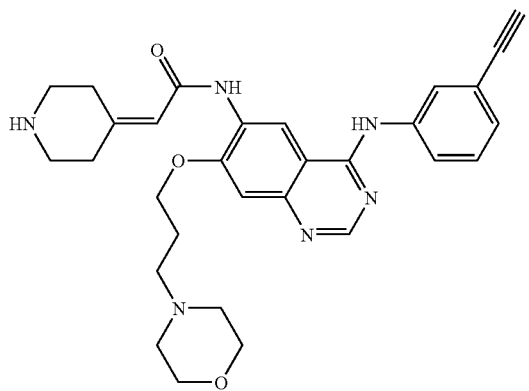

Example 50

N-(4-(3-ethynylphenylamino)-7-(3-methoxypropoxy)quinazolin-6-yl)-2-(piperidin-4-ylidene)acetamide

MS: 471 (M+1).

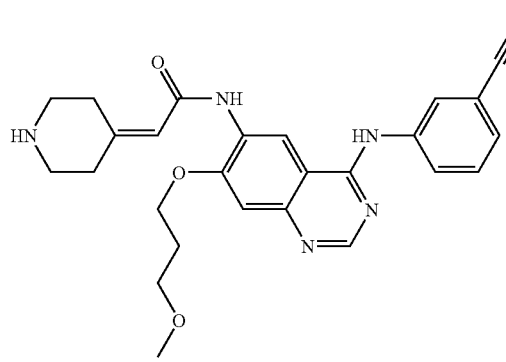

Following the procedure of Example 4, the compounds of Examples 51-83 were prepared.

Example 51

N-(4-(3-ethynylphenylamino)-7-methoxyquinazolin-6-yl)-2-(1-methylpiperidin-4-ylidene)acetamide

MS: 427 (M+1).

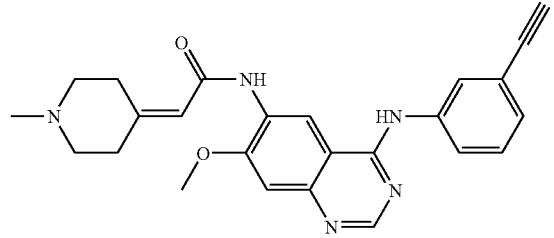

Example 52

N-(7-ethoxy-4-(3-ethynylphenylamino)quinazolin-6-yl)-2-(1-ethylpiperidin-4-ylidene)acetamide

MS: 455 (M$^+$).

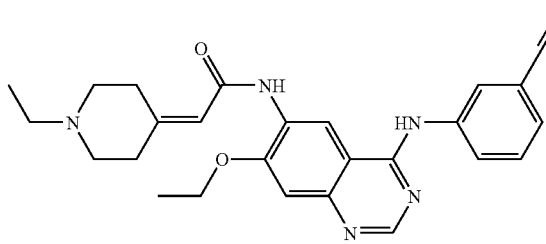

Example 53

2-(1-ethylpiperidin-4-ylidene)-N-(4-(3-ethynylphenylamino)-7-methoxyquinazolin-6-yl)acetamide

MS: 441 ($^+$).

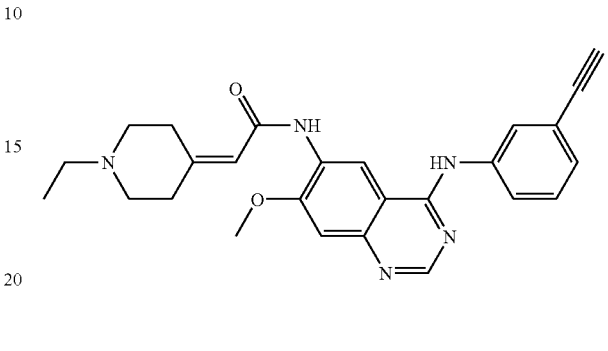

Example 54

N-(7-ethoxy-4-(3-ethynylphenylamino)quinazolin-6-yl)-2-(1-methylpiperidin-4-ylidene)acetamide

MS: 441 (M$^+$).

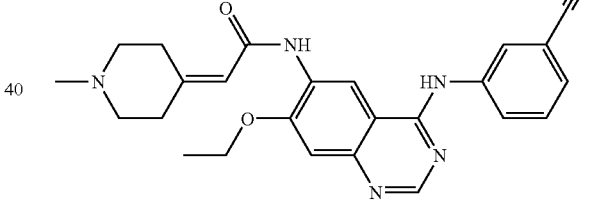

Example 55

N-(4-(3-bromophenylamino)quinazolin-6-yl)-2-(1-methylpiperidin-4-ylidene)acetamide

MS: 452 (M$^+$).

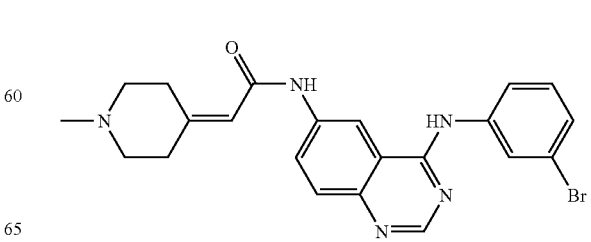

Example 56

N-(4-(3-bromophenylamino)quinazolin-6-yl)-2-(1-ethylpiperidin-4-ylidene)acetamide

MS: 466 (M+1).

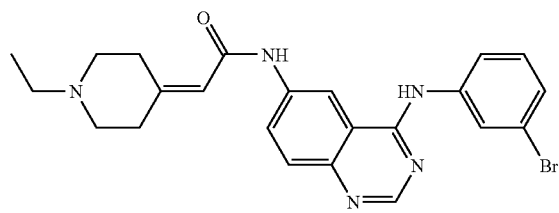

Example 57

N-(4-(3-bromophenylamino)quinazolin-6-yl)-2-(1-(2-methoxyethyl)piperidin-4-ylidene)acetamide

MS: 496 (M+1).

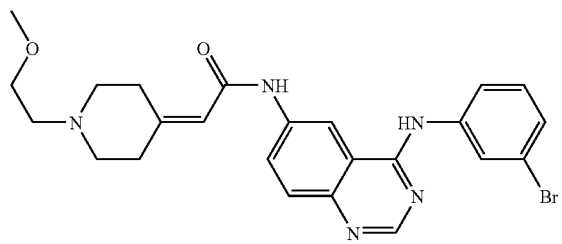

Example 58

N-(4-(3-bromophenylamino)-7-methoxyquinazolin-6-yl)-2-(1-methylpiperidin-4-ylidene)acetamide

MS: 482 (M+1).

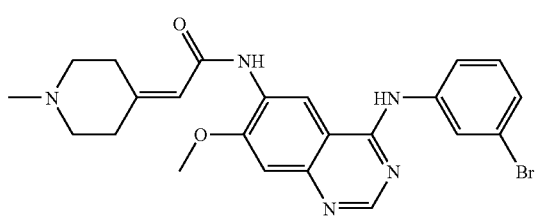

Example 59

N-(4-(3-bromophenylamino)-7-methoxyquinazolin-6-yl)-2-(1-ethylpiperidin-4-ylidene)acetamide

MS: 496 (M+1).

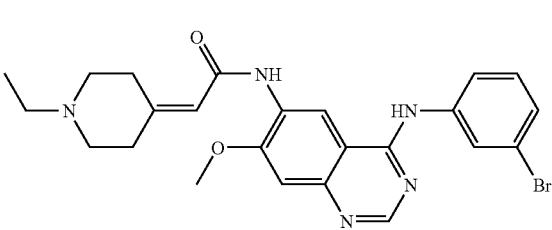

Example 60

N-(4-(3-bromophenylamino)-7-methoxyquinazolin-6-yl)-2-(1-(2-methoxyethyl)piperidin-4-ylidene)acetamide

MS: 526 (M$^+$).

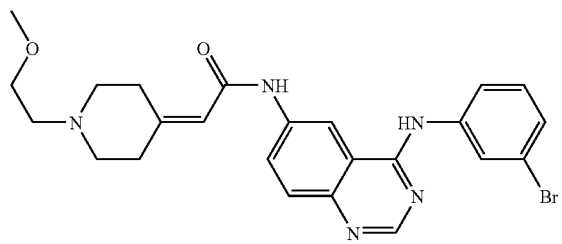

Example 61

N-(4-(3-bromophenylamino)-7-methoxyquinazolin-6-yl)-2-(1-(3-methoxypropyl)piperidin-4-ylidene)acetamide

MS: 540 (M$^+$).

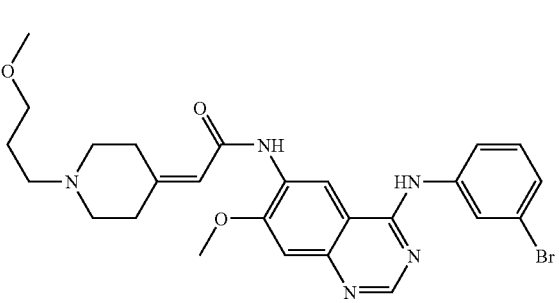

Example 62

N-(4-(3-bromophenylamino)-7-ethoxyquinazolin-6-yl)-2-(1-methylpiperidin-4-ylidene)acetamide

MS: 496 (M+1).

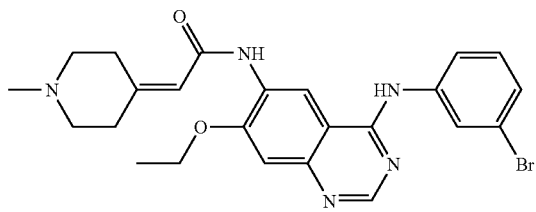

Example 63

N-(4-(3-bromophenylamino)-7-ethoxyquinazolin-6-yl)-2-(1-ethylpiperidin-4-ylidene)acetamide

MS: 510 (M+).

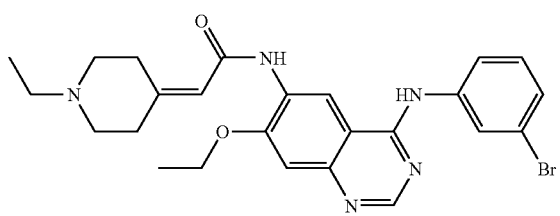

Example 64

N-(4-(3-bromophenylamino)-7-ethoxyquinazolin-6-yl)-2-(1-(2-methoxyethyl)piperidin-4-ylidene)acetamide

MS: 540 (M+).

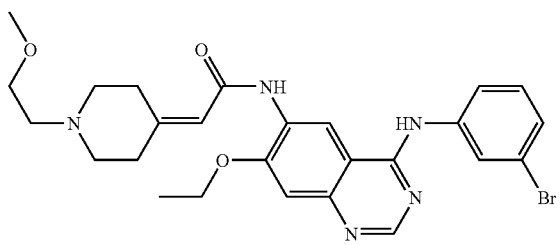

Example 65

N-(4-(3-bromophenylamino)-7-(2-methoxyethoxy)quinazolin-6-yl)-2-(1-methylpiperidin-4-ylidene)acetamide

MS: 526 (M+).

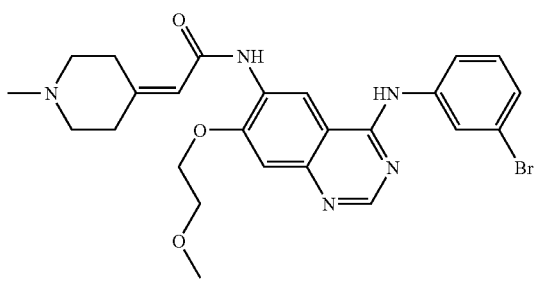

Example 66

N-(4-(3-bromophenylamino)-7-(3-methoxypropoxy)quinazolin-6-yl)-2-(1-methylpiperidin-4-ylidene)acetamide

MS: 540 (M+).

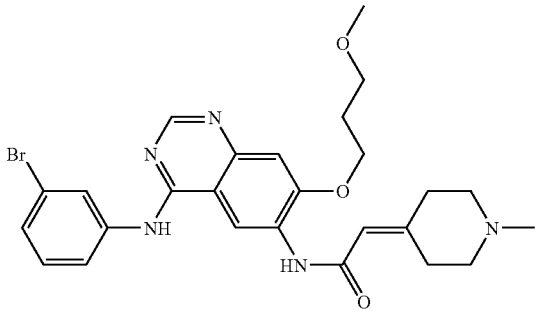

Example 67

N-(4-(3-bromophenylamino)-7-(3-(dimethylamino)propoxy)quinazolin-6-yl)-2-(1-methylpiperidin-4-ylidene)acetamide

MS: 552 (M+).

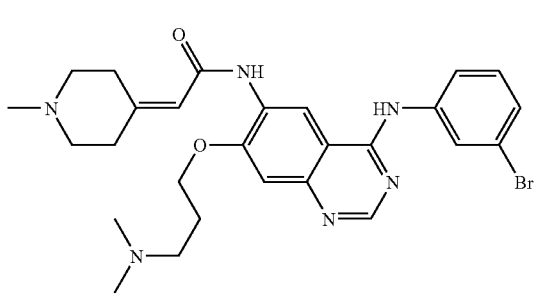

Example 68

N-(4-(3-bromophenylamino)-7-(3-morpholinopropoxy)quinazolin-6-yl)-2-(1-methylpiperidin-4-ylidene)acetamide

MS: 595 (M+1).

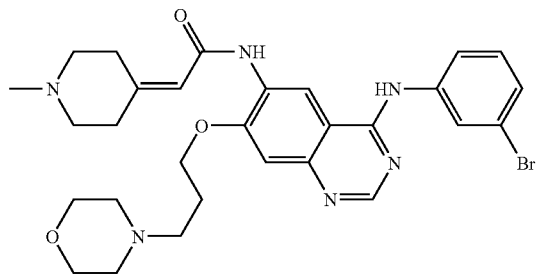

Example 69

N-(4-(3-chlorophenylamino)-7-fluoroquinazolin-6-yl)-2-(1-methylpiperidin-4-ylidene)acetamide

MS: 425 (M$^+$).

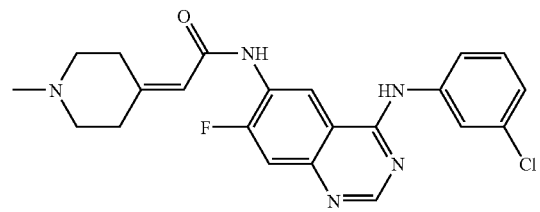

Example 70

N-(4-(3-chlorophenylamino)-7-fluoroquinazolin-6-yl)-2-(1-ethylpiperidin-4-ylidene)acetamide

MS: 439 (M$^+$).

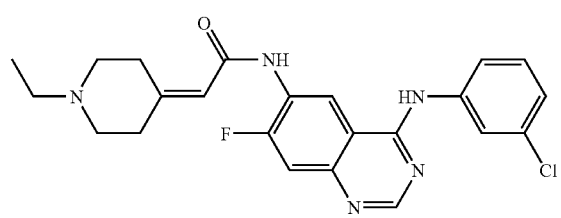

Example 71

N-(4-(3-chlorophenylamino)-7-fluoroquinazolin-6-yl)-2-(1-(2-methoxyethyl)piperidin-4-ylidene)acetamide

MS: 469 (M$^+$).

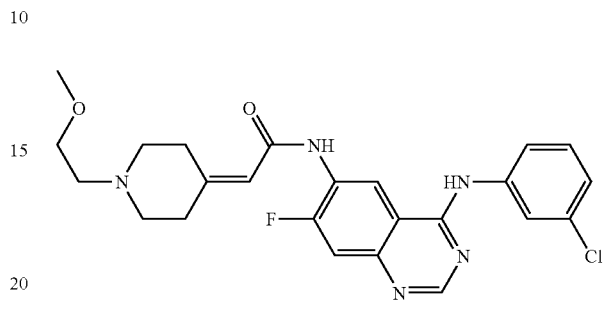

Example 72

N-(4-(3-chloro-4-fluorophenylamino)-7-methoxyquinazolin-6-yl)-2-(1-methylpiperidin-4-ylidene)acetamide

MS: 455 (M$^+$).

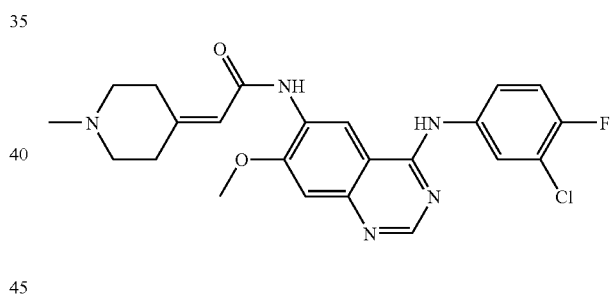

Example 73

N-(4-(3-chloro-4-fluorophenylamino)-7-methoxyquinazolin-6-yl)-2-(1-(2-methoxyethyl)piperidin-4-ylidene)acetamide

MS: 499 (M$^+$)

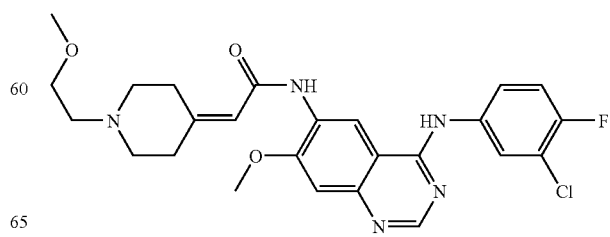

Example 74

N-(4-(3-chloro-4-fluorophenylamino)quinazolin-6-yl)-2-(1-(2-methoxyethyl)piperidin-4-ylidene)acetamide

MS: 469 (M+).

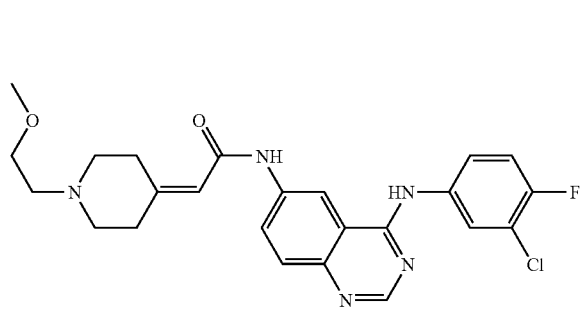

Example 75

N-(4-(1H-indol-5-ylamino)quinazolin-6-yl)-2-(1-methylpiperidin-4-ylidene)acetamide

MS: 412 (M+1).

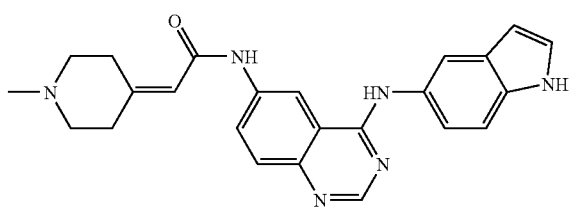

Example 76

N-(4-(1H-indol-5-ylamino)quinazolin-6-yl)-2-(1-ethylpiperidin-4-ylidene)acetamide

MS: 426 (M+1).

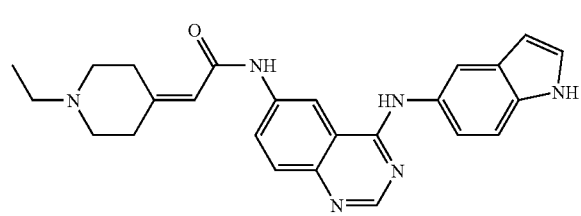

Example 77

N-(4-(1H-indol-5-ylamino)quinazolin-6-yl)-2-(1-(2-methoxyethyl)piperidin-4-ylidene)acetamide

MS: 456 (M+).

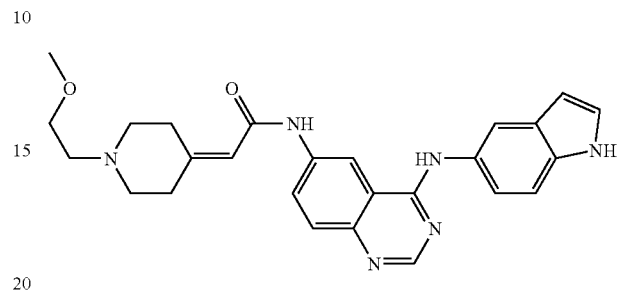

Example 78

(S)-2-(1-methylpiperidin-4-ylidene)-N-(4-(1-phenylethylamino)quinazolin-6-yl)acetamide

MS: 401 (M+).

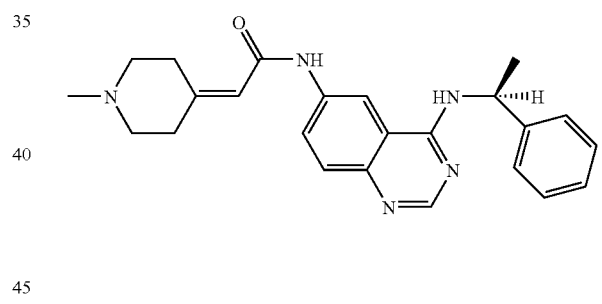

Example 79

(S)-2-(1-ethylpiperidin-4-ylidene)-N-(4-(1-phenylethylamino)quinazolin-6-yl)acetamide

MS: 415 (M+).

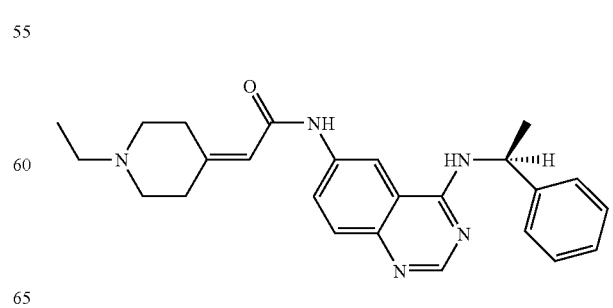

Example 80

(S)-2-(1-(2-methoxyethyl)piperidin-4-ylidene)-N-(4-(1-phenylethylamino)quinazolin-6-yl)acetamide

MS: 445 (M+).

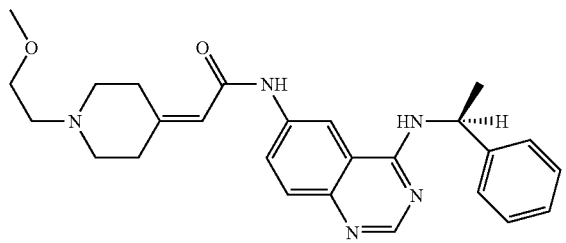

Example 81

(S)—N-(7-(2-methoxyethoxy)-4-(1-phenylethylamino)quinazolin-6-yl)-2-(piperidin-4-ylidene)acetamide

MS: 461 (M+).

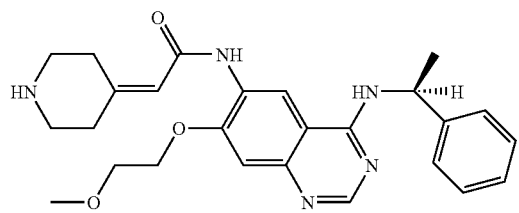

Example 82

N-(4-(1H-indol-5-ylamino)-7-(2-methoxyethoxy)quinazolin-6-yl)-2-(piperidin-4-ylidene)acetamide

MS: 472 (M+1).

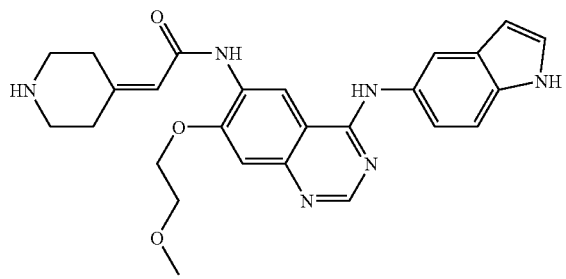

Example 83

N-(4-(3-bromophenylamino)quinazolin-6-yl)-2-(pyrrolidin-3-ylidene)acetamide

MS: 423 (M+1).

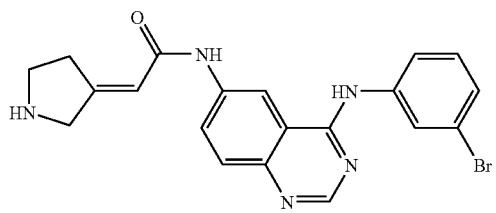

Example 84

Comparison compound A: N-(4-(3-bromophenylamino)quinazolin-6-yl)propionamide

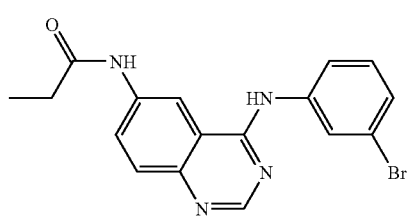

$N^4$-(3-bromophenyl)quinazoline-4,6-diamine (100 mg, 0.32 mmol), pyridine (0.3 mL), and DMAP (20 mg) were dissolved in 10 mL of anhydrous THF. The solution was cooled to 5° C. Propionyl chloride (33 mg, 0.35 mmol) was added to the reaction flask dropwise. Ice bath removed was removed, and the reaction mixture was stirred at room temperature and filtered. The filtrate was dried in vacuo to give a yellow solid. The yellow solid was dissolved in ethyl acetate, washed once with saturated $Na_2CO_3$, then with 10% acetic acid, and then with brine. The organic phase was dried, filtered, and stripped of solvent in vacuo to give a crude product which was purified by TLC to give the title compound as a whitish product.

Example 85

Comparison compound B: N-(4-(3-bromophenylamino)quinazolin-6-yl)acrylamide

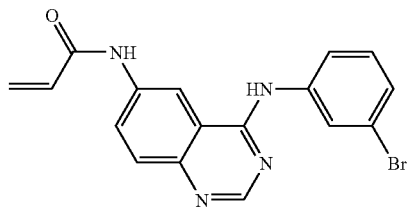

The title compound was prepared following the procedure of Example 84 and substituting acryloyl chloride for propionyl chloride.

Example 86

Comparison Compound C: N-(4-(3-bromophenylamino)quinazolin-6-yl)-3-methylbut-2-enamide

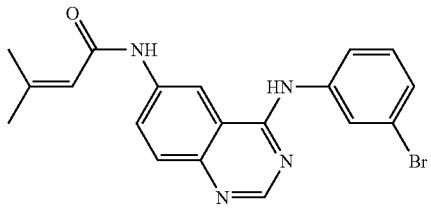

The title compound was prepared following the procedure of Example 84 and substituting 3-methyl-butyl-2-en-acyl chloride for propionyl chloride.

Example 87

N-(7-methoxy-4-(2-phenylcyclopropylamino)quinazolin-6-yl)-2-(1-(2-methoxyethyl)piperidin-4-ylidene)acetamide

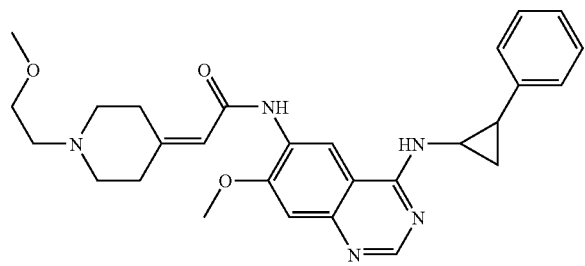

1) Preparation of 2-(1-(2-methoxyethyl)piperidin-4-ylidene)acetyl chloride hydrochloride

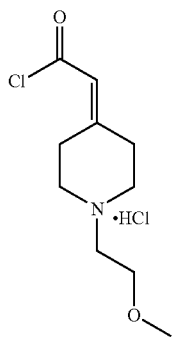

2.4 g of 2-(1-(2-methoxyethyl)piperidin-4-ylidene)acetic acid was dissolved in 20 mL of thionyl chloride, refluxed for 2 hours, evaporated in vacuo to remove thionyl chloride and give a solid product.

2) Preparation of N-(7-methoxy-4-(2-phenylcyclopropylamino) quinazolin-6-yl)-2-(1-(2-methoxyethyl)piperidin-4-ylidene)acetamide Following the procedure of Example 84, the title compound was prepared by reacting 2-(1-(2-methoxyethyl)piperidin-4-ylidene)acetyl chloride hydrochloride with $N^4$-(7-methoxy-4-(2-phenylcyclopropyl)quinazolin-4,6-diamine.

Example 88

$N^1$-(4-(3-bromophenylamino)quinazolin-6-yl)-$N^4$-(2-(2-(dimethylamino)ethoxy)ethyl)fumaramide

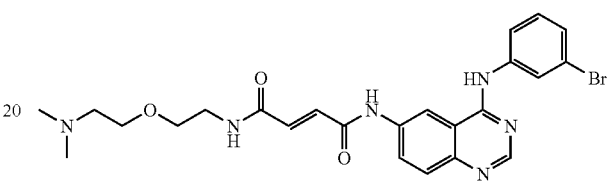

79 mg of $N^4$-(3-bromophenyl)quinazoline-4,6-diamine, 39 mg of maleic anhydride, and 15 mL of THF were placed in a one-neck flask (50 mL) and refluxed. After the reaction was completed, the reaction mixture was evaporated in vacuo and purified by thin layer chromatography.

The pure product was dissolved in anhydrous THF, and 2-(2-aminoethoxy)ethanol was added. The solution was cooled in ice bath. Subsequently, THF solution containing DCC was added dropwise, ice bath was removed, and the reaction mixture was refluxed for a day. After the reaction was completed, the solution was cooled to room temperature, filtered, and evaporated in vacuo to give crude title product.

105 mg of the crude product was dissolved in 20 mL pyridine, and 400 mg of 4-methylbenzene-1-sulfonyl chloride added with stirring at room temperature. After the reaction was completed, the solvent was evaporated in vacuo and the residue was dissolved in ethyl acetate, washed once with saturated $Na_2CO_3$, once with 1N HCl, and once with brine. The organic phase was dried over anhydrous magnesium sulfate, filtered, and evaporated in vacuo to give a product.

The product was dissolved in 10 mL pyridine, and dimethylamine added with stirring at room temperature. After the reaction was completed, the solvent was evaporated in vacuo and the title purified by thin layer chromatography. MS (EI) 528 $M^+$.

Example 89

N-(4-(3-bromophenylamino)quinazolin-6-yl)-2-(1-(2-(2-(2-hydroxyethoxy)ethylamino)acetyl)piperidin-4-ylidene)acetamide

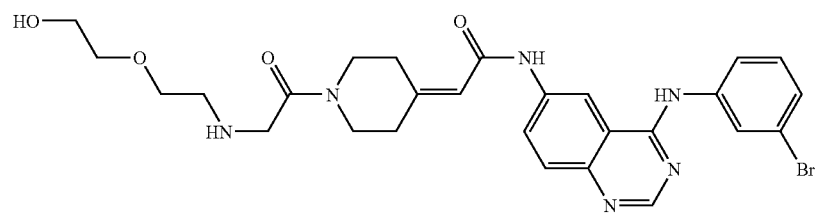

40 mg of N-(4-(3-bromophenylamino)quinazolin-6-yl)-2-(piperidine-4-ylidene)acetamide and 10 ml of THF were added in a one-mouth flask (50 ml), cooled in ice bath, 0.01 mL of 2-chloroacetyl chloride, and 0.02 mL of triethylamine (dried over molecular sieves) were added with stirring at room temperature. After the reaction was completed, the solvent was evaporated in vacuo, the residue was dissolved in ethyl acetate, washed three times with water and once with brine, dried over anhydrous magnesium sulfate, filtered, and evaporated in vacuo to give a crude product (30 mg).

The crude product was dissolved in 10 mL of acetonitrile, and 7.3 mg (0.07 mmol) of 2-(2-aminoethoxy)ethanol and 0.02 mL of triethylamine (dried over molecular sieves) were added with stirring at room temperature. After the reaction was completed, the solvent was evaporated in vacuo and the remaining residue was purified by thin layer chromatography. MS (EI) 581 M$^+$.

Compounds in Examples 90-101 were prepared using literature procedures.

Example 90

$N^4$-(4-(3-fluorobenzyloxy)-3-chlorophenyl)-7-(3-morpholinopropoxy)quinazoline-4,6-diamine

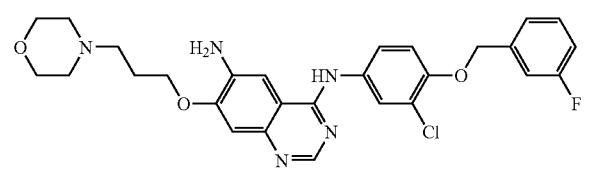

Example 91

$N^4$-(4-(3-fluorobenzyloxy)-3-chlorophenyl)-7-(3-methoxypropoxy)quinazoline-4,6-diamine

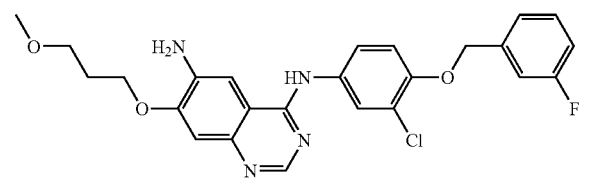

Example 92

$N^4$-(3-chloro-4-(pyridin-2-ylmethoxy)phenyl)-7-ethoxyquinazoline-4,6-diamine

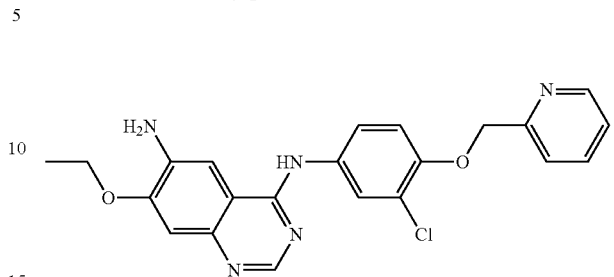

Example 93

$N^4$-(3-chloro-4-(pyridin-2-ylmethoxy)phenyl)-7-methoxyquinazoline-4,6-diamine

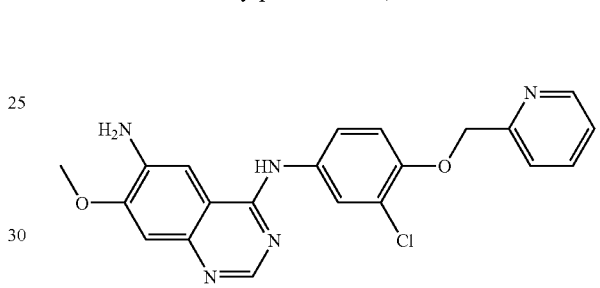

Example 94

$N^4$-(3-chloro-4-(pyridin-2-ylmethoxy)phenyl)-7-fluoroquinazoline-4,6-diamine

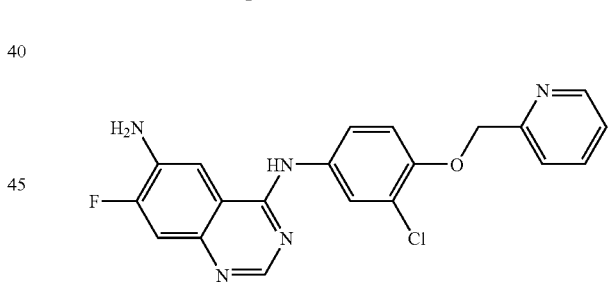

Example 95

$N^4$-(3-chloro-4-(pyridin-2-ylmethoxy)phenyl)quinazoline-4,6-diamine

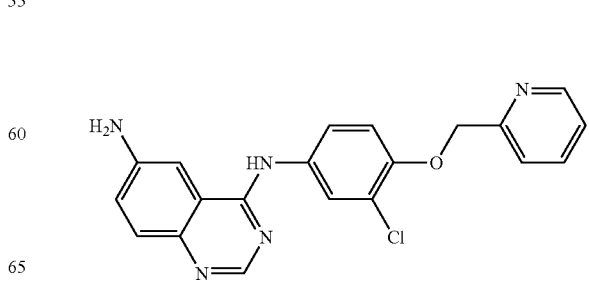

Example 96

7-methoxy-$N^4$-(3-methoxy-4-phenoxyphenyl)quinazoline-4,6-diamine

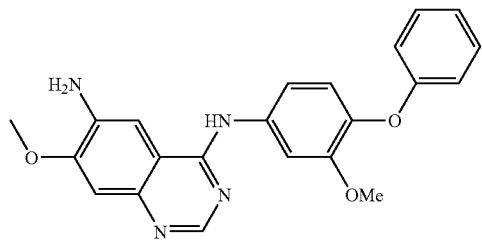

Example 97

7-methoxy-$N^4$-(4-(3-methoxyphenoxy)phenyl)quinazoline-4,6-diamine

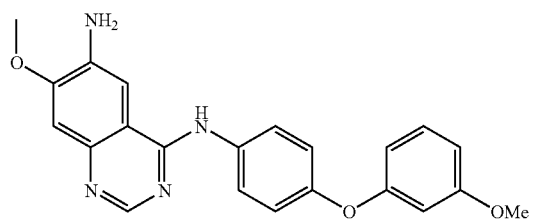

Example 98

$N^4$-(2-chloro-4-(pyridin-2-ylmethoxy)phenyl)-7-methoxyquinazoline-4,6-diamine

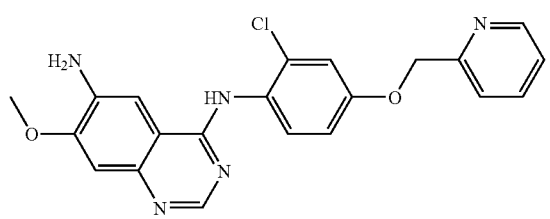

Example 99

$N^4$-(4-(benzyloxy)-3-chlorophenyl)-7-methoxyquinazoline-4,6-diamine

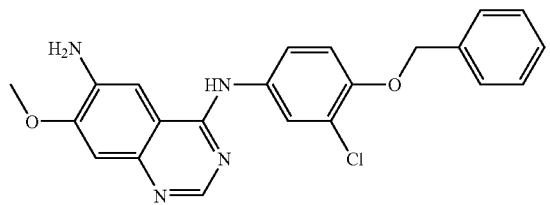

Example 100

$N^4$-(4-(3-chlorobenzyloxy)-3-fluorophenyl)-7-methoxyquinazoline-4,6-diamine

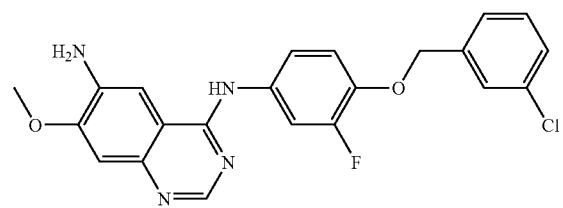

Example 101

$N^4$-(4-(3-chloro-4-fluorobenzyloxy)phenyl)-7-methoxyquinazoline-4,6-diamine

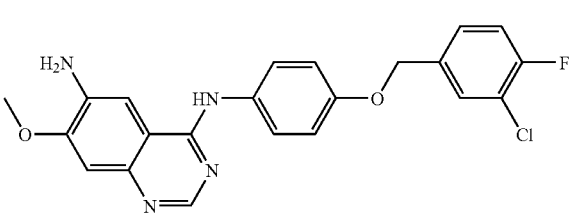

Example 102

Tert-butyl 4-((4-(4-((pyridin-2-yl)methoxy)-3-chlorophenylamino)quinazolin-6-ylcarbamoyl)methylene)piperidine-1-carboxylate

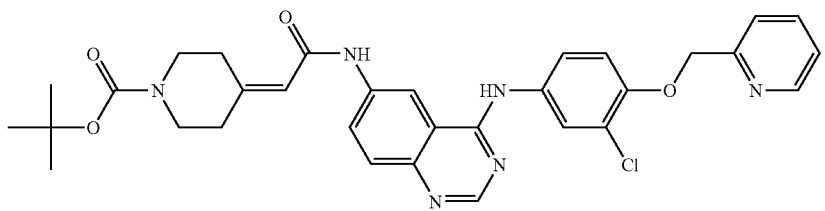

1 g of 2-(1-(tert-butyloxycarbonyl)piperidine-4-ylidene) acetic acid and 20 mL of anhydrous THF were placed in a one-neck flask (100 mL), dissolved in stirring, and cooled on a salt-ice bath. Then, 0.6 mL of isobutyl chloroformate and 0.5 mL of N-methylmorpholine were added, stirring for 20 mins. Then, 1.046 g of $N^4$-(4-3-chloro-(pyridin-2-ylmethoxy)phenyl)quinazoline-4,6-diamine dissolved in 10 mL of pyridine (dried over molecular sieves), and 0.4 mL of N-methylmorpholine were added with stirring to the reaction flask which was previously cooled on an ice bath. After the reaction was completed, the solvent was evaporated in vacuo and the crude product was partitioned with chloroform and water. The chloroform layer was washed once with saturated brine, dried over anhydrous magnesium sulfate, filtered, and evaporated in vacuo to give the crude title product which was recrystallized from isopropanol. MS (EI) 601 M+.

Example 103

N-(4-(3-chloro-4-(pyridin-2-ylmethoxy)phenylamino)quinazolin-6-yl)-2-(piperidin-4-ylidene)acetamide trifluoroacetate

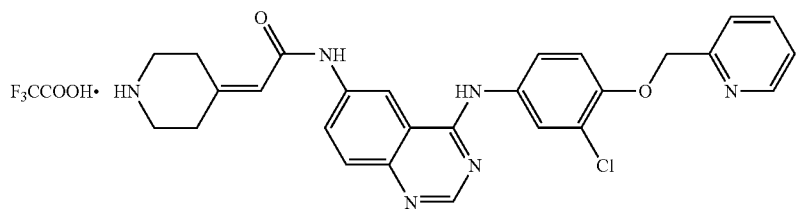

Tert-butyl-4-((4-(3-chloro-4-(pyridin-2-ylmethoxy)phenylamino)quinazolin-6-yl-aminocarbonyl)-methylene)piperidine-1-carboxylic ester (92 mg, 0.38 mmol) was dissolved in 10 mL of 20% anhydrous TFA/DCM solution with stirring at room temperature for 2 hours, evaporated in vacuo, and vacuum dried to give the title product as a whitish foam solid. MS: 501 (M+1).

Example 104

N-(4-(3-chloro-4-(pyridin-2-ylmethoxy)phenylamino)quinazolin-6-yl)-2-(piperidin-4-ylidene)acetamide

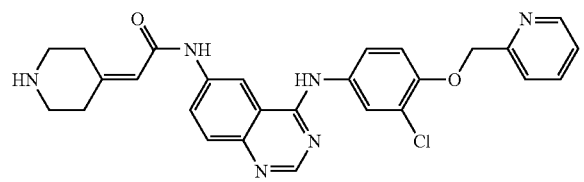

N-(4-(3-chloro-4-(pyridin-2-ylmethoxy)phenylamino) quinazolin-6-yl)-2-(piperidin-4-ylidene)acetamide trifluoroacetate was dissolved in ethyl acetate, washed once with saturated $Na_2CO_3$, and once with brine, dried over anhydrous magnesium sulfate, filtered, and evaporated in vacuo to give the title product. MS (EI) 501 (M+1).

Compounds of Examples 105-115 were prepared following the procedure of Example 104.

Example 105

N-(4-(4-(3-fluorobenzyloxy)-3-chlorophenylamino)-7-methoxyquinazolin-6-yl)-2-(piperidin-4-ylidene)acetamide

MS: 548 (M+1).

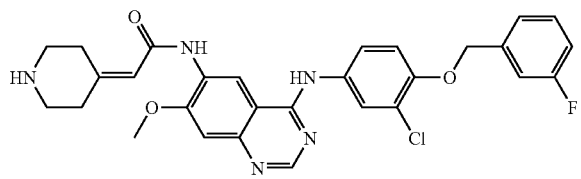

Example 106

N-(4-(4-(3-fluorobenzyloxy)-3-chlorophenylamino)-7-(3-methoxypropoxy)quinazolin-6-yl)-2-(piperidin-4-ylidene)acetamide

MS: 605 (M+).

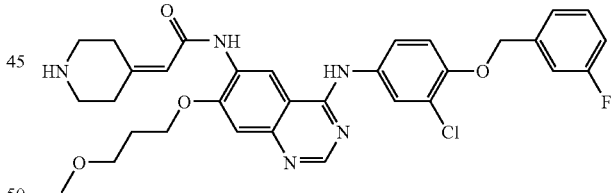

Example 107

N-(4-(3-chloro-4-(pyridin-2-ylmethoxy)phenylamino)-7-ethoxyquinazolin-6-yl)-2-(piperidin-4-ylidene)acetamide

MS: 544 (M+).

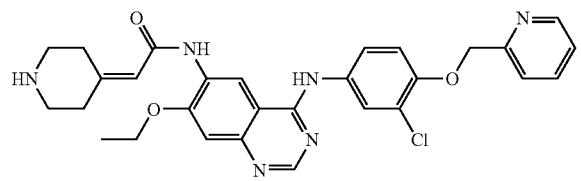

Example 108

N-(4-(3-chloro-4-(pyridin-2-ylmethoxy)phenylamino)-7-methoxyquinazolin-6-yl)-2-(piperidin-4-ylidene)acetamide

MS: 531 (M+1).

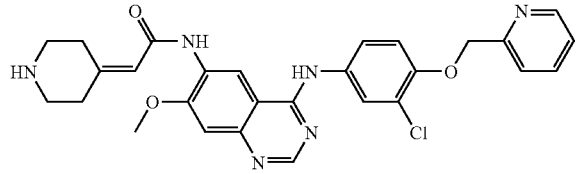

Example 109

N-(4-(3-chloro-4-(pyridin-2-ylmethoxy)phenylamino)-7-fluoroquinazolin-6-yl)-2-(piperidin-4-ylidene)acetamide

MS: 519 (M+1).

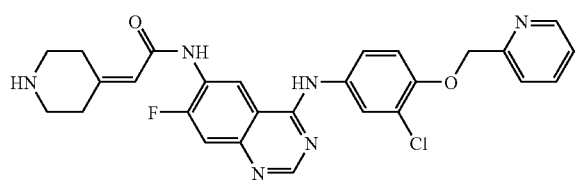

Example 110

N-(7-methoxy-4-(3-methoxy-4-phenoxyphenylamino)quinazolin-6-yl)-2-(piperidin-4-ylidene)acetamide

MS: 512 (M+1).

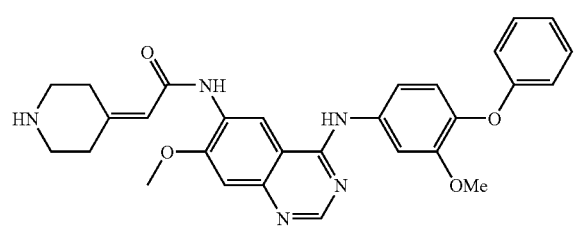

Example 111

N-(7-methoxy-4-(4-(3-methoxyphenoxy)phenylamino)quinazolin-6-yl)-2-(piperidin-4-ylidene)acetamide

MS11 (M$^+$).

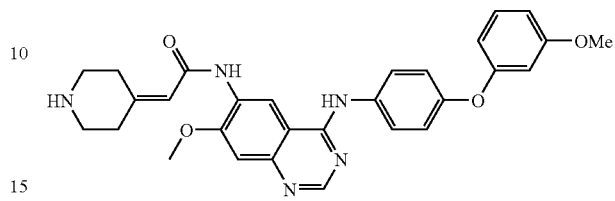

Example 112

N-(4-(2-chloro-4-(pyridin-2-ylmethoxy)phenylamino)-7-methoxyquinazolin-6-yl)-2-(piperidin-4-ylidene)acetamide

MS: 531 (M+1).

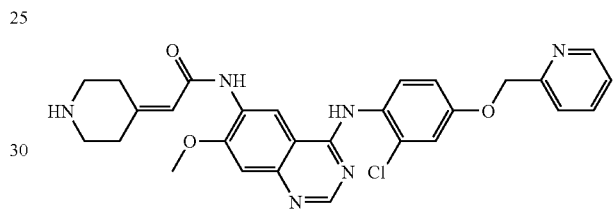

Example 113

N-(4-(4-(benzyloxy)-3-chlorophenylamino)-7-methoxyquinazolin-6-yl)-2-(piperidin-4-ylidene)acetamide

MS: 531 (M+1).

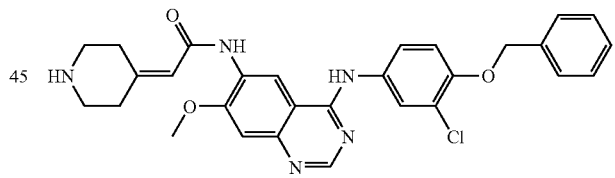

Example 114

N-(4-(4-(3-chlorobenzyloxy)-3-fluorophenylamino)-7-methoxyquinazolin-6-yl)-2-(piperidin-4-ylidene)acetamide

MS: 547 (M$^+$).

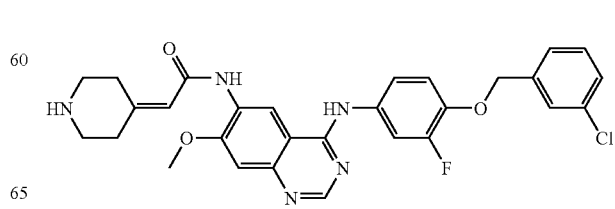

Example 115

N-(4-(4-(3-chloro-4-fluorobenzyloxy)phenylamino)-7-methoxyquinazolin-6-yl)-2-(piperidin-4-ylidene)acetamide

MS: 548 (M+1).

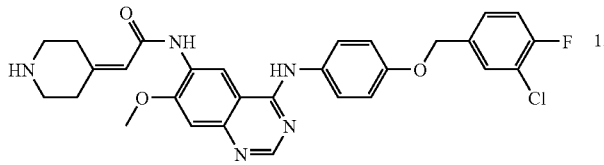

Example 116

N-(4-(3-chloro-4-(pyridin-2-ylmethoxy)phenylamino)quinazolin-6-yl)-2-(1-methylpiperidin-4-ylidene)acetamide

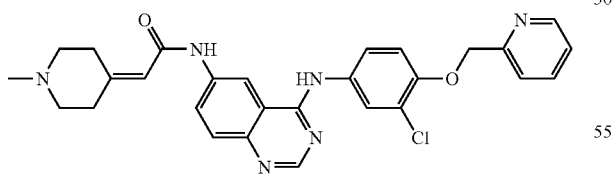

N-(4-(3-chloro-4-(pyridin-2-ylmethoxy)phenylamino)quinazolin-6-yl)-2-(1-piperidin-4-ylidene)acetamide (20 mg, 0.046 mmol), methyl iodide (8.0 mg, 0.056 mmol), anhydrous potassium carbonate (17 mg), and acetonitrile (5 mL) were added to a one-neck flask (50 mL), and stirred at room temperature for 24 hours. After the reaction was complete, the solution was filtered, and evaporated in vacuo to give a solid. The solid was purified by TLC (silica gel plate, thickness 5 mm, chloroform:methanol=95:5). MS: 515 (M+).

The compounds of Examples 117-118 were prepared following the procedure of Example 116.

Example 117

N-(4-(3-chloro-4-(pyridin-2-ylmethoxy)phenylamino)-7-methoxyquinazolin-6-yl)-2-(1-ethylpiperidin-4-ylidene)acetamide

MS: 558 (M+).

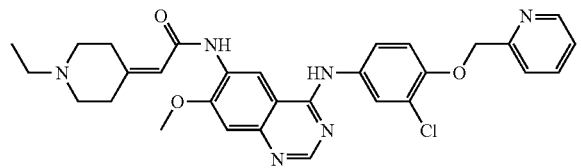

Example 118

N-(4-(3-chloro-4-(pyridin-2-ylmethoxy)phenylamino)-7-methoxyquinazolin-6-yl)-2-(1-(2-methoxyethyl)piperidin-4-ylidene)acetamide

MS: 588 (M+).

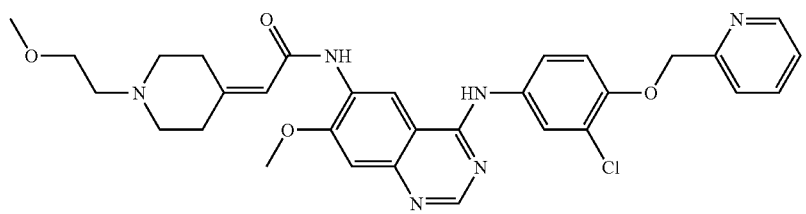

The compounds of Examples 119-131 were prepared following literature procedures.

Example 119

6-Amino-4-(3-chlorophenylamino)-7-methoxyquinoline-3-carbonitrile

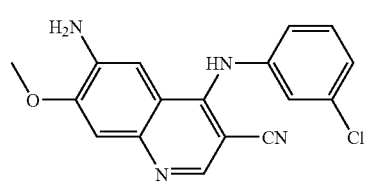

Example 120

6-Amino-4-(3-chloro-4-fluorophenylamino)-7-methoxyquinoline-3-carbonitrile

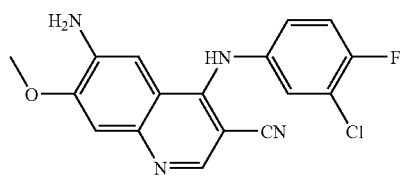

Example 121

6-Amino-4-(3-ethynylphenylamino)-7-methoxyquinoline-3-carbonitrile

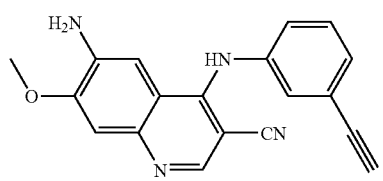

Example 122

6-Amino-4-(3-bromophenylamino)-7-methoxyquinoline-3-carbonitrile

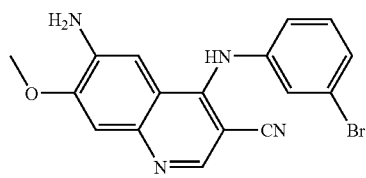

Example 123

6-Amino-4-(3-chloro-4-fluorophenylamino)-7-ethoxyquinoline-3-carbonitrile

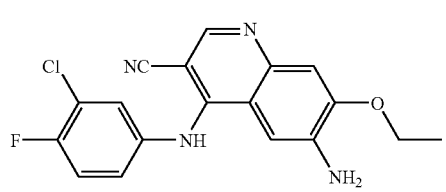

Example 124

6-Amino-7-ethoxy-4-(3-ethynylphenylamino)quinoline-3-carbonitrile

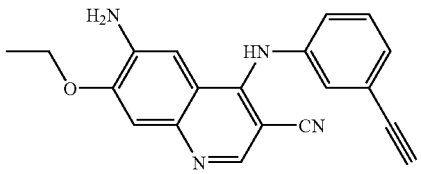

Example 125

6-Amino-4-(3-bromophenylamino)-7-ethoxyquinoline-3-carbonitrile

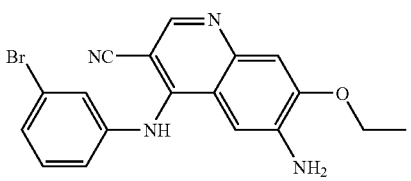

Example 126

6-Amino-4-(3-chloro-4-(pyridin-2-ylmethoxy)phenylamino)-7-methoxyquinoline-3-carbonitrile

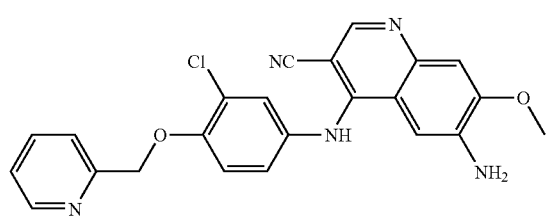

Example 127

6-Amino-4-(3-chloro-4-(pyridin-2-ylmethoxy)phenylamino)-7-ethoxyquinoline-3-carbonitrile

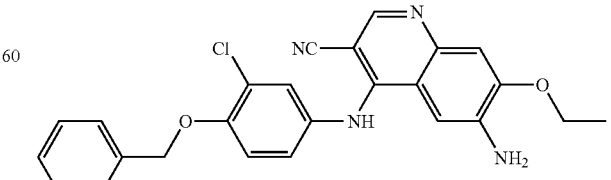

Example 128

4-(4-(3-Fluorobenzyloxy)-3-chlorophenylamino)-6-amino-7-methoxyquinoline-3-carbonitrile

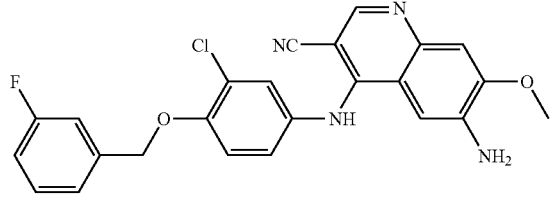

Example 129

4-(4-(3-Fluorobenzyloxy)-3-chlorophenylamino)-6-amino-7-ethoxyquinoline-3-carbonitrile

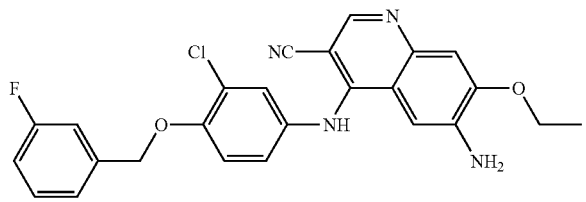

Example 130

6-Amino-4-(4-(3-fluorophenoxy)-3-methoxyphenylamino)-7-methoxyquinoline-3-carbonitrile

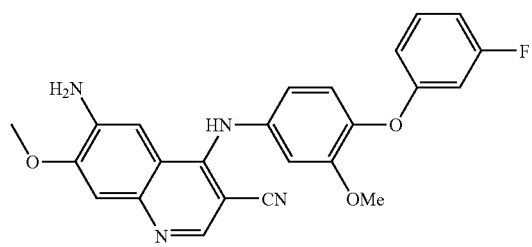

Example 131

6-Amino-7-ethoxy-4-(4-(3-fluorophenoxy)-3-methoxyphenylamino)quinoline-3-carbonitrile

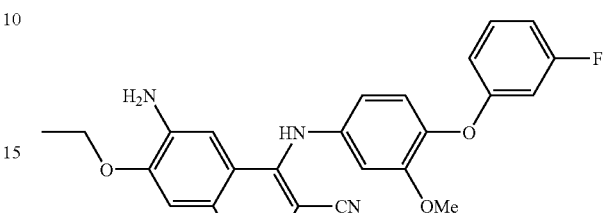

The compounds of Examples 132-145 were prepared following the procedure of Example 104.

Example 132

N-(4-(3-chloro-4-(pyridin-2-ylmethoxy)phenylamino)-3-cyano-7-methoxyquinolin-6-yl)-2-(piperidin-4-ylidene)acetamide

MS: 554 (M+1).

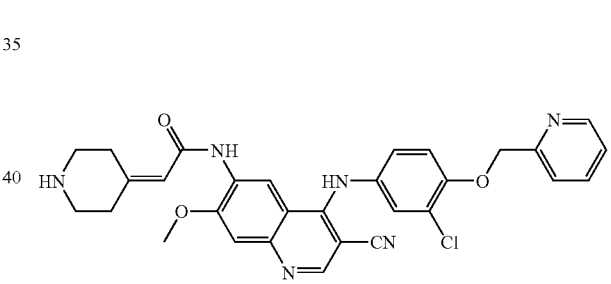

Example 133

N-(4-(3-chloro-4-(pyridin-2-ylmethoxy)phenylamino)-3-cyano-7-ethoxyquinolin-6-yl)-2-(piperidin-4-ylidene)acetamide

MS: 568 (M+1).

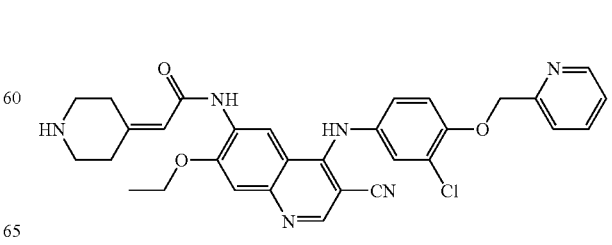

Example 134

N-(4-(4-(3-fluorobenzyloxy)-3-chlorophenylamino)-3-cyano-7-methoxyquinolin-6-yl)-2-(piperidin-4-ylidene)acetamide

MS: 571 (M+).

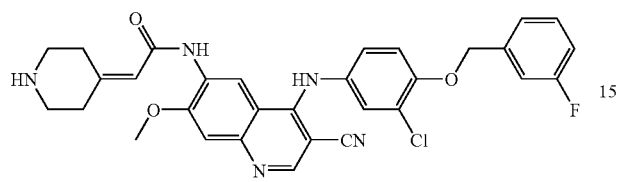

Example 135

N-(4-(4-(3-fluorobenzyloxy)-3-chlorophenylamino)-3-cyano-7-ethoxyquinolin-6-yl)-2-(piperidin-4-ylidene)acetamide

MS: 586 (M+1).

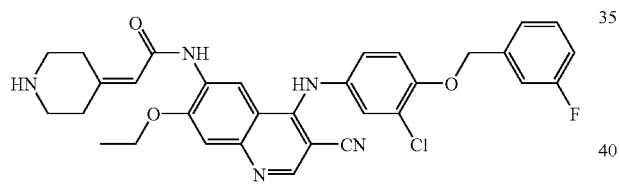

Example 136

N-(4-(3-chloro-4-(3-fluorophenoxy)phenylamino)-3-cyano-7-methoxyquinolin-6-yl)-2-(piperidin-4-ylidene)acetamide

MS: 558 (M+1).

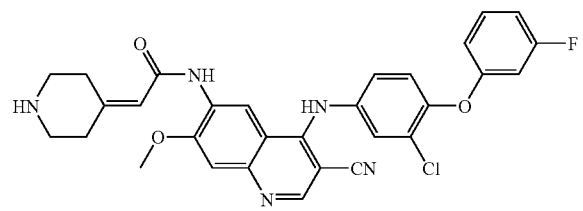

Example 137

N-(4-(3-chlorophenylamino)-3-cyano-7-ethoxyquinolin-6-yl)-2-(piperidin-4-ylidene)acetamide

MS: 461 (M+).

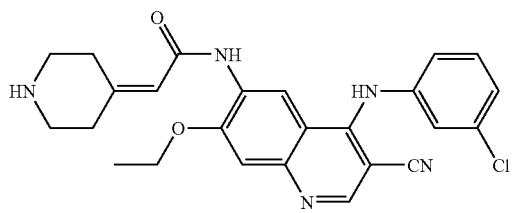

Example 138

N-(4-(3-chlorophenylamino)-3-cyano-7-methoxyquinolin-6-yl)-2-(piperidin-4-ylidene)acetamide

MS: 448 (M+1).

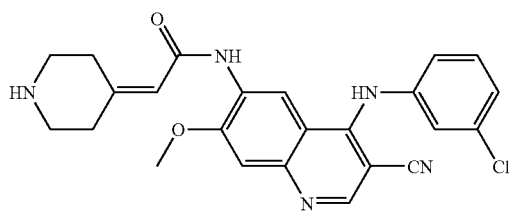

Example 139

N-(4-(3-chloro-4-fluorophenylamino)-3-cyano-7-(2-methoxyethoxy)quinolin-6-yl)-2-(piperidin-4-ylidene)acetamide

MS: 510 (M+1).

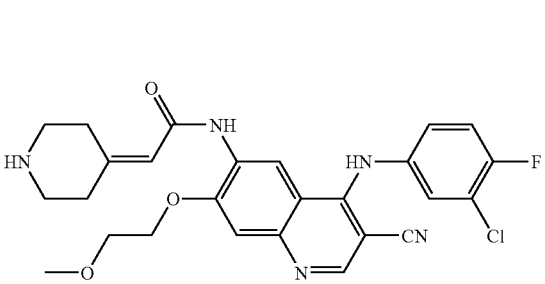

Example 140

N-(4-(3-chloro-4-fluorophenylamino)-3-cyano-7-ethoxyquinolin-6-yl)-2-(piperidin-4-ylidene)acetamide

MS: 480 (M+1).

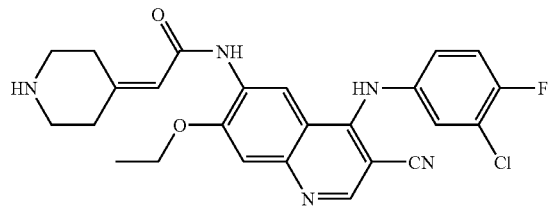

Example 141

N-(4-(3-chloro-4-fluorophenylamino)-3-cyano-7-methoxyquinolin-6-yl)-2-(piperidin-4-ylidene)acetamide

MS: 466 (M+1).

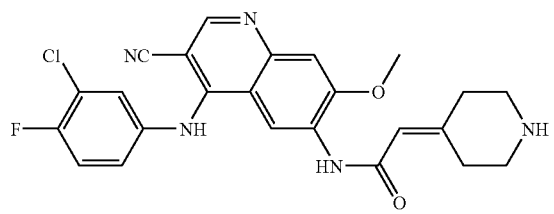

Example 142

N-(3-cyano-7-ethoxy-4-(3-ethynylphenylamino)quinolin-6-yl)-2-(piperidin-4-ylidene)acetamide

MS: 452 (M+1).

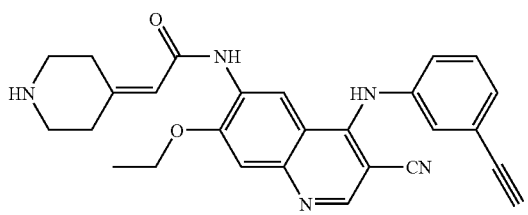

Example 143

N-(3-cyano-4-(3-ethynylphenylamino)-7-methoxyquinolin-6-yl)-2-(piperidin-4-ylidene)acetamide

MS: 438 (M+1).

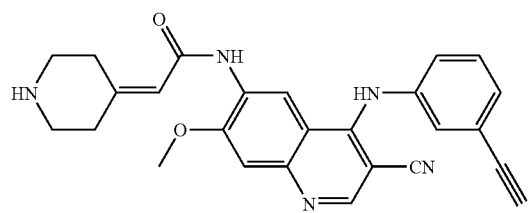

Example 144

N-(4-(3-bromophenylamino)-3-cyano-7-ethoxyquinolin-6-yl)-2-(piperidin-4-ylidene)acetamide

MS: 506 (M$^+$).

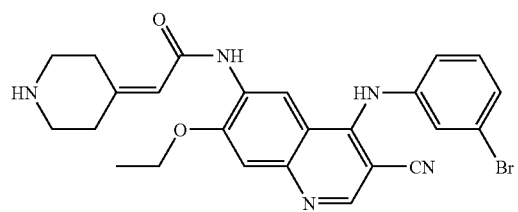

Example 145

N-(4-(3-bromophenylamino)-3-cyano-7-methoxyquinolin-6-yl)-2-(piperidin-4-ylidene)acetamide

MS: 493 (M+1).

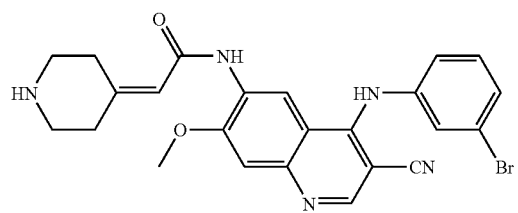

The compounds of Examples 146-154 were prepared following the procedure of Example 116.

Example 146

N-(4-(3-chloro-4-fluorophenylamino)-3-cyano-7-ethoxyquinolin-6-yl)-2-(1-methylpiperidin-4-ylidene)acetamide

MS: 494 (M+1).

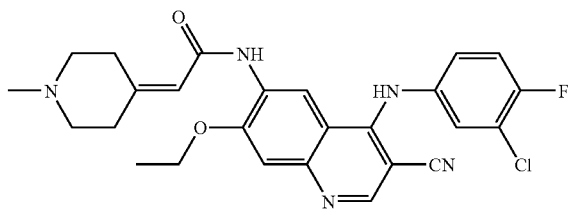

Example 147

N-(4-(3-chloro-4-fluorophenylamino)-3-cyano-7-ethoxyquinolin-6-yl)-2-(1-(2-methoxyethyl)piperidin-4-ylidene)acetamide

MS: 537 (M$^+$).

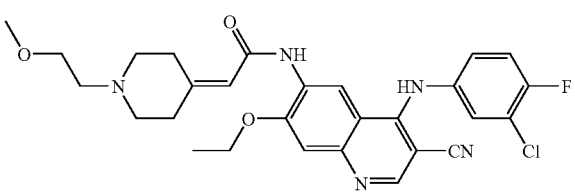

Example 148

N-(3-cyano-7-ethoxy-4-(3-ethynylphenylamino)quinolin-6-yl)-2-(1-methylpiperidin-4-ylidene)acetamide

MS: 466 (M+1).

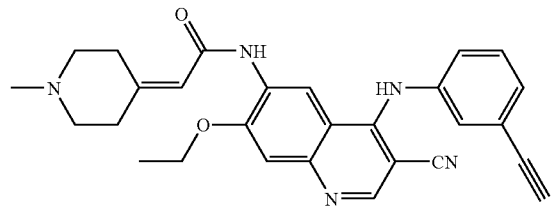

Example 149

N-(3-cyano-7-ethoxy-4-(3-ethynylphenylamino)quinolin-6-yl)-2-(1-(2-methoxyethyl)piperidin-4-ylidene)acetamide

MS: 510 (M+1).

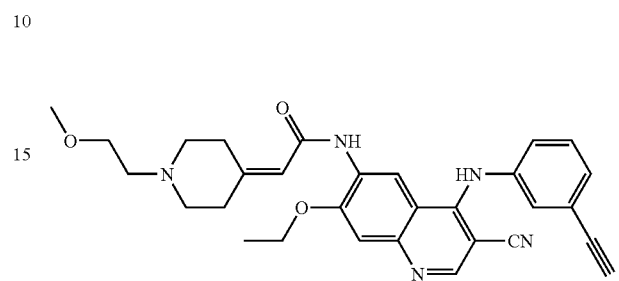

Example 150

N-(4-(3-chloro-4-(pyridin-2-ylmethoxy)phenylamino)-3-cyano-7-ethoxyquinolin-6-yl)-2-(1-methylpiperidin-4-ylidene)acetamide

MS: 582 (M+1).

Example 151

N-(4-(3-chloro-4-(pyridin-2-ylmethoxy)phenylamino)-3-cyano-7-ethoxyquinolin-6-yl)-2-(1-(2-methoxyethyl)piperidin-4-ylidene)acetamide

MS: 626 (M+1).

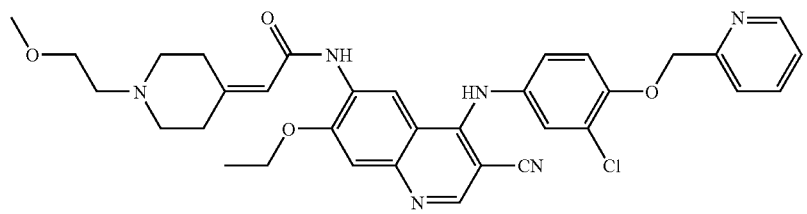

Example 152

N-(4-(4-(3-fluorobenzyloxy)-3-chlorophenylamino)-3-cyano-7-ethoxyquinolin-6-yl)-2-(1-methylpiperidin-4-ylidene)acetamide

MS: 600 (M+1).

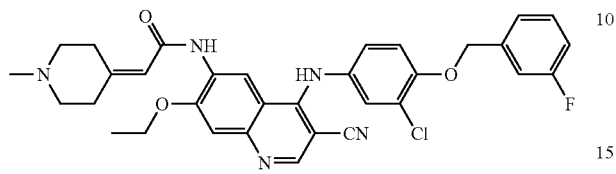

Example 153

N-(4-(4-(3-fluorobenzyloxy)-3-chlorophenylamino)-3-cyano-7-ethoxyquinolin-6-yl)-2-(1-(2-methoxyethyl)piperidin-4-ylidene)acetamide

MS: 643 (M+).

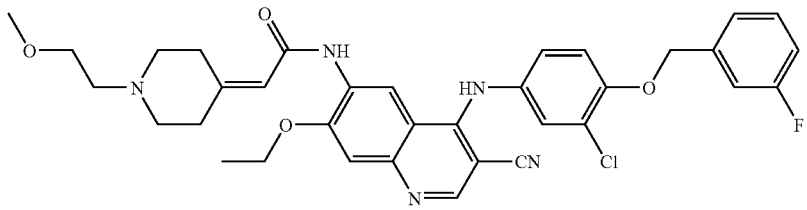

Example 154

N-(4-(3-ethynylphenylamino)-7-methoxyquinazolin-6-yl)-2-(1-(2-methoxyethyl)piperidin-4-ylidene)acetamide

MS: 471 (M+).

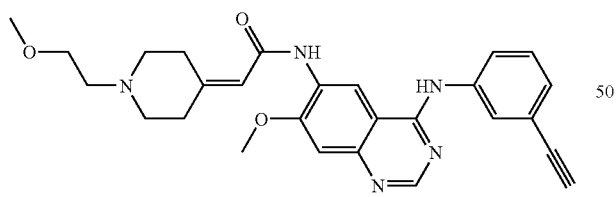

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A compound of formula (I), or a pharmaceutically acceptable salt thereof,

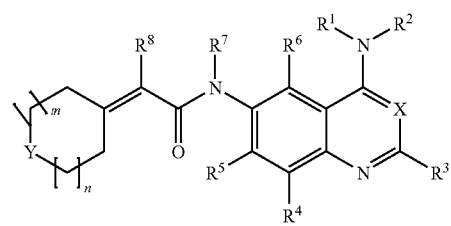

wherein,

X represents N;

Y represents $CH_2$, S, O or $N-R^9$;

$R^1$, $R^3$, $R^7$ and $R^8$ independently represent H, $CF_3$, or $C_{1-6}$alkyl;

$R^2$ represents a substituent of a formula selected from formulas (II), (III), (IV), (V), (VI), (VII), or (VIII);

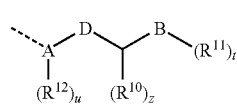

(II)

(III)

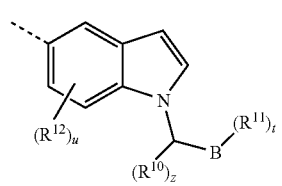

(IV)

(V)

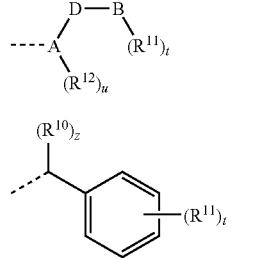

(VI)

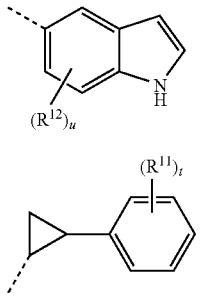

(VII)

(VIII)

R⁴ and R⁶ independently represent H, C₁₋₆alkyl, OC₁₋₆alkyl, OH, F, Cl, Br, OCF₃, or trifluoromethyl;

R⁵ is independently at each occurrence selected from H, F, C₁₋₆alkyl, OH, OC₁₋₆alkyl, OCF₃, OCF₂CH₃, NH₂, NH(C₁₋₆alkyl), N(C₁₋₆alkyl)₂, 1-pyrrolinyl, 1-piperidyl, 4-morpholinyl, Cl, Br, trifluoromethyl, O(CH₂)₂₋₄OC₁₋₆alkyl, O(CH₂)₂₋₄OCF₃, O(CH₂)₂₋₄NH(C₁₋₆alkyl), O(CH₂)₂₋₄N(C₁₋₆alkyl)₂, (1-pyrrolinyl)(CH₂)₂₋₄O, (1-piperidyl)(CH₂)₂₋₄O, (4-morpholinyl)(CH₂)₂₋₄O, NHC(O)H, NHC(O)(C₁₋₆alkyl), N(C₁₋₆alkyl)C(O)(C₁₋₆ alkyl), O(CH₂)₂₋₄OH, N(C₁₋₆alkyl)C(O)O(C₁₋₆ alkyl), N(C₁₋₆alkyl)C(O)OH, NHC(O)O(C₁₋₆alkyl), OC(O)NH(C₁₋₆alkyl), OC(O)N(C₁₋₆alkyl)₂, (1-piperidyl)(CH₂)₂₋₄OC(O), (4-morpholinyl)(CH₂)₂₋₄OC(O), (1-pyrrolinyl)(CH₂)₂₋₄OC(O), (1-imidazolyl)(CH₂)₂₋₄O, (pyrazolyl)(CH₂)₂₋₄O, (triazolyl)(CH₂)₂₋₄OC(O), or Ar(CH₂)₁₋₄O;

R⁹ is independently at each occurrence selected from H, C₁₋₆alkyl, CF₃, CF₂CH₃, (CH₂)₂₋₄OH, (CH₂)₁₋₄OC₁₋₆alkyl, (CH₂)₁₋₄NH(C₁₋₆alkyl), (CH₂)₁₋₄N(C₁₋₆alkyl)₂, (1-pyrrolinyl)(CH₂)₁₋₄, (1-piperidyl)(CH₂)₁₋₄, (4-morpholinyl)(CH₂)₁₋₄, C(O)C₁₋₆alkyl, C(O)(CH₂)₁₋₄OH, C(O)(CH₂)₁₋₄OC₁₋₆alkyl, C(O)(CH₂)₁₋₄N(C₁₋₆alkyl)₂, (1-pyrrolinyl)(CH₂)₁₋₆C(O), (1-piperidyl)(CH₂)₁₋₆C(O), (4-morpholinyl)(CH₂)₁₋₄C(O), C(O)OC₁₋₆alkyl, C(O)O(CH₂)₂₋₄OC₁₋₆alkyl, C(O)O(CH₂)₂₋₄N(C₁₋₆alkyl)₂, (1-pyrrolinyl)(CH₂)₂₋₄OC(O), (1-piperidyl)(CH₂)₂₋₄OC(O), (4-morpholinyl)(CH₂)₂₋₄OC(O), (CH₂)₁₋₄C(O)OC₁₋₆alkyl, or Ar(CH₂)₁₋₄;

R¹⁰ represents H, C₁₋₆alkyl, or F;

R¹¹ and R¹² represent independently at each occurrence H, F, Cl, Br, I, CN, NO₂, CF₃, OH, NH₂, C₁₋₄alkyl, OC₁₋₄alkyl, OCF₃, OCF₂CH₃, NH(C₁₋₄alkyl), N(C₁₋₄alkyl)₂, OC(O)C₁₋₄alkyl, NHC(O)H, NHC(O)C₁₋₄alkyl, N(C₁₋₄alkyl)C(O)C₁₋₄alkyl, C(O)OC₁₋₄alkyl, C(O)NHC₁₋₄alkyl, C(O)N(C₁₋₄alkyl)₂, COOH, C(O)C₁₋₄alkyl, S(O)C₁₋₄alkyl, SO₂C₁₋₄alkyl, SO₂NHC₁₋₄alkyl, or SO₂N(C₁₋₄alkyl)₂;

A represents a 5-7 membered aromatic ring containing from 0 to 4 heteroatoms selected from N, O or S; or a polycyclic aromatic group consisting of two or three 5 to 7-membered fused rings;

B represents a 5-7 membered aromatic ring containing from 0 to 4 heteroatoms selected from N, O or S; or a polycyclic aromatic group consisting of two or three 5 to 7-membered fused rings;

Ar is phenyl;

D represents O, S, NH, or methylene;

m and n independently represent an integer from 0 to 4;

z is 1, or 2; and t and u independently represent an integer from 1 to 4.

2. The compound of claim 1, wherein
R¹, R³, R⁴, R⁶ and R⁷ independently represent H, and
R⁸ represents H, CH₃, or CH₂CH₃.

3. The compound of claim 1, wherein R⁵ at each occurrence is independently selected from H, F, OCF₃, OC₁₋₄alkyl, O(CH₂)₂₋₃OC₁₋₄alkyl, O(CH₂)₂₋₃N(C₁₋₄alkyl)₂, 2-(1-pyrrolinyl)ethoxyl, 2-(1-piperidyl)ethoxyl, 2-(4-morpholinyl)ethoxyl, 3-(1-pyrrolinyl)propyloxyl, 3-(1-piperidyl)propyloxyl, 3-(4-morpholinyl)propyloxyl, or Ph(CH₂)₁₋₄O.

4. The compound of claim 1, wherein
Y represents N—R⁹,
R⁹ at each occurrence is independently selected from H, CF₃, C₁₋₆alkyl, (CH₂)₂₋₄OH, (CH₂)₂₋₄OC₁₋₆alkyl, (CH₂)₂₋₄N(C₁₋₆alkyl)₂, (1-pyrrolinyl)-(CH₂)₂₋₄, (1-piperidyl)-(CH₂)₂₋₄, (4-morpholinyl)-(CH₂)₂₋₄, C(O)OC₁₋₆ alkyl, (CH₂)₄C(O)OC₁₋₆alkyl, or Ph(CH₂)₁₋₄.

5. The compound of claim 1, wherein m and n independently represent 0, 1 or 2.

6. The compound of claim 1, being
tert-butyl 4-((4-(3-ethynylphenylamino)quinazolin-6-ylcarbamoyl)methylene)piperidine-1-carboxylate;
N-(4-(3-ethynylphenylamino)quinazolin-6-yl)-2-(piperidin-4-ylidene)acetamide trifluoroacetate;
N-(4-(3-ethynylphenylamino)quinazolin-6-yl)-2-(piperidin-4-ylidene)acetamide;
N-(4-(3-ethynylphenylamino)quinazolin-6-yl)-2-(1-methylpiperidin-4-ylidene)acetamide;
2-(1-ethylpiperidin-4-ylidene)-N-(4-(3-ethynylphenylamino)quinazolin-6-yl)acetamide;
2-(1-benzylpiperidin-4-ylidene)-N-(4-(3-ethynylphenylamino)quinazolin-6-yl)acetamide;
N-(4-(3-ethynylphenylamino)quinazolin-6-yl)-2-(1-(2-methoxyethyl)piperidin-4-ylidene)acetamide;
methyl 2-(4-((4-(3-ethynylphenylamino)quinazolin-6-ylcarbamoyl)methylene)piperidin-1-yl)acetate;
N-(4-(3-ethynylphenylamino)quinazolin-6-yl)-2-(1-isopropylpiperidin-4-ylidene)acetamide;
N-(4-(3-ethynylphenylamino)quinazolin-6-yl)-2-(1-(2-hydroxyethyl)piperidin-4-ylidene)acetamide;
tert-butyl 4-((4-(phenylamino)quinazolin-6-ylcarbamoyl)methylene)piperidine-1-carboxylate;
tert-butyl 4-((4-(3-chloro-4-fluorophenylamino)quinazolin-6-ylcarbamoyl)methylene)piperidine-1-carboxylate;
tert-butyl 4-((4-(3-bromophenylamino)quinazolin-6-ylcarbamoyl)methylene)piperidine-1-carboxylate;
tert-butyl 4-((4-((S)-1-phenylethylamino)quinazolin-6-ylcarbamoyl)methylene)piperidine-1-carboxylate;
tert-butyl 4-((4-((R)-1-phenylethylamino)quinazolin-6-ylcarbamoyl)methylene)piperidine-1-carboxylate;
tert-butyl 4-((4-(3-chlorophenylamino)quinazolin-6-ylcarbamoyl)methylene)piperidine-1-carboxylate;
tert-butyl 4-((4-(3-chlorophenylamino)-7-fluoroquinazolin-6-ylcarbamoyl)methylene)piperidine-1-carboxylate;
tert-butyl 4-((4-(3-bromophenylamino)-7-methoxyquinazolin-6-ylcarbamoyl)methylene)piperidine-1-carboxylate;
tert-butyl 4-((4-(3-bromophenylamino)-7-ethoxyquinazolin-6-ylcarbamoyl)methylene)piperidine-1-carboxylate;
tert-butyl 4-((7-(2-methoxyethoxy)-4-(3-bromophenylamino)quinazolin-6-ylcarbamoyl)methylene)piperidine-1-carboxylate;
tert-butyl 4-((4-(1H-indol-5-ylamino)quinazolin-6-ylcarbamoyl)methylene)piperidine-1-carboxylate;

tert-butyl 4-((4-(3-ethynylphenylamino)-7-methoxyquinazolin-6-ylcarbamoyl)methylene)piperidine-1-carboxylate;
tert-butyl 4-((4-(3-chloro-4-fluorophenylamino)-7-methoxyquinazolin-6-ylcarbamoyl)methylene)piperidine-1-carboxylate;
tert-butyl 4-((4-(1H-indol-5-ylamino)-7-methoxyquinazolin-6-ylcarbamoyl)methylene)piperidine-1-carboxylate;
tert-butyl 4-((4-(3-bromophenylamino)-7-(3-methoxypropoxy)quinazolin-6-ylcarbamoyl)methylene)piperidine-1-carboxylate;
tert-butyl 4-((4-(3-bromophenylamino)-7-(3-morpholinopropoxy)quinazolin-6-ylcarbamoyl)methylene)piperidine-1-carboxylate;
tert-butyl 4-((7-(2-methoxyethoxy)-4-(3-ethynylphenylamino)quinazolin-6-ylcarbamoyl)methylene)piperidine-1-carboxylate;
tert-butyl 4-((7-(2-methoxyethoxy)-4-(3-chloro-4-fluorophenylamino)quinazolin-6-ylcarbamoyl)methylene)piperidine-1-carboxylate;
tert-butyl 4-((4-(1H-indol-5-ylamino)-7-(2-methoxyethoxy)quinazolin-6-ylcarbamoyl)methylene)piperidine-1-carboxylate;
N-(4-(3-chlorophenylamino)-7-fluoroquinazolin-6-yl)-2-(piperidin-4-ylidene)acetamide;
N-(4-(phenylamino)quinazolin-6-yl)-2-(piperidin-4-ylidene)acetamide;
N-(4-(3-chloro-4-fluorophenylamino)quinazolin-6-yl)-2-(piperidin-4-ylidene)acetamide;
N-(4-(3-bromophenylamino)quinazolin-6-yl)-2-(piperidin-4-ylidene)acetamide;
N-(4-((S)-1-phenylethylamino)quinazolin-6-yl)-2-(piperidin-4-ylidene)acetamide;
N-(4-((R)-1-phenylethylamino)quinazolin-6-yl)-2-(piperidin-4-ylidene)acetamide;
N-(4-(3-chlorophenylamino)quinazolin-6-yl)-2-(piperidin-4-ylidene)acetamide;
N-(4-(3-bromophenylamino)-7-(3-morpholinopropoxy)quinazolin-6-yl)-2-(piperidin-4-ylidene)acetamide;
N-(4-(3-bromophenylamino)-7-methoxyquinazolin-6-yl)-2-(piperidin-4-ylidene)acetamide;
N-(4-(3-bromophenylamino)-7-ethoxyquinazolin-6-yl)-2-(piperidin-4-ylidene)acetamide;
N-(4-(3-bromophenylamino)-7-(2-methoxyethoxy)quinazolin-6-yl)-2-(piperidin-4-ylidene)acetamide;
N-(4-(1H-indol-5-ylamino)quinazolin-6-yl)-2-(piperidin-4-ylidene)acetamide;
N-(4-(3-ethynylphenylamino)-7-methoxyquinazolin-6-yl)-2-(piperidin-4-ylidene)acetamide;
N-(4-(3-chloro-4-fluorophenylamino)-7-methoxyquinazolin-6-yl)-2-(piperidin-4-ylidene)acetamide;
N-(4-(1H-indol-5-ylamino)-7-methoxyquinazolin-6-yl)-2-(piperidin-4-ylidene)acetamide;
(S)—N-(7-methoxy-4-(1-phenylethylamino)quinazolin-6-yl)-2-(piperidin-4-ylidene)acetamide;
(R)—N-(7-methoxy-4-(1-phenylethylamino)quinazolin-6-yl)-2-(piperidin-4-ylidene)acetamide;
N-(4-(3-ethynylphenylamino)-7-(2-methoxyethoxy)quinazolin-6-yl)-2-(piperidin-4-ylidene)acetamide;
N-(4-(3-chloro-4-fluorophenylamino)-7-(2-methoxyethoxy)quinazolin-6-yl)-2-(piperidin-4-ylidene)acetamide;
N-(4-(3-ethynylphenylamino)-7-(3-morpholinopropoxy)quinazolin-6-yl)-2-(piperidin-4-ylidene)acetamide;
N-(4-(3-ethynylphenylamino)-7-(3-methoxypropoxy)quinazolin-6-yl)-2-(piperidin-4-ylidene)acetamide;
N-(4-(3-ethynylphenylamino)-7-methoxyquinazolin-6-yl)-2-(1-methylpiperidin-4-ylidene)acetamide;
N-(7-ethoxy-4-(3-ethynylphenylamino)quinazolin-6-yl)-2-(1-ethylpiperidin-4-ylidene)acetamide;
2-(1-ethylpiperidin-4-ylidene)-N-(4-(3-ethynylphenylamino)-7-methoxyquinazolin-6-yl)acetamide;
N-(7-ethoxy-4-(3-ethynylphenylamino)quinazolin-6-yl)-2-(1-methylpiperidin-4-ylidene)acetamide;
N-(4-(3-bromophenylamino)quinazolin-6-yl)-2-(1-methylpiperidin-4-ylidene)acetamide;
N-(4-(3-bromophenylamino)quinazolin-6-yl)-2-(1-ethylpiperidin-4-ylidene)acetamide;
N-(4-(3-bromophenylamino)quinazolin-6-yl)-2-(1-(2-methoxyethyl)piperidin-4-ylidene)acetamide;
N-(4-(3-bromophenylamino)-7-methoxyquinazolin-6-yl)-2-(1-methylpiperidin-4-ylidene)acetamide;
N-(4-(3-bromophenylamino)-7-methoxyquinazolin-6-yl)-2-(1-ethylpiperidin-4-ylidene)acetamide;
N-(4-(3-bromophenylamino)-7-methoxyquinazolin-6-yl)-2-(1-(2-methoxyethyl)piperidin-4-ylidene)acetamide;
N-(4-(3-bromophenylamino)-7-methoxyquinazolin-6-yl)-2-(1-(3-methoxypropyl)piperidin-4-ylidene)acetamide;
N-(4-(3-bromophenylamino)-7-ethoxyquinazolin-6-yl)-2-(1-methylpiperidin-4-ylidene)acetamide;
N-(4-(3-bromophenylamino)-7-ethoxyquinazolin-6-yl)-2-(1-ethylpiperidin-4-ylidene)acetamide;
N-(4-(3-bromophenylamino)-7-ethoxyquinazolin-6-yl)-2-(1-(2-methoxyethyl)piperidin-4-ylidene)acetamide;
N-(4-(3-bromophenylamino)-7-(2-methoxyethoxy)quinazolin-6-yl)-2-(1-methylpiperidin-4-ylidene)acetamide;
N-(4-(3-bromophenylamino)-7-(3-methoxypropoxy)quinazolin-6-yl)-2-(1-methylpiperidin-4-ylidene)acetamide;
N-(4-(3-bromophenylamino)-7-(3-(dimethylamino)propoxy)quinazolin-6-yl)-2-(1-methylpiperidin-4-ylidene)acetamide;
N-(4-(3-bromophenylamino)-7-(3-morpholinopropoxy)quinazolin-6-yl)-2-(1-methylpiperidin-4-ylidene)acetamide;
N-(4-(3-chlorophenylamino)-7-fluoroquinazolin-6-yl)-2-(1-methylpiperidin-4-ylidene)acetamide;
N-(4-(3-chlorophenylamino)-7-fluoroquinazolin-6-yl)-2-(1-ethylpiperidin-4-ylidene)acetamide;
N-(4-(3-chlorophenylamino)-7-fluoroquinazolin-6-yl)-2-(1-(2-methoxyethyl)piperidin-4-ylidene)acetamide;
N-(4-(3-chloro-4-fluorophenylamino)-7-methoxyquinazolin-6-yl)-2-(1-methylpiperidin-4-ylidene)acetamide;
N-(4-(3-chloro-4-fluorophenylamino)-7-methoxyquinazolin-6-yl)-2-(1-(2-methoxyethyl)piperidin-4-ylidene)acetamide;
N-(4-(3-chloro-4-fluorophenylamino)quinazolin-6-yl)-2-(1-(2-methoxyethyl)piperidin-4-ylidene)acetamide;
N-(4-(1H-indol-5-ylamino)quinazolin-6-yl)-2-(1-methylpiperidin-4-ylidene)acetamide;
N-(4-(1H-indol-5-ylamino)quinazolin-6-yl)-2-(1-ethylpiperidin-4-ylidene)acetamide;
N-(4-(1H-indol-5-ylamino)quinazolin-6-yl)-2-(1-(2-methoxyethyl)piperidin-4-ylidene)acetamide;
(S)-2-(1-methylpiperidin-4-ylidene)-N-(4-(1-phenylethylamino)quinazolin-6-yl)acetamide;
(S)-2-(1-ethylpiperidin-4-ylidene)-N-(4-(1-phenylethylamino)quinazolin-6-yl)acetamide;

(S)-2-(1-(2-methoxyethyl)piperidin-4-ylidene)-N-(4-(1-phenylethylamino)quinazolin-6-yl)acetamide;

(S)—N-(7-(2-methoxyethoxy)-4-(1-phenylethylamino)quinazolin-6-yl)-2-(piperidin-4-ylidene)acetamide;

N-(4-(1H-indol-5-ylamino)-7-(2-methoxyethoxy)quinazolin-6-yl)-2-(piperidin-4-ylidene)acetamide;

N-(4-(3-bromophenylamino)quinazolin-6-yl)-2-(pyrrolidin-3-ylidene)acetamide;

N-(7-methoxy-4-(2-phenylcyclopropylamino)quinazolin-6-yl)-2-(1-(2-methoxyethyl)piperidin-4-ylidene)acetamide;

tert-butyl 4-((4-(4-((pyridin-2-yl)methoxy)-3-chlorophenylamino)quinazolin-6-ylcarbamoyl)methylene)piperidine-1-carboxylate;

N-(4-(3-chloro-4-(pyridin-2-ylmethoxy)phenylamino)quinazolin-6-yl)-2-(piperidin-4-ylidene)acetamide trifluoroacetate;

N-(4-(3-chloro-4-(pyridin-2-ylmethoxy)phenylamino)quinazolin-6-yl)-2-(piperidin-4-ylidene)acetamide;

N-(4-(4-(3-fluorobenzyloxy)-3-chlorophenylamino)-7-methoxyquinazolin-6-yl)-2-(piperidin-4-ylidene)acetamide;

N-(4-(4-(3-fluorobenzyloxy)-3-chlorophenylamino)-7-(3-methoxypropoxy)quinazolin-6-yl)-2-(piperidin-4-ylidene)acetamide;

N-(4-(3-chloro-4-(pyridin-2-ylmethoxy)phenylamino)-7-ethoxyquinazolin-6-yl)-2-(piperidin-4-ylidene)acetamide;

N-(4-(3-chloro-4-(pyridin-2-ylmethoxy)phenylamino)-7-methoxyquinazolin-6-yl)-2-(piperidin-4-ylidene)acetamide;

N-(4-(3-chloro-4-(pyridin-2-ylmethoxy)phenylamino)-7-fluoroquinazolin-6-yl)-2-(piperidin-4-ylidene)acetamide;

N-(7-methoxy-4-(3-methoxy-4-phenoxyphenylamino)quinazolin-6-yl)-2-(piperidin-4-ylidene)acetamide;

N-(7-methoxy-4-(4-(3-methoxyphenoxy)phenylamino)quinazolin-6-yl)-2-(piperidin-4-ylidene)acetamide;

N-(4-(2-chloro-4-(pyridin-2-ylmethoxy)phenylamino)-7-methoxyquinazolin-6-yl)-2-(piperidin-4-ylidene)acetamide;

N-(4-(4-(benzyloxy)-3-chlorophenylamino)-7-methoxyquinazolin-6-yl)-2-(piperidin-4-ylidene)acetamide;

N-(4-(4-(3-chlorobenzyloxy)-3-fluorophenylamino)-7-methoxyquinazolin-6-yl)-2-(piperidin-4-ylidene)acetamide;

N-(4-(4-(3-chloro-4-fluorobenzyloxy)phenylamino)-7-methoxyquinazolin-6-yl)-2-(piperidin-4-ylidene)acetamide;

N-(4-(3-chloro-4-(pyridin-2-ylmethoxy)phenylamino)quinazolin-6-yl)-2-(1-methylpiperidin-4-ylidene)acetamide;

N-(4-(3-chloro-4-(pyridin-2-ylmethoxy)phenylamino)-7-methoxyquinazolin-6-yl)-2-(1-ethylpiperidin-4-ylidene)acetamide;

N-(4-(3-chloro-4-(pyridin-2-ylmethoxy)phenylamino)-7-methoxyquinazolin-6-yl)-2-(1-(2-methoxyethyl)piperidin-4-ylidene)acetamide;

N-(4-(3-ethynylphenylamino)-7-methoxyquinazolin-6-yl)-2-(1-(2-methoxyethyl)piperidin-4-ylidene)acetamide.

7. A pharmaceutical preparation comprising a pharmaceutically acceptable excipient and a compound of claim 1.

8. The pharmaceutical preparation of claim 7, formulated for a mode of administration selected from oral, intravenous, intraperitoneal, subcutaneous, intramuscular, nasal, ocular, pulmonary, anal, vaginal, or epidermal.

* * * * *